US008658832B2

(12) United States Patent
Yersin et al.

(10) Patent No.: US 8,658,832 B2
(45) Date of Patent: Feb. 25, 2014

(54) LUMINESCENT METAL COMPLEXES FOR ORGANIC ELECTRONIC DEVICES

(75) Inventors: Hartmut Yersin, Sinzing (DE); Rafal Czerwieniec, Regensburg (DE); Uwe Monkowius, Linz (AT)

(73) Assignee: Merck Patent GmbH (DE)

( * ) Notice: Subject to any disclaimer, the term of this patent is extended or adjusted under 35 U.S.C. 154(b) by 502 days.

(21) Appl. No.: 12/667,611

(22) PCT Filed: Jul. 3, 2008

(86) PCT No.: PCT/EP2008/005426
§ 371 (c)(1),
(2), (4) Date: Jan. 4, 2010

(87) PCT Pub. No.: WO2009/003700
PCT Pub. Date: Jan. 8, 2009

(65) Prior Publication Data
US 2010/0176386 A1    Jul. 15, 2010

(30) Foreign Application Priority Data
Jul. 5, 2007  (DE) .......................... 10 2007 031 261

(51) Int. Cl.
C07F 15/00  (2006.01)
C07F 9/02  (2006.01)
C07F 5/02  (2006.01)

(52) U.S. Cl.
USPC ................. 568/2; 546/2; 546/4; 549/3; 568/3

(58) Field of Classification Search
USPC ............................... 546/2, 4; 549/3; 568/2, 3
See application file for complete search history.

(56) References Cited

U.S. PATENT DOCUMENTS

| 7,345,301 | B2 | 3/2008 | Gerhard et al. |
| 2005/0069729 | A1 | 3/2005 | Ueda et al. |
| 2006/0175958 | A1 | 8/2006 | Gerhard et al. |
| 2006/0255332 | A1 | 11/2006 | Becker et al. |
| 2007/0176147 | A1 | 8/2007 | Buesing et al. |
| 2009/0134384 | A1 | 5/2009 | Stoessel et al. |
| 2009/0167166 | A1 | 7/2009 | Bach et al. |
| 2009/0212280 | A1 | 8/2009 | Werner et al. |
| 2009/0302752 | A1 | 12/2009 | Parham et al. |

FOREIGN PATENT DOCUMENTS

| DE | 102007002714 A1 | 7/2008 |
| EP | 1205527 A1 | 5/2002 |
| EP | 1617710 A1 | 1/2006 |
| EP | 1617711 A1 | 1/2006 |
| EP | 1731584 A1 | 12/2006 |
| JP | 2004-288318 A | 10/2004 |
| JP | 2005-347160 A | 12/2005 |
| WO | WO-2004/093207 A2 | 10/2004 |
| WO | WO-2005/003253 A2 | 1/2005 |
| WO | WO-2005/011013 A1 | 2/2005 |
| WO | WO-2005/039246 A1 | 4/2005 |
| WO | WO-2005/086251 A2 | 9/2005 |
| WO | WO-2005/111172 A2 | 11/2005 |
| WO | WO-2006/117052 A1 | 11/2006 |
| WO | WO-2007/137725 A1 | 12/2007 |

OTHER PUBLICATIONS

Crespo et al. "Luminescent nido-Carborane—Diphosphine Anions [(PR2)2C2B9H10]—(R=Ph, iPr). Modification of Their Luminescence Properties upon Formation of Three-Coordinate Gold(I) Complexes" Inorganic Chemistry, 2003, pp. 2061-2068.*

Calborda, M., et al., "Synthesis, Structure, Luminescence, and Theoretical Studies of Tetranuclear Gold Clusters with Phosphinocarborane Ligands", Inorg. Chem., vol. 39, pp. 4280-4285, (2000).

Cheung, M., et al., Highly Electrophilic Half-Sandwich Group 4 Metallacarorane Alkyls. C-H/C-O Activation and Alkyne Insertion Reactions at Neutral Metal Complexes, Organometallics, vol. 24, pp. 5217-5220, (2005).

Crespo, O., et al., Luminescent Dinuclear Gold Derivatives With The Bridging Diphosphine [(PPh2)$_2$ C$_2$ B$_2$ H$_{10}$], 22th. International Conference on Organometallic Chemistry ICOMOC, p. 856, (2006).

Crespo, O., et al., "Luminescent nido-Carborane-Disphosphine Anions [(PR$_2$ )$_2$ B $_9$ H$_{10}$ ] (R = Ph, iPr). Modification of Their Luminescence Properties upon Formation of Three-Coordinate Gold(I) Complezes", Inorganic Chemistry, vol. 42, No. 6, pp. 2061-2068, (2003).

Dou, J., et al., Synthesis and Crystal Structure of Three Caborane Complexes, [M{7,8-(OPPh$_2$ -7,8-C$_2$ B$_9$ H$_{10}$ }$_2$ ] (M=Cu, Zn) and [Ni(thf){7,8-(C$_2$ B$_9$ H$_{10}$ }$_2$ ]-thf, and Two Carbonate Copounds, 1-OPPh$_2$)-2-(PPh$_2$)-1,2-C$_2$ B$_{10}$ H$_{10}$ and H[7,8-OPPh$_2$)2-7,8-C$_2$B$_9$H$_{10}$ ]-0.25C$_2$ H$_5$ OH, Eur. Journal Inorganic Chemistry, pp. 53-59, (2007).

Teixidor, F., et al., "The formation of nido [7,8-(PR$_2$ )$_2$ -7,8-C$_2$ B$_9$ H$_{10}$ ] from closo 1,2-(PR$_2$ )$_2$ —1,2-C$_2$ B$_{10}$ H$_{10}$ (R=Ph, Et, Pr or OEt) : a process enhanced by complexation", Journal of Organometallic Chemistry, vol. 509, pp. 139-150, (1996).

Teixidor, F., "Rhodium Complexes with the New Anionic Diphosphine [7,8-(PPh$_2$ )$_2$ -7,8-C$_2$ B$_9$ H$_{10}$ ]-Ligand", Organometalics, vol. 15, pp. 3154-3180, (1996).

Viñas, et al., "Reactions of Pd(II) with closo-1,2 dicarbadodecaborane-1,2-diphosphines", Journal of Organometallic Chemistry, vol. 555, pp. 17-23, (1998).

* cited by examiner

Primary Examiner — Joseph Kosack
(74) Attorney, Agent, or Firm — Novak Druce Connolly Bove + Quigg LLP

(57) ABSTRACT

The present invention relates to auxiliary ligands for luminescent metal complexes, particularly emitter complexes having such auxiliary ligands, and particularly light-emitting devices, and particularly organic light-emitting devices (OLED) having metal complexes, which have the auxiliary ligands according to the invention.

20 Claims, 13 Drawing Sheets

| 7 | Cathode, Al: 60 nm |
|---|---|
| 6 | Interlayer CsF: 0.8 nm |
| 5 | ETL, Alq$_3$: 40 nm |
| 4 | Emitter layer: 30 to 100 nm |
| 3 | HTL, PEDOT:PSS: 50 nm |
| 2 | Anode, ITO: 40 nm |
| 1 | Support material, glass |

Figure 4

| | |
|---|---|
| Cathode: Al | 200 nm |
| Interlayer: LiF | 0.8 nm |
| Electron-transport layer ETL: Alq$_3$ | 40 nm |
| Emitter layer EML: CBP with 6% complex doping | 70 nm |
| Hole-transport layer HTL: α-NPD | 30 nm |
| Hole-injection layer HIL: CuPc | 10 nm |
| Anode ITO | 40 nm |
| Support material, glass | |

ETL = electron-transport layer

EML = emitter layer

HTL = hole-transport layer

HIL = hole-injection layer

Alq$_3$ = aluminium 8-hydroxyquinoline

α-NPD = 4,4'-bis(N-(1-naphthyl)-N-phenylamino)biphenyl

CuPc = copper phthalocyanine

CBP = 4,4'-bis(N-carbozolyl)biphenyl

ITO = indium tin oxide

| 9 | Cathode |
| 8 | Interlayer |
| 7 | ETL |
| 6 | Hole-blocking layer |
| 5 | Emitter layer |
| 4 | Electron-blocking layer |
| 3 | HTL |
| 2 | Anode |
| 1 | Support material, glass |

Pt(ppy)(7a)

Pt(dfppy)(1a)

Pt(ppy)(7b)

Cu(dpphen)(7a)

Ir(ppy)₂(7a)

Ir(dfppy)₂(7a)

| Solvent | mthf | PMMA | Solid |
|---|---|---|---|
| Temperature [K] | 77 | 300 | 300 |
| Lifetime [μs] | 48 | 37 | 35 |

Pt(dfppy)(7a)

| Solvent | mthf | PMMA | Solid |
|---|---|---|---|
| Temperature [K] | 77 | 300 | 300 |
| Lifetime [µs] | 47 | 38 | 39 |

Pt(ppy)(7b)

| Solvent | mthf | PMMA | Solid |
|---|---|---|---|
| Temperature [K] | 77 | 300 | 300 |
| Lifetime [μs] | 26 | 23 | 17 |

| Solvent | mthf | PMMA | Solid |
|---|---|---|---|
| Temperature [K] | 77 | 300 | 300 |
| Lifetime [μs] | 48 | 10 | 9 |

| Solvent | Toluene | PMMA |
|---|---|---|
| Temperature [K] | 77 | 300 |
| Lifetime [μs] | 9 | 2 |

| Solvent | mthf | PMMA | Solid |
|---|---|---|---|
| Temperature [K] | 77 | 300 | 300 |
| Lifetime [µs] | 24 | 6 | |

Ir(dfppy)₂(7a)

| Solvent | mthf | PMMA | Solid |
|---|---|---|---|
| Temperature [K] | 77 | 300 | 300 |
| Lifetime [µs] | 28 | 5 | |

LUMINESCENT METAL COMPLEXES FOR ORGANIC ELECTRONIC DEVICES

The present invention relates to the use of metal complexes containing bulky carborane-containing auxiliary ligands in organic electronic devices, in particular in light-emitting devices, to metal complexes containing these ligands, and to organic electronic devices, in particular organic light-emitting diodes (OLEDs), comprising metal complexes which contain the carborane-containing auxiliary ligand.

A drastic change in the area of display-screen and lighting technology is currently evident. It is possible to manufacture flat displays or lighting areas having a thickness of less than 0.5 mm. These are characterised by many fascinating properties. Thus, for example, lighting areas can be produced as wallpapers with very low energy consumption. However, it is particularly interesting that it is possible to produce colour display screens having hitherto unachievable colour fidelity, brightness and viewing-angle independence, with low weight and very low power consumption. The display screens can be designed as microdisplays or large display screens having an area of several m² in rigid or flexible form, but also as transmission or reflection displays. It is furthermore possible to employ simple and cost-saving production processes, such as screen printing or ink-jet printing or vacuum sublimation. Very inexpensive manufacture is thus facilitated compared with conventional flat display screens. This novel technology is based on the principle of OLEDs, organic light-emitting diodes (organic electroluminescent devices).

OLEDs consist predominantly of organic layers, which are also flexible and inexpensive to manufacture. OLED components can be designed with large areas as lighting units, but also in small form as pixels for displays. An overview of the function of OLEDs is given, for example, in H. Yersin, Top. Curr. Chem. 2004, 241, 1 and H. Yersin, "Highly Efficient OLEDs with Phosphorescent Materials", Wiley-VCH, Weinheim, Germany, 2008.

Since the first reports of OLEDs (for example Tang et al., Appl. Phys. Lett. 51 (1987) 913), these devices have been developed further, in particular with respect to the emitter materials employed, where, in particular, so-called triplet emitters or also other phosphorescent emitters are of interest.

The crucial factor for the construction of highly effective OLEDs are the light-emitting materials (emitter molecules) used. These can be produced in various ways, using purely organic molecules or organometallic complex compounds. It can be shown that the light yield of the OLEDs comprising organometallic substances, so-called triplet emitters, can be significantly greater than for purely organic materials. Owing to this property, the further development of organometallic materials is of crucial importance.

Particularly high efficiency of the device can be achieved using organo-metallic complexes having a high emission quantum yield (emission from the lowest triplet states to the singlet ground states). These materials are frequently known as triplet emitters or phosphorescent emitters.

Compared with conventional technologies, such as, for example, liquid-crystal displays (LCDs), plasma displays or cathode ray tubes (CRTs), OLEDs have numerous advantages, such as, for example, a low operating voltage, a thin structure, highly efficiently self-illuminating pixels, high contrast and good resolution, as well as the possibility to display all colours. Furthermore, an OLED emits light on application of an electrical voltage instead of only modulating it. Whereas numerous applications have already been achieved by OLEDs and new areas of application have also been opened up, there is still a demand for improved OLEDs and in particular for improved triplet emitter materials. In the emitters to date, problems arise, in particular, with the long-term stability, the thermal stability and the chemical stability to water and oxygen. Furthermore, many emitters only exhibit low sublimability. In addition, important emission colours are often not available with emitter materials known to date. Furthermore, high efficiencies often cannot be achieved at the same time as high current densities or high luminous densities. Finally, there are problems in the case of many emitter materials with respect to manufacturing reproducibility. A problem which is furthermore often observed is the formation of undesired aggregates.

Besides the chromophoric unit, many emitter complexes also contain auxiliary ligands (auxiliary, ancillary, spectator ligands). For the purposes of this application, an auxiliary ligand is taken to mean a ligand which is itself not directly involved in the electronic transitions, but modulates them in a variety of ways. In some cases, the auxiliary ligands have a major influence on the energetic position of the states involved in the transitions, in particular those in which the metal centres are involved. Their influence can frequently be correlated well with their ligand properties, in particular their ratio between σ donor and π acceptor ability, but also with steric considerations. Systematic studies of [Ir(ppy)$_2$L$_2$] complexes (ppy=2-phenylpyridine, L=auxiliary ligand) confirm these trends (J. Li, P. I. Djurovich, B. D. Alleyne, M. Yousufuddin, N. N. Ho, J. C. Thomas, J. C. Peters, R. Bau, M. E. Thompson, Inorg. Chem. 2005, 44, 1713; J. Li, P. I. Djurovich, B. D. Alleyne, I. Tsyba, N. N. Ho, R. Bau, M. E. Thompson, Polyhedron 2004, 23, 419).

Examples of auxiliary ligands used to date are acetylacetonate 1 and its nitrogen homologues 2, pyrazolylborate 3, picolinate 4 and bis(phosphino-methylene)borates 5, as well as compounds which are very generally derived from pyrrole 6. However, the latter are involved in the lowest electronic transition in many emitter complexes.

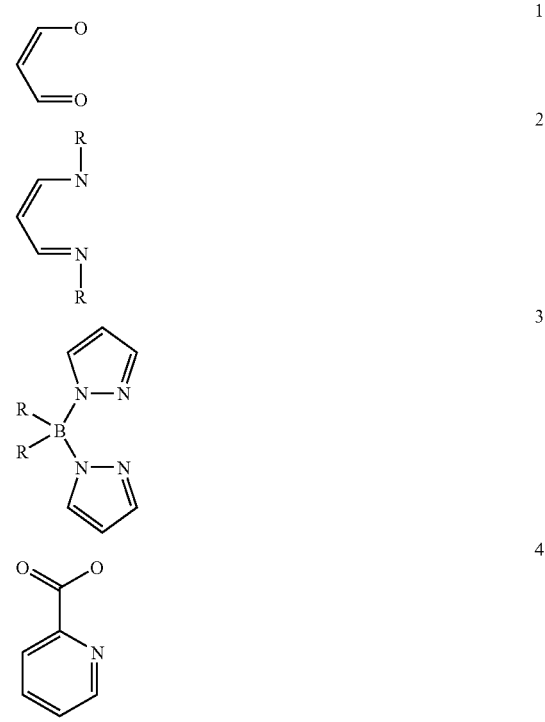

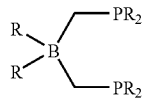

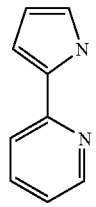

An object of the present invention was therefore to provide novel emitter materials, in particular for OLEDs, and novel light-emitting devices which at least partially overcome the disadvantages of the prior art and in which, in particular, the formation of undesired aggregates is reduced. This object is achieved in accordance with the invention by the use of metal complexes which contain at least one carborane-containing ligand.

To date, numerous non-luminescent transition-metal complexes containing nido-carborane-diphosphine ligands have been synthesised. These complexes contained the following central ions: $Pd^{2+}$, $Ni^{2+}$, $Pt^{2+}$, $Ag^+$, $Ru^{2+}$, $Cu^+$, $Ru^{2+}$ and $Rh^+$ (F. Teixidor, C. Viñas, M. M. Abad, F. Teixidor, R. Sillanpää, *J. Organomet. Chem.*, 1996, 509, 139, C. Viñas, M. M. Abad, F. Teixidor, R. Sillanpää, R. Kivekäs, *J. Organomet. Chem.*, 1998, 555, 17, D. Zhang, J. Dou, D. Li, D. Wang, *Inorg. Chim. Acta*, 2006, 359, 4243, O. Crespo, M. C. Gimeno, P. G. Jones, A. Laguna, *J. Chem. Soc., Dalton Trans.*, 1996, 4583) and non-chromophore ligands, for example Cl, triphenylphosphine, isonitriles, etc. In addition, photoluminescent Au clusters (M. J. Calhorda, O. Crespo, M. C. Gimeno, P. G. Jones, A. Laguna, J.-M. López-de-Luzuriaga, J. L. Perez, M. A. Ramón, L. F. Veiros, *Inorg. Chem.*, 2000, 39, 4280) and Au(I) complexes (O. Crespo, M. C. Gimeno, P. G. Jones, A. Laguna, *Inorg. Chem.*, 1996, 35, 1361, O. Crespo, M. C. Gimeno, P. G. Jones, A. Laguna, J.-M. López-de-Luzuriaga, M. Monge, J. L. Perez, M. A. Ramón, *Inorg. Chem.*, 2003, 42, 2061) containing nido-carborane-diphosphine ligands have also been synthesised. In the latter case, i.e. for complexes of the Au(I) (nido-carborane-diphosphine) (PPh₃) type, however, it was noted in the cited article that the nido-carborane-diphosphine ligands are involved in the lowest electronic transitions (luminescence from an intraligand-excited state). Consequently, this case does not involve auxiliary ligands, but instead the nido-carborane-diphosphines act as chromophore ligands here. The Au complexes discussed in Crespo do not contain a chromophore ligand in addition to the nido-carborane-diphosphine ligands. Furthermore, the Au complexes discussed in Crespo are not very chemically stable since Au(I) usually has only two coordinations, but is triply coordinated in these complexes. The Ag complexes discussed by Crespo do not emit, i.e. cannot be used, for example, for OLED applications. $Cu^{2+}$, $Ni^{2+}$ and $Zn^{2+}$ complexes containing the ligand 1c (R=Ph), but no chromophore ligands, have been reported briefly (J. Dou, D. Zhang, D. Li, D. Wang, Eur. J. Inorg. Chem., 2007, 53). Organic electronic devices which comprise these metal complexes are not known.

The invention therefore relates to an organic electronic device comprising at least one metal complex, characterised in that the metal complex contains at least one ligand of the formula (I)

$$[7,8-(ER_2)_2-7,8-C_2B_9(R^1)_{10}]$$   formula (I)

in which:
E is, identically or differently on each occurrence, P, As, Sb, N or a P=O, P=S, As=O or As=S group;
R is, identically or differently on each occurrence, H, deuterium, F, Cl, Br, I, $N(R^2)_2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems; two or more of these substituents R here may also form a mono- or polycyclic, aliphatic, aromatic and/or benzo-fused ring system with one another;
$R^1$ is, identically or differently on each occurrence, H, OH or a $C_1$-$C_{30}$-alkoxy group;
$R^2$ is on each occurrence, identically or differently, H, F or an aliphatic, aromatic and/or heteroaromatic hydrocarbon radical having 1 to 20 C atoms, in which, in addition, one or more H atoms may be replaced by F; two or more substituents $R^2$ here may also form a mono- or polycyclic, aliphatic, aromatic and/or benzo-fused ring system with one another.

An organic electronic device is taken to mean an electronic device which comprises an anode, a cathode and at least one layer, where this layer comprises at least one organic compound. The organic electronic device according to the invention thus comprises an anode, a cathode and at least one layer which comprises at least one metal complex containing a ligand of the formula (I) given above. Preferred organic electronic devices here are selected from the group consisting of organic electroluminescent devices (=organic light-emitting diodes, OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photo-receptors, organic field-quench devices (O-FQDs), light-emitting electro-chemical cells (LECs), organic laser diodes (O-lasers) or OLED sensors (gas and vapour sensors which are not hermetically screened from the outside), comprising, in at least one layer, at least one metal complex containing a ligand of the formula (I) given above. Particular preference is given to organic electroluminescent devices.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc. For the purposes of this invention, a cyclic carbene is a cyclic group which bonds to the metal via a neutral C atom. The cyclic group here may be saturated or unsaturated. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group for the purposes of this invention.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

For the purposes of the present invention, a $C_1$- to $C_{40}$-alkyl group, in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. A $C_1$- to $C_{40}$-alkoxy group is preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic group via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The ligand of the formula (I) is preferably employed as auxiliary ligand, and the metal complex is preferably an emitter complex. It has been found that compounds of the formula (I) are eminently suitable as auxiliary ligands in emitter complexes. Compounds of the formula (I) are bidentate ligands which have, in particular, high stability and high rigidity. The compounds of the formula (I) are singly negatively charged ligands. Furthermore, the compounds of the formula (I) are ligands which cause steric hindrance.

The rigidity of the ligand of the formula (I) results in a reduction in radiationless deactivation of the excited state and therefore has a particularly favourable effect on the emission quantum yield. The choice of auxiliary ligands is, from photophysical perspectives, subject to the restriction that they must not themselves have any low-lying electronic states which result in direct involvement in the transitions. For the purposes of this application, an auxiliary ligand is therefore defined as a ligand which is not directly involved in the electronic transitions of the complex. Otherwise, these ligands would no longer play the role of an auxiliary ligand. For use in OLEDs, further requirements of the ligands arise in addition. The neutrality of the substances used in OLEDs, including the triplet emitter, is advantageous during operation of the device since neutral molecules have no mobility in an external electric field. Neutrality of the complexes is also demanded since the OLED devices which have currently been developed the furthest are produced by vacuum sublimation. This is also important in the case of devices processed by wet-chemical methods, since neutral complexes generally have greater solubility in the most frequently used organic solvents. The ligands of the formula (I) are eminently suitable since they are singly charged, bidentate and chemically and thermally stable, have a high ligand-field strength, do not absorb light in the visible region and do not have any low-lying triplet states.

Depending on the atom or atom group E, the ligands of the formula (I) can be divided into three particular groups:

Group 1: Ligands in which both symbols E stand for P, As, Sb or N:

| | |
|---|---|
| $[7,8-(PR_2)_2-7,8-C_2B_9H_{10}]$ | formula (Ia) |
| $[7,8-(AsR_2)_2-7,8-C_2B_9H_{10}]$ | formula (Ia') |
| $[7,8-(SbR_2)_2-7,8-C_2B_9H_{10}]$ | formula (Ia'') |
| $[7,8-(NR_2)_2-7,8-C_2B_9H_{10}]$ | formula (Ia''') | and corresponding ligands in which the two symbols E are different and are selected from P, As, Sb and N.

Group 2: Ligands in which one symbol E stands for a P=O, P=S, As=O or As=S group and the other symbol E is selected from P, As, Sb or N:

| | |
|---|---|
| $[7-(O=PR_2)-8-(ER_2)-7,8-C_2B_9H_{10}]$ | formula (Ib) |
| $[7-(S=PR_2)-8-(ER_2)-7,8-C_2B_9H_{10}]$ and | formula (Ib') |
| $[7-(O=AsR_2)-8-(ER_2)-7,8-C_2B_9H_{10}]$ | formula (Ib'') |
| $[7-(S=AsR_2)-8-(ER_2)-7,8-C_2B_9H_{10}]$ | formula (Ib''') |

Group 3: Ligands in which both symbols E stand for a P=O, P=S, As=O or As=S group:

[7,8-(O=PR$_2$)$_2$-7,8-C$_2$B$_9$H$_{10}$]  formula (Ic)

[7,8-(S=PR$_2$)$_2$-7,8-C$_2$B$_9$H$_{10}$]  formula (Ic')

[7,8-(S=AsR$_2$)$_2$-7,8-C$_2$B$_9$H$_{10}$]  formula (Ic'')

[7,8-(S=AsR$_2$)$_2$-7,8-C$_2$B$_9$H$_{10}$]  formula (Ic''')

and corresponding ligands in which the two symbols E are different and are selected from P=O, P=S and As=O.

The bulky auxiliary ligands of the formula (I) according to the invention are preferably singly negatively charged, bidentate nido-carborane-diamines, nido-carborane-diphosphines, nido-carborane-diarsines, nido-carboranedistibines, or nido-carborane-oxodiphosphines, nido-carborane-thiodiphosphines, nido-carborane-oxodiarsines, nido-carborane-dioxodiphosphines, nido-carborane-dithiodiphosphines, nido-carborane-dioxodiarsines (cf. FIG. 2), i.e. the formula 7,8-C$_2$B$_9$H$_{10}$ stands for a nido-carborane which contains carbon in positions 7 and 8, where the coordinating groups E are likewise bonded in positions 7 and 8.

The metal complexes as can preferably be employed in the organic electronic device are described in greater detail below.

Preference is given to complexes of the formula (II)

M(E∩E)$_x$(A∩A$^{n-}$)$_y$(L)$_z$  formula (II)

in which:
M is a metal, preferably a transition metal, in particular selected from W, Re, Os, Ir, Pt, Ru, Rh or Cu, or a lanthanide,
(E∩E) is a compound of the formula (I) given above,
(A∩A$^{n-}$) is a bi- or polydentate ligand,
L is a mono- or polydentate ligand,
x is 1, 2 or 3,
y is 0, 1, 2 or 3, in particular 1, 2 or 3, and particularly preferably 1 or 2,
z is 0, 1, 2 or 3,
n is 0, 1 or 2.

For the purposes of this invention, a ligand is defined as follows: for y not equal to 0, the complexes of the formula (II) according to the invention contain two functional types of ligand. The singly negatively charged ligand (ENE) which causes steric hindrance can take on two functions: it ensures charge equalisation and improves the photophysical properties of the complex. The second ligand (A∩A$^{n-}$) is the actual chromophoric unit and is thus ultimately responsible for the luminescence. Under certain conditions, it may be advantageous also to introduce a further ligand L in order, for example, to achieve charge neutrality or to achieve coordinative saturation of the metal centre. These ligands L can cause significantly less steric hindrance than the bulky auxiliary ligand (ENE), but should preferably, like the latter, likewise have no low-lying electronic states. In particular, L should not be involved in the electronic transition. Furthermore, it is advantageous if L is able to stabilise the metal complex. L may be neutral or negatively charged, in particular singly negatively charged, and mono- or polydentate, in particular mono- or bidentate. The ligand L is preferably an auxiliary ligand which does not cause much steric hindrance, i.e. it is preferably not involved in the electronic transitions of the complex on emission. L can be selected from the large number of ligands which are available from complex chemistry. L here may be mono-, bi- or tridentate or also polydentate. The choice of a suitable ligand L will ultimately depend on the corresponding central metal. The lowest π* orbitals of the ligand L are preferably higher than those of the (A∩A$^{n-}$) chromophore ligand. The ligands L may also be linked, i.e. they may be constituents of a bidentate ligand (L-L'). The relative position of the lowest π* orbitals can be determined by UV-vis spectroscopy or by UPS (ultraviolet photoelectron spectroscopy).

The ligands L are preferably neutral, monoanionic, dianionic or trianionic ligands, particularly preferably neutral or monoanionic ligands. They are preferably monodentate, bidentate or tridentate, i.e. have one, two or three coordination sites.

Preferred neutral, monodentate ligands L are selected from carbon monoxide, nitrogen monoxide, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, nitriles, amines, such as, for example, trimethylamine, triethylamine, morpholine, imines, phosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsinine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, thioethers and nitrogen-containing heterocyclic compounds, such as, for example, pyridine, 2,4,6-trimethylpyridine, pyridazine, pyrazine, pyrimidine, triazine.

Preferred monoanionic, monodentate ligands L are selected from hydride, deuteride, the halides F, Cl, Br and I, alkylacetylides, such as, for example, methyl-C≡C$^-$, tert-butyl-C≡C$^-$, arylacetylides, such as, for example, phenyl-C≡C$^-$, cyanide, cyanate, isocyanate, thiocyanate, isothiocyanate, nitrate, nitrite, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, and anionic, nitrogen-containing heterocyclic compounds, such as pyrrolide, imidazolide, pyrazolide, alkyl groups, aryl groups, such as, for example, phenyl or pentafluorophenyl. The alkyl groups in these groups are preferably C$_1$-C$_{20}$-alkyl groups, particularly preferably C$_1$-C$_{10}$-alkyl groups, very particularly preferably C$_1$-C$_4$-alkyl groups. An aryl group is also taken to mean heteroaryl groups. These groups are as defined above.

Preferred di- or trianionic ligands L are O$^{2-}$, S$^{2-}$, nitrenes, which result in coordination in the form R—N=M, where R generally stands for a substituent, or N$^{3-}$.

Preferred neutral or mono- or dianionic bidentate or polydentate ligands L are selected from diamines, such as, for example, ethylenediamine, N,N,N',N'-tetramethylethylenediamine, propylenediamine, N,N,N',N'-tetra-methylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino)ethyl]-pyridine, 2-[1-(ethylimino)ethyl]pyridine, 2-[1-(isopropylimino) ethyl]pyridine, 2-[1-(tert-butylimino)ethyl]pyridine, dimines, such as, for example, 1,2-bis(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino)ethane, 1,2-bis(2,6-diisopropylphenylimino)ethane, 1,2-bis(2,6-di-ter-butylphenylimino)ethane, 2,3-bis(phenylimino)butane, 2,3-bis(2-methylphenylimino)butane, 2,3-bis(2,6-diisopropylphenylimino)butane, 2,3-bis(2,6-di-tert-butylphenylimino)butane, heterocyclic compounds containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands L are borates of nitrogen-containing heterocyclic compounds, such as, for example, tetrakis(1-imidazolyl) borate and tetrakis(1-pyrazolyl) borate.

The number and charges of the ligands in the complex of the formula (II) are preferably selected so that they compensate for the charge of the metal, so that the complex of the formula (II) overall is uncharged, i.e. is electrically neutral.

The indices x, y and z here are selected so that the coordination number at the metal M corresponds overall, depending on the metal, to the usual coordination number for this metal. For main-group and transition metals, this is usually the coordination number 4, 5 or 6, depending on the metal. For lanthanides, coordination numbers of up to 12 are also known. It is generally known that metal coordination compounds have different coordination numbers, i.e. bind a different number of ligands, depending on the metal and on the oxidation state of the metal. Since the preferred coordination numbers of metals or metal ions in various oxidation states belong to the general expert knowledge of the person skilled in the art in the area of organometallic chemistry or coordination chemistry, it is simple for the person skilled in the art to choose the number of ligands suitably, depending on the metal and its oxidation state and depending on the precise structure of the ligands.

In accordance with the invention, $(A \cap A''^-)$ represents a bidentate or polydentate ligand. The formation of a chelate complex containing this ligand increases the stability of the complex compared with an only singly bonded ligand. $(A \cap A''^-)$ is preferably a chromophore ligand, i.e. a ligand which is itself involved in the electronic transitions of the complex on emission (fluorescence or phosphorescence). $(A \cap A''^-)$ is preferably a bidentate ligand. This ligand is neutral or negatively charged, in particular singly negatively charged. $(A \cap A''^-)$ is preferably bonded to the metal in the complex according to the invention through a carbon atom and/or through a nitrogen atom. The carbon atom may also be a carbene. The ligand $(A \cap A''^-)$ preferably encompasses aromatic or heteroaromatic groups and in particular two aromatic or heteroaromatic groups (Ar-Ar). The ligand $(A \cap A''^-)$ in the complex furthermore preferably has at least one direct metal-carbon bond.

Preferred ligands $(A \cap A''^-)$ are bidentate monoanionic ligands which, with the metal, form a cyclometallated five-membered ring having at least one metal-carbon bond. These are, in particular, ligands as are generally used in the area of phosphorescent metal complexes for organic electroluminescent devices, i.e. ligands of the phenylpyridine, naphthylpyridine, phenylquinoline, phenylisoquinoline, etc., type, each of which may be substituted by one or more radicals R. A multiplicity of such ligands is known to the person skilled in the art in the area of phosphorescent electroluminescent devices, and he will be able, without an inventive step, to select further ligands of this type as ligand $(A \cap A''^-)$ for compounds of the formula (II).

In a preferred embodiment of the invention, the group $(A \cap A''^-)$ is composed of two aryl or heteroaryl groups having 5 to 40 aromatic ring atoms, which may be identical or different on each occurrence, which may be substituted by one or more radicals R and/or which may also contain an exocyclic donor atom. The groups R here are defined as above. Preferred aryl and heteroaryl groups are benzene, 2-phenol, 2-thiophenol, naphthalene, anthracene, phenanthrene, pyridine, quinoline, isoquinoline, pyrazine, quinoxaline, pyrimidine, pyridazine, triazine, pyrrole, indole, imidazole, furan, benzofuran, benzimidazole, pyrazole, triazole, oxazole, thiazole, thiophene, benzothiophene, benzoxazole or benzothiazole, each of which may be substituted by one or more radicals R. Depending on the group, the above-mentioned groups are neutrally coordinating groups, for example pyridine, which bonds via a neutral N atom, or anionically coordinating groups, for example benzene, thiophene and phenol, which bond via a negatively charged C atom or O atom. Further preferred coordinating groups are unsaturated or saturated cyclic Arduengo carbenes, in particular unsaturated cyclic Arduengo carbenes, each of which may be substituted by one or more radicals R, and alkenes or imines, each of which may be substituted by one or more radicals R.

Generally suitable as ligand $(A \cap A''^-)$ is, in particular, the combination of two groups, as depicted by the following formulae, where one group bonds via a neutral nitrogen atom or carbene atom and the other group bonds via a negatively charged carbon atom or a negatively charged nitrogen atom. The ligand $(A \cap A''^-)$ can then be formed from the groups of the formulae depicted by two of these groups bonding to one another, in each case at the position denoted by #. In these formulae, * in each case indicates the position in which the ligand bonds to the metal. It is preferred here for a neutrally coordinating group and an anionic group to be bonded to one another.

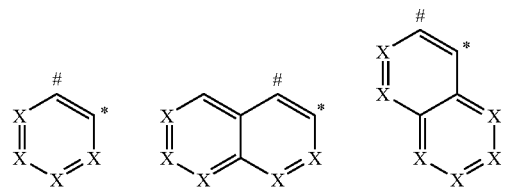

-continued

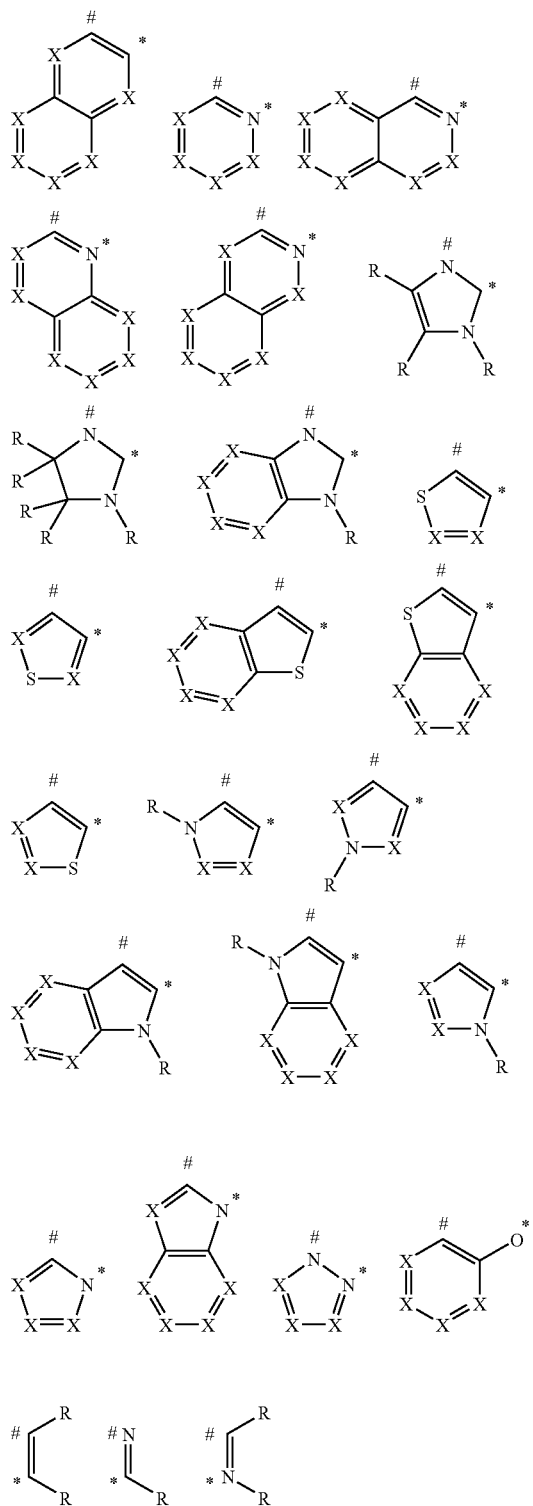

X here stands, identically or differently on each occurrence, for CR, where R has the above-mentioned meaning, or for N, with the proviso that a maximum of three symbols X in each group stand for N. Preferably a maximum of two symbols X in each group stand for N, particularly preferably a maximum of one symbol X in each group stands for N, very particularly preferably all symbols X stand for CR.

Thus, suitable ligands (A∩A⁻) are, for example, ligands of the following structure:

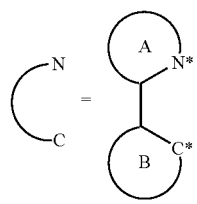

where the units A and B can consist of five- or six-membered rings or are open-chain. The units A and B in this structure stand, for example, for

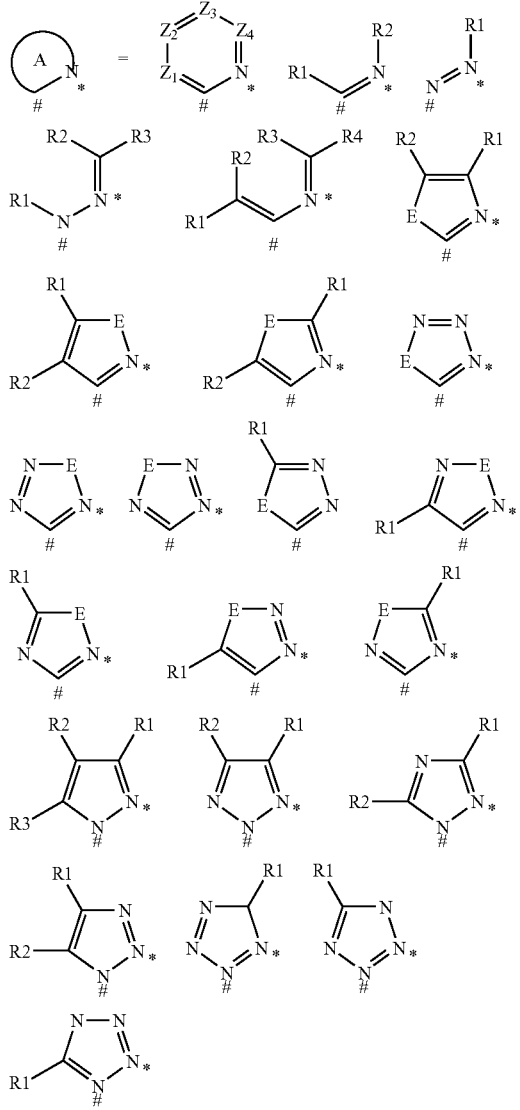

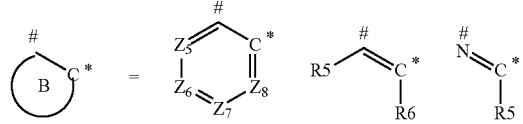

-continued

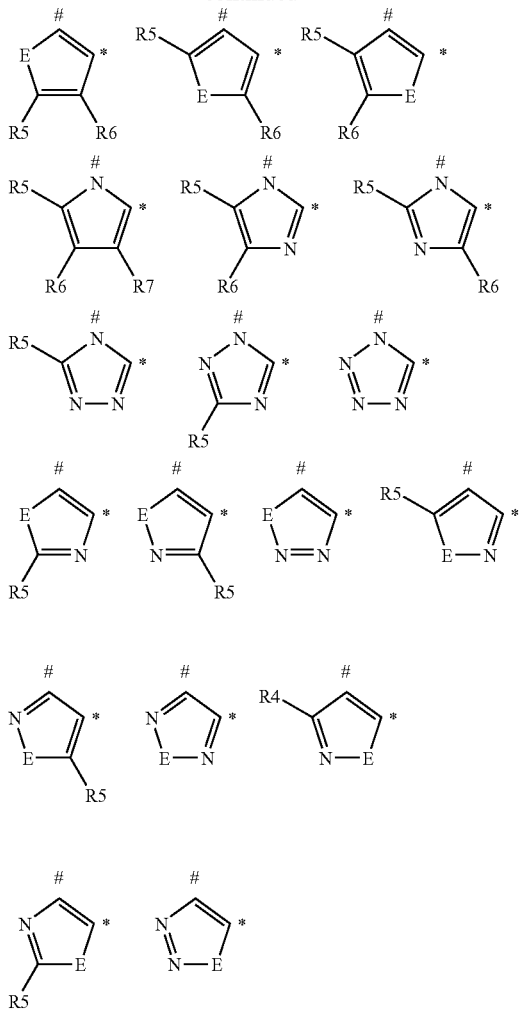

in which R has the same meaning as described above, and furthermore:

E is O, S or NR,

R1 to R7 have the same meaning as R,

Z1 to Z8 are, identically or differently on each occurrence, C—R or N,

* denotes the atom which bonds to the complex, and represents the atom which is bonded to the second unit.

Examples of preferred ligands (A∩A⁻) are depicted below:

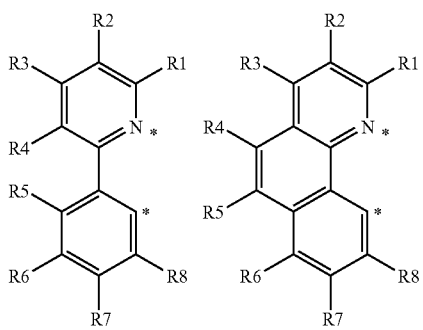

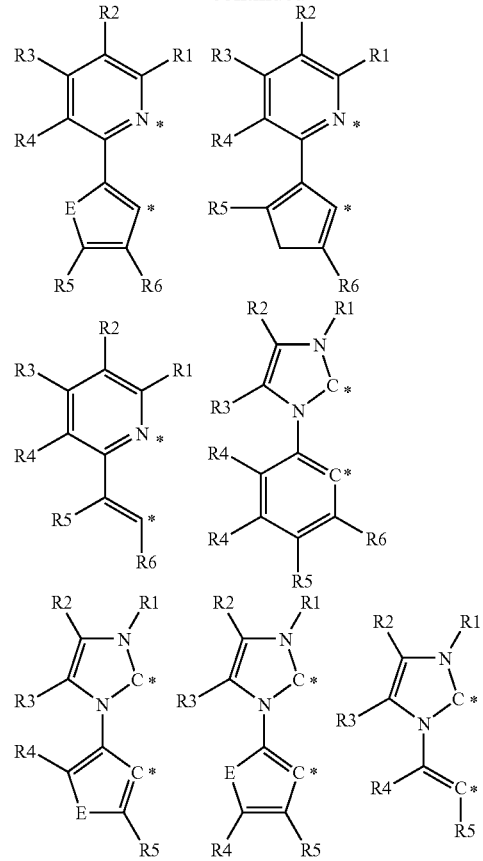

where the symbols and indices used have the same meaning as described above.

Preference is furthermore given to complexes of the formula (II) in which (A∩A⁻) is represented by the following formula:

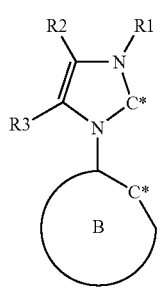

where B can consist of a 5- or 6-membered ring or can be open-chain, and R1, R2 and R3 each, independently, have the same meaning as R, as described above for formula (I). The unit B here is preferably selected from the following formulae:

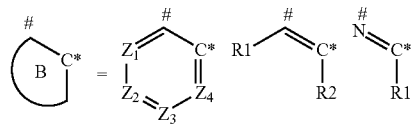

-continued

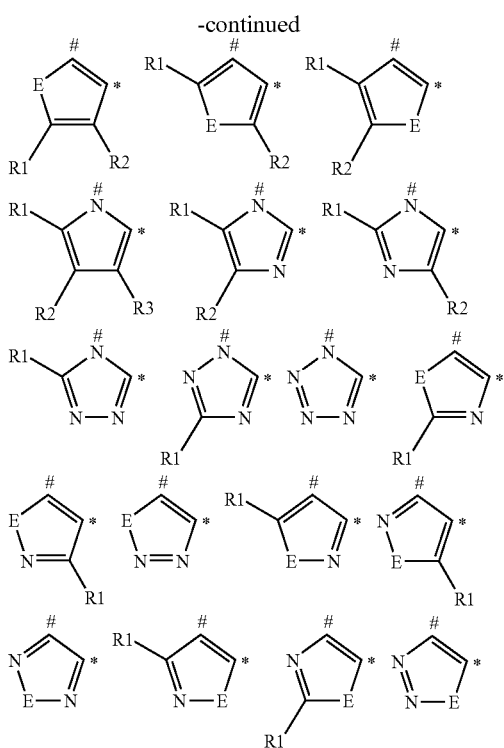

in which R has the same meaning as described above, and furthermore:

E is O, S or NR,

R1 to R3 have the same meaning as R,

Z1 to Z4 are, identically or differently on each occurrence, C—R or N,

* denotes the atom which bonds to the complex, and represents the atom which is bonded to the second unit.

For example, (A∩A⁻) stands for

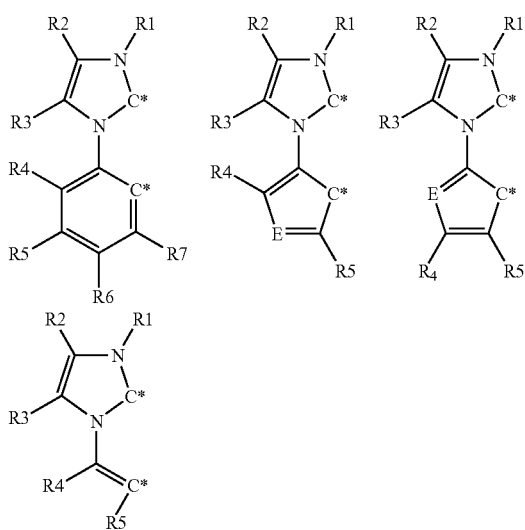

in which R, R1, R2, R3 and E have the same meaning as described above, and furthermore R4, R5 and R6 have the same meaning as defined above for R. * denotes the atom which bonds to the complex.

Preference is given to complexes of the formula (II) selected from M(E∩E)(A∩A''ⁿ⁻)₂, M(E∩E)₂(A∩A''ⁿ⁻) or M(E∩E)(A∩A''ⁿ⁻)(L)₂, where M is preferably Os(II), Ir(III), Ru(II), Re(I), Pt(IV) or W(0), in particular Ir(III). Particular preference is given to complexes of the formula (II) selected from Pt$^{II}$(E∩E)(A∩A⁻), Ir$^{III}$(E∩E)₂(A∩A⁻), Ir$^{III}$(E∩E)(A∩A⁻)₂, Rh$^{III}$(E∩E)ₙ(A∩A''ⁿ⁻), Rh$^{III}$(E∩E)(A∩A⁻)₂, Os$^{II}$(E∩E)(A∩A⁻)L₂ and Ru$^{II}$(E∩E)(A∩A⁻)L₂, where (A∩A⁻) in each case stands for one of the preferred ligands mentioned above.

Further preferred neutral ligands (A∩A) are the ligands (N∩N) mentioned below.

A further preferred embodiment of the invention comprises the complexes of the following formulae (III), (IV), (V) and (VI),

| | |
|---|---|
| M(III)(E∩E)₃ | formula (III) |
| M(III)(E∩E)₃(L)$_z$ | formula (IV) |
| M(II)(E∩E)₂(L)$_z$ | formula (V) |
| M(III)(E∩E)₃(N∩N)(L)$_z$ | formula (VI) | in which:

(N∩N) is a bidentate ligand which coordinates to the metal via two nitrogen atoms;

M(III) is a trivalent lanthanoid cation, for example Ce(III), Pr(III), Nd(III), Pm(III), Sm(III), Eu(III), Gd(III), Tb(III), Dy(III), Ho(III), Er(III), Tm(III), Yb(III), Lu(III), M(II) is a divalent lanthanoid cation, for example Sm(II), Eu(II), Tm(II) or Yb(II), (E∩E) is a ligand of the formula (I), in particular of the formula (Ic), and L is a mono- or polydentate ligand.

L is preferably selected from the ligands L as mentioned above for the complexes of the formula (II).

It is known that phosphine oxides are eminently suitable as ligands for lanthanoid cations. The combination of the phosphine oxide group with the nido-carborane unit produces the singly negatively charged ligand of the formula (Ic), which causes considerable steric hindrance and is capable of screening the coordination sphere of the central atom in an excellent manner and thus results in extremely stable and at the same time neutral complexes. This good screening avoids the interference of the metal-centred, electronic transitions and therefore reduces radiationless deactivation, which in turn results in high emission quantum yields.

It is precisely the combination of the versatile phosphine and phosphine oxide groups and a very rigid, singly negatively charged nido-carborane skeleton that makes these ligands ideal auxiliary ligands for use in neutral emitter complexes. In particular, the high rigidity and bulk of these ligands facilitate stable neutral metal complexes having high emission quantum yields (also in layers which consist of 100% of the complex material).

The ligand (N∩N) should preferably not have excessively high-lying triplet states. (N∩N) likewise preferably stands for an α-diimine ligand. In a preferred embodiment of the invention, the ligand (N∩N) has the following structure:

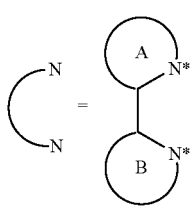

in which the groups A and B represent five- or six-atom rings or are open-chain. The groups A and B here are preferably selected from the groups depicted below:

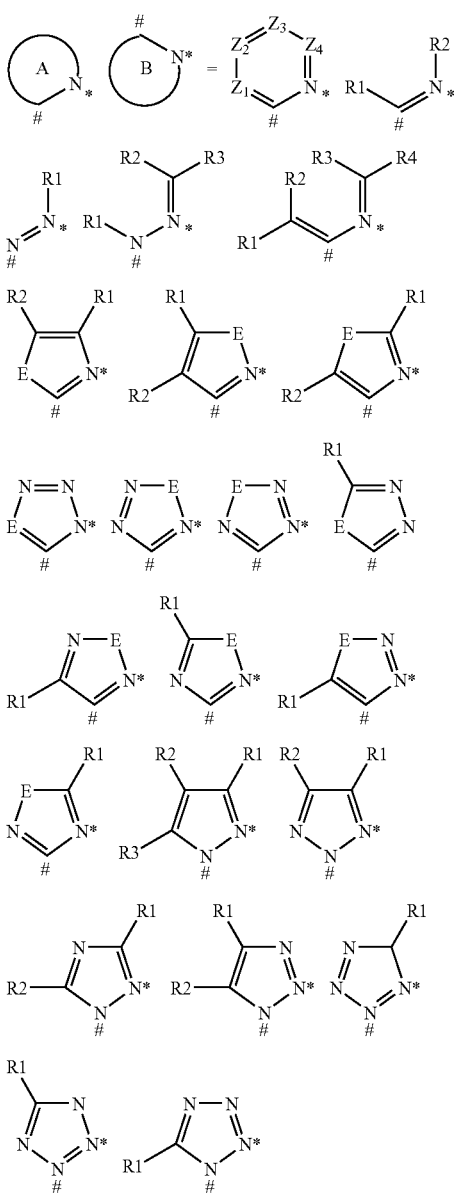

in which the symbols E, R, R1 to R4 and Z1 to Z4 have the same meaning as described above, * denotes the atom which bonds to the complex, and # represents the atom which is bonded to the second unit.

Ligands (N∩N) are selected, for example, from the following formulae:

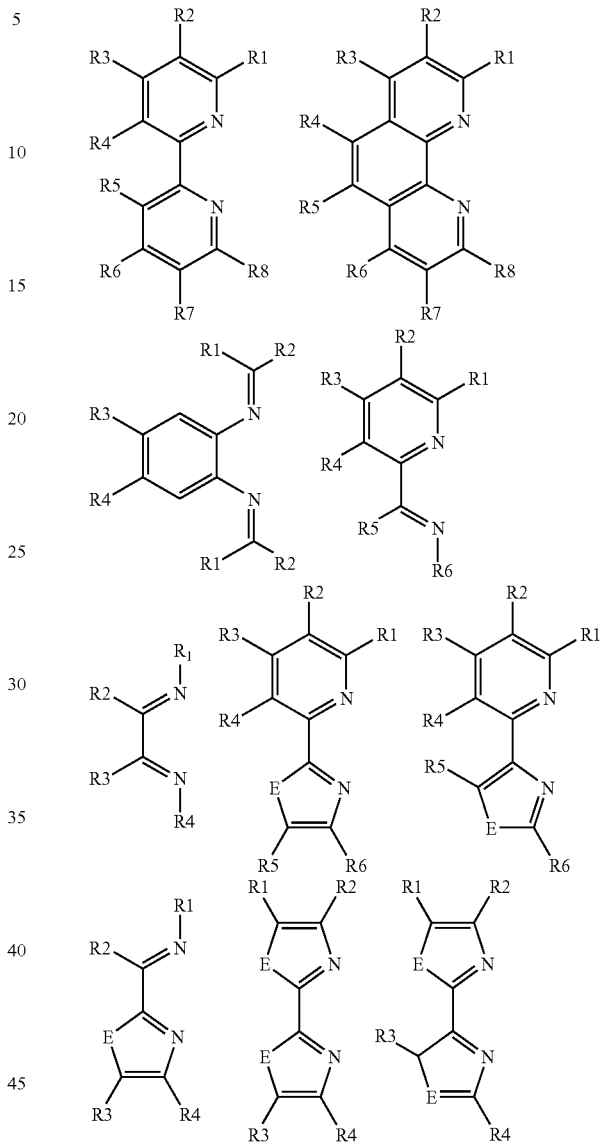

where the symbols have the same meaning as described above.

Examples of preferred ligands (N∩N) are the ligands depicted below:

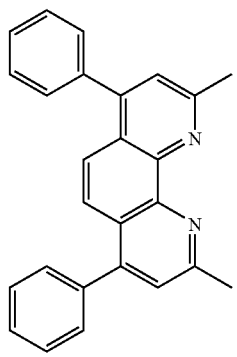

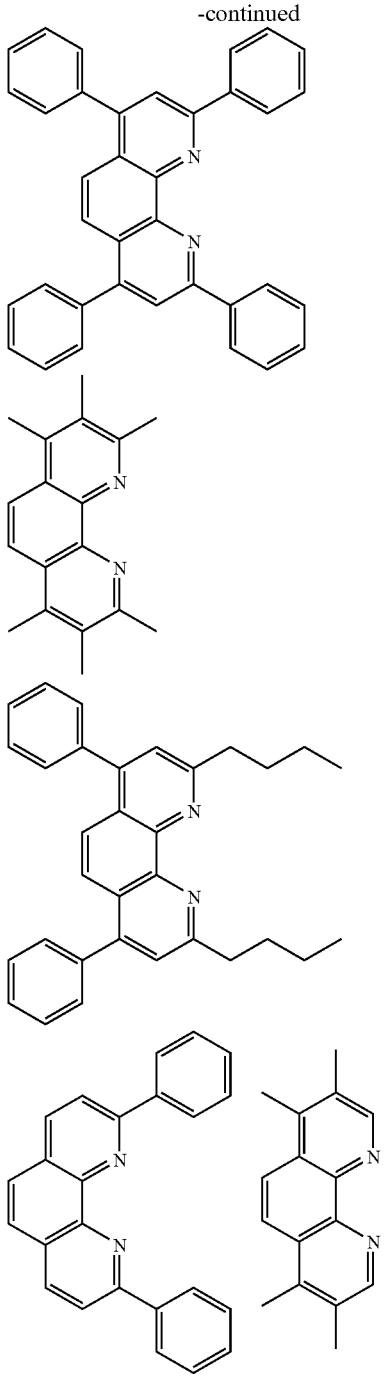

These are also particularly suitable for use in Cu(I) complexes.

Examples of complexes of the formula (II) according to the invention are complexes of the Re$^I$(CO)$_2$(E∩E)(N∩N), Ru$^{II}$(E∩E)$_2$(N∩N), Cu$^I$(E∩E)(N∩N), Rh$^I$(E∩E)(N∩N), Os$^{II}$(E∩E)$_2$(N∩N), Os$^{II}$(CO)Cl(E∩E)(N∩N), Os$^{II}$(CO)Br(E∩E)(N∩N), Os$^{II}$(CO)(CN)(E∩E)(N∩N), Os$^{II}$(CO)(SCN)(E∩E)(N∩N), Ru$^{II}$(CO)(Cl)(E∩E)(N∩N), Ru$^{II}$(CO)(Br)(E∩E)(N∩N), Ru$^{II}$(CO)(CN)(E∩E)(N∩N), Ru$^{II}$(CO)(SCN)(E∩E)(N∩N), Ru$^{II}$(Li)(L$^1$)(L$^2$)(E∩E)(N∩N), Os$^{II}$(L$^1$)(L$^2$)(E∩E)(N∩N) and Ir$^I$(E∩E$^-$)(N∩N) type, in which L$^1$ and L$^2$ each, independently, represent CO, CN$^-$, SCN$^-$, halogen, pyridine, nitrile or isonitrile.

In a preferred embodiment of the invention, the substituent R in the ligand of the formula (I) is, identically or differently on each occurrence, H, deuterium, N(R$^2$)$_2$, a straight-chain alkyl, alkoxy or thioalkoxy group having 1 to 20 C atoms or a branched or cyclic alkyl, alkoxy or thioalkoxy group having 3 to 20 C atoms, each of which may be substituted by one or more radicals R$^2$, where one or more non-adjacent CH$_2$ groups may be replaced by R$^2$C=CR$^2$ or C≡C and where one or more H atoms may be replaced by F, or an aromatic or heteroaromatic ring system having 5 to 30 aromatic ring atoms, which may in each case be substituted by one or more radicals R$^2$, or an aryloxy or heteroaryloxy group having 5 to 30 aromatic ring atoms, which may be substituted by one or more radicals R$^2$, or a combination of these systems; two or more of these substituents R here may also form a mono- or polycyclic, aliphatic, aromatic and/or benzo-fused ring system with one another. In a particularly preferred embodiment of the invention, the substituent R in the ligand of the formula (I) is, identically or differently on each occurrence, H, a straight-chain alkyl or alkoxy group having 1 to C atoms, in particular having 1 to 6 C atoms, or a branched or cyclic alkyl or alkoxy group having 3 to 10 C atoms, in particular having 3 to 6 C atoms, or an aromatic or heteroaromatic ring system having 5 to 14 aromatic ring atoms, each of which may be substituted by one or more radicals R$^2$, or an aryloxy or heteroaryloxy group having 5 to 14 aromatic ring atoms, which may be substituted by one or more radicals R$^2$, or a combination of these systems; two or more of these substituents R here may also form a mono- or polycyclic, aliphatic, aromatic and/or benzo-fused ring system with one another.

In a further preferred embodiment of the invention, the substituent R$^1$ in ligands of the formula (I) is equal to H.

In a further preferred embodiment of the invention, the substituent R on the ligand (A∩A$^{n-}$) is selected, identically or differently on each occurrence, from H, deuterium, F, Cl, Br, I, N(R$^2$)$_2$, a straight-chain alkyl or alkoxy group having 1 to 10 C atoms or a branched or cyclic alkyl or alkoxy group having 3 to 10 C atoms, each of which may be substituted by one or more radicals R$^2$, where one or more non-adjacent CH$_2$ groups may be replaced by R$^2$C=CR$^2$, C≡C and where one or more H atoms may be replaced by F, or an aromatic or heteroaromatic ring system having 5 to 20 aromatic ring atoms, which may in each case be substituted by one or more radicals R$^2$, or a combination of these systems; two or more of these substituents R here may also form a mono- or polycyclic, aliphatic, aromatic and/or benzo-fused ring system with one another. The systems substituted by Cl, Br or I are particularly suitable as intermediates for the synthesis of derivatives of these compounds.

The complexes of the formula (II) contain a central atom which is a metal. M is preferably a single metal ion or metal atom.

In a first embodiment of the complexes, M is, in particular, a transition metal and is preferably selected from Pt, Rh, Ir, Re, Ru, Cu, Os or W. The central atom is preferably in the form of Pt(II), Pt(IV), Rh(II), Rh(I), Ir(I), Ir(III), Re(I), Ru(II), Cu(I), Rh(I), Os(II), W(0), W(II), W(III) or W(VI), i.e. in the form of an atom or a singly or doubly or triply positively charged ion. The central atoms are particularly preferably Pt(II), Ir(III) or Cu(I).

M is preferably not Ag or Au and in particular not Au.

In particular for such complexes, y is preferably 1, 2 or 3, particularly preferably 1 or 2, i.e. the complexes contain at least one chromophore ligand (A∩A$^{n-}$). The complex then preferably has at least one direct metalcarbon bond to the ligand (A∩A$^{n-}$).

In a further preferred embodiment, M represents a lanthanoid cation, in particular in the preferred complexes of the formulae (III), (IV), (V) and (VI).

For complexes of the formulae (III), (IV) and (VI), M is preferably a trivalent lanthanoid cation and is preferably selected from Ce(III), Pr(III), Nd(III), Pm(III), Sm(III), Eu(III), Gd(III), Tb(III), Dy(III), Ho(III), Er(III), Tm(III), Yb(III), Lu(III). The central atoms are particularly preferably Ce(III), Nd(III), Eu(III) or Tb(III). For complexes of the formula (V), M(II) preferably represents a divalent lanthanoid cation, for example Sm(II), Eu(II), Tm(II) or Yb(II), etc. In the complexes of the formulae (III) to (VI), M is preferably 6- to 9-fold coordinated.

In a preferred embodiment of the invention, the complexes of the formula (II) contain a tetracoordinated metal ion. Such complexes have, in particular, the formula $M(E \cap E)(A \cap A''^-)$. In such complexes, the metal ion is preferably Pt(II), Ir(I), Cu(I) or Rh(I).

In a further embodiment of the invention, the complexes of the formula (II) contain a hexacoordinated metal ion or metal atom. Such complexes have, in particular, the formula $M(E \cap E)(A \cap A''^-)_2$, $M(E \cap E)_2 (A \cap A''^-)$ or $M(E \cap E)(A \cap A''^-)(L)_2$. In such complexes, the metal ion or metal atom is preferably Os(II), Ir(III), Ru(II), Re(I), Pt(IV) W(0), W(II), W(III), W(IV), W(V) or W(VI).

Besides the high chemical stability and the favourable electronic properties (high energy levels of the excited singlet and triplet states), the bulk of the ligand of the formula (I) is also of importance for industrial application, for example as emitter in OLEDs. This applies, in particular, to the case of the square-planar complexes of Pt(II), Pd(II), Ir(I) or Rh(I), since neutral complexes of this type from the prior art, such as Pt(ppy)(CO)Cl, Pt(ppy)$_2$, Pt(ppy)(1) or Pt(ppy)(4) (where ppy=2-phenylpyridine), have a strong tendency towards aggregation. As a consequence, pronounced metal-metal interactions arise, which frequently have an adverse effect on the emission properties and may make the complexes unsuitable for OLEDs. In addition, aggregation can also have a very unfavourable effect on processability both in vacuum evaporation and also in wet-chemical processes.

Ligands which cause steric hindrance and prevent formation of stack-like oligo- and polymolecular aggregates can avoid the above-mentioned problems and enable the use of novel classes of monomeric triplet emitter materials. For example, some square-planar complexes of Pt(II) are very efficient emitters in their non-aggregated, monomeric form, but are virtually unusable in OLEDs for the above-mentioned reasons. The bisphosphines and bisarsines of type 7 (cf. FIG. 2) or the other ligands of the formula (I) which contain a nido-carborane skeleton combine the advantageous properties in one ligand:

(i) Negative charge of the ligand. This enables or simplifies the synthesis of neutral emitters.
(ii) Bidentate bonding to the central ion. This increases the stability of the resultant complex.
(iii) Rigidity of the auxiliary ligand. This reduces radiationless deactivation of the excited state.
(iv) Bulk of the ligand. This achieves good isolation of individual emitter molecules and prevents the formation of undesired aggregates.

The examples [Pt(ppy)(7a)], [Pt(ppy)(7b)], [Pt(dfppy)(7a)] and [Pt(thpy)(7a)](ppy=2-phenylpyridine, dfppy=2-(4,6-difluorophenyl)-pyridine, thpy=2-(2-thienyl)pyridine) shown below confirm that the ligands 7 (FIG. 2) block the aggregation of square-planar complexes and sterically isolate the emitting chromophore centres. This also enables high luminescence quantum yields of the monomers to be achieved in the solid state (100% emitter layer).

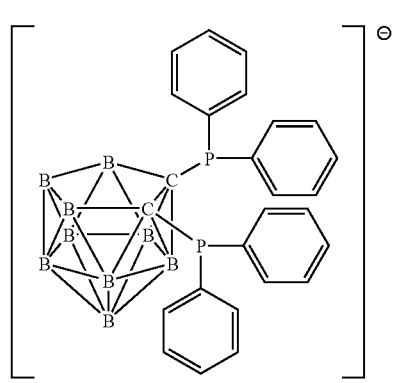

7a

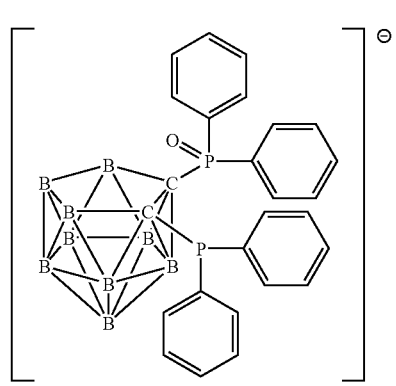

7b

Examples of preferred compounds are composed of one of each of the monoanionic, bidentate phosphine ligands from Table 1 depicted below in combination with a monocationic Pt(II) complex fragment from Table 2 or a monocationic Ir(III) complex fragment from Table 3. These complexes can be prepared, inter alia, using the synthetic methods explained below.

TABLE 1

Monoanionic bidentate phosphine ligands

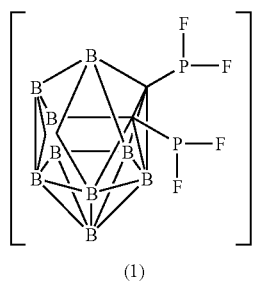

(1)

TABLE 1-continued
Monoanionic bidentate phosphine ligands
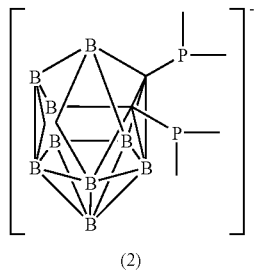
(2)
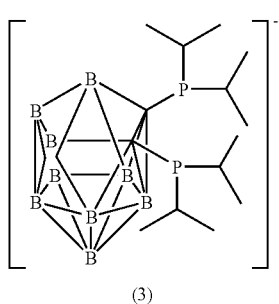
(3)
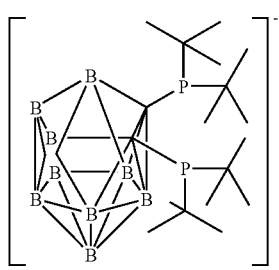
(4)
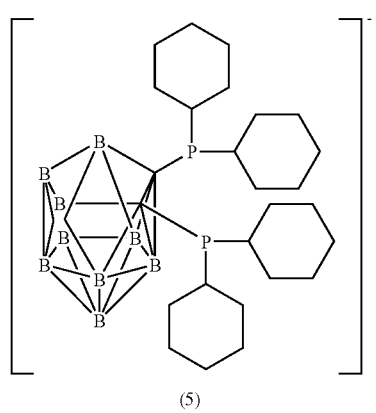
(5)
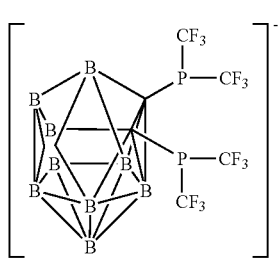
(6)
TABLE 1-continued
Monoanionic bidentate phosphine ligands
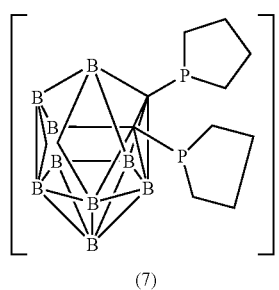
(7)
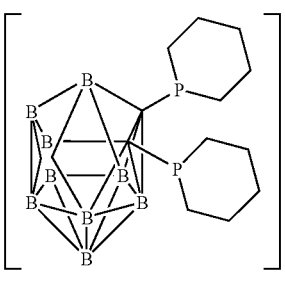
(8)
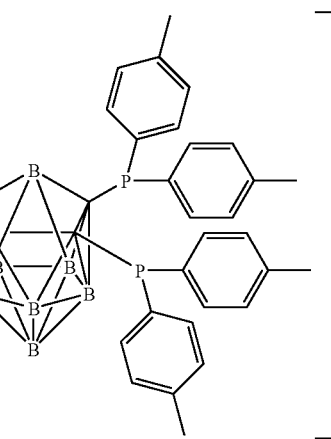
(9)

TABLE 1-continued
Monoanionic bidentate phosphine ligands
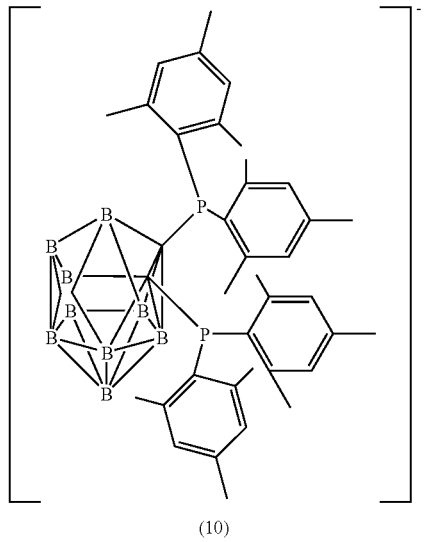
(10)
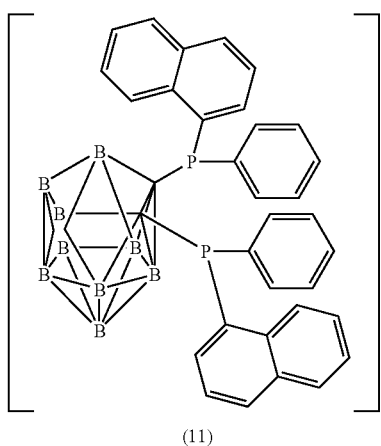
(11)
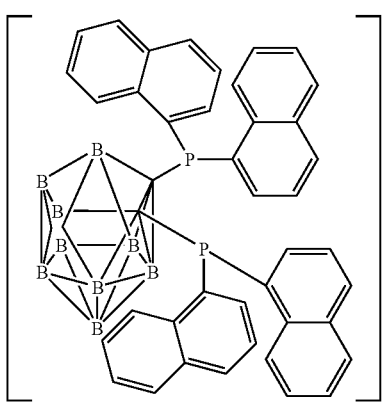
(12)
TABLE 1-continued
Monoanionic bidentate phosphine ligands
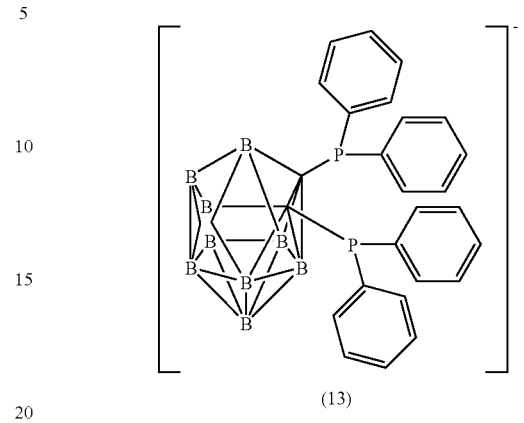
(13)
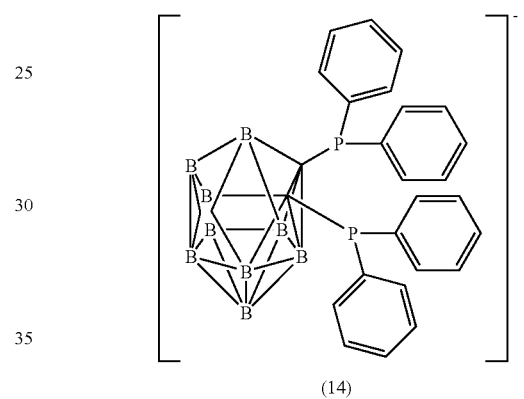
(14)
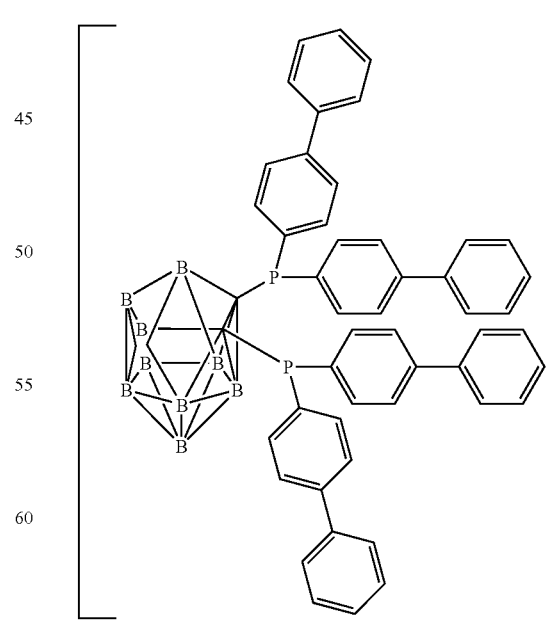
(15)

TABLE 1-continued
Monoanionic bidentate phosphine ligands
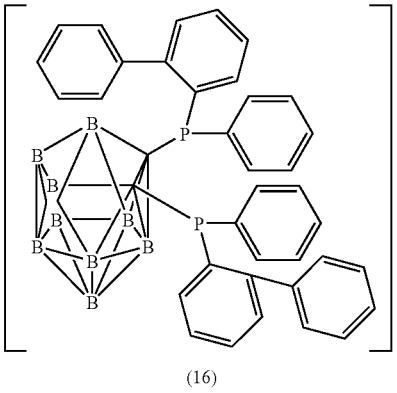
(16)
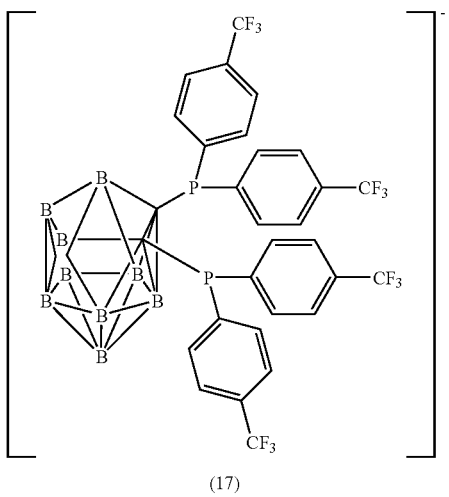
(17)
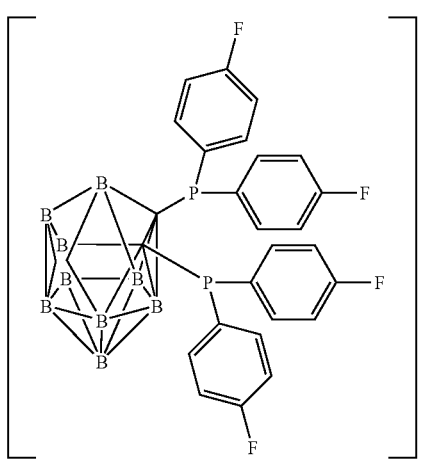
(18)
TABLE 1-continued
Monoanionic bidentate phosphine ligands
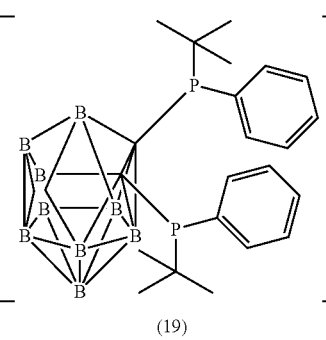
(19)
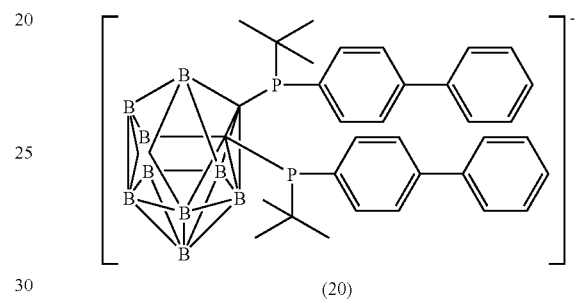
(20)
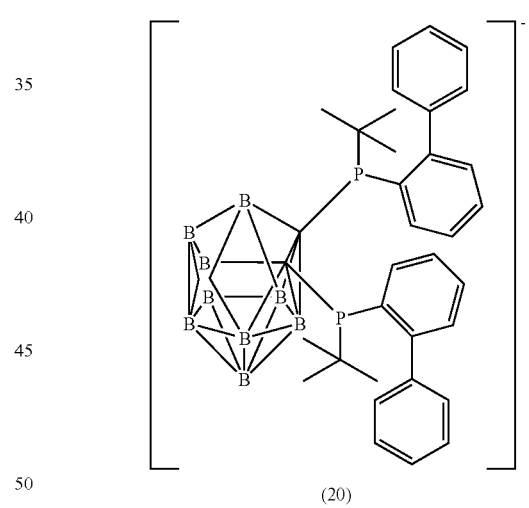
(20)
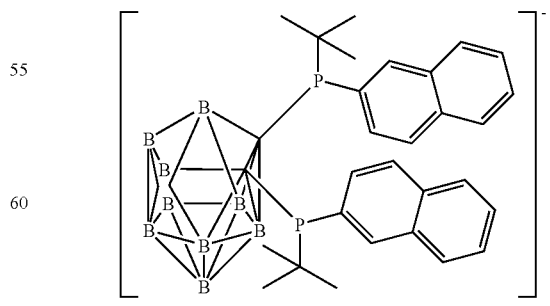
(21)

TABLE 2
| Monocationic Pt(II) complex fragments |
|---|
| 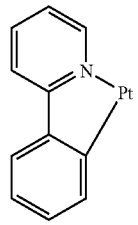 (1) |
| 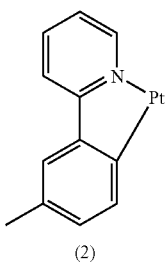 (2) |
| 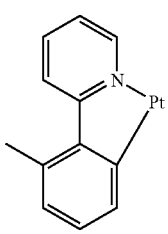 (3) |
| 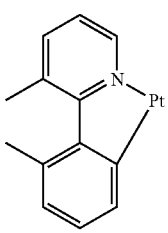 (4) |
| 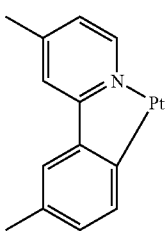 (5) |
TABLE 2-continued
| Monocationic Pt(II) complex fragments |
|---|
| (6) |
| (7) |
| (8) |
| (9) |

TABLE 2-continued
Monocationic Pt(II) complex fragments
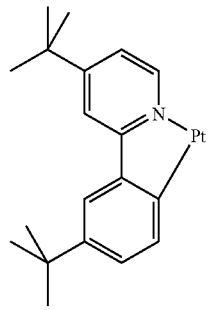
(10)
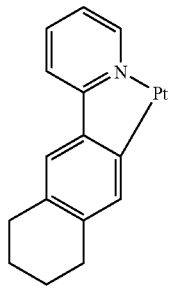
(11)
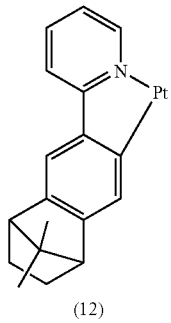
(12)
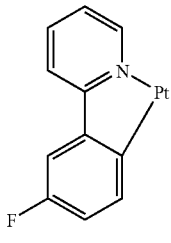
(13)
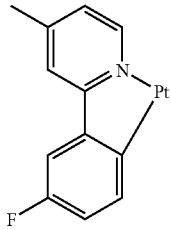
(14)
TABLE 2-continued
Monocationic Pt(II) complex fragments
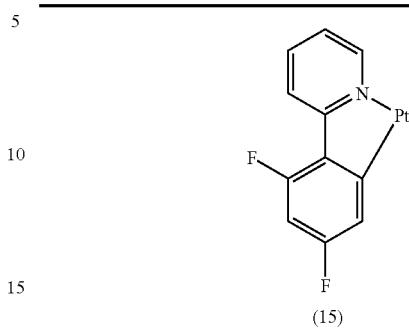
(15)
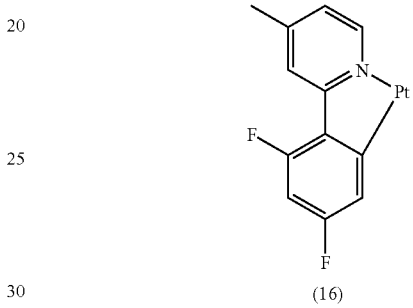
(16)
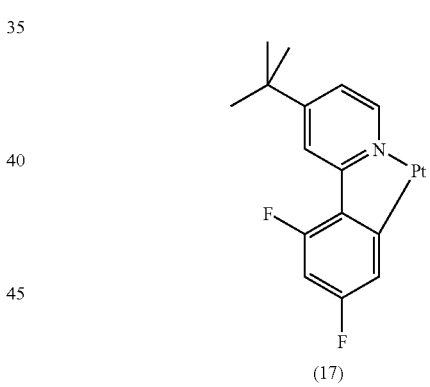
(17)
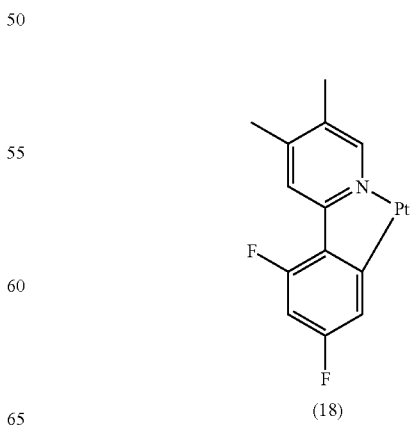
(18)

TABLE 2-continued
Monocationic Pt(II) complex fragments
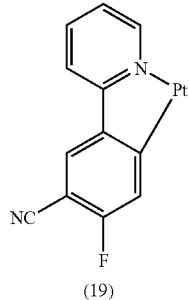
(19)
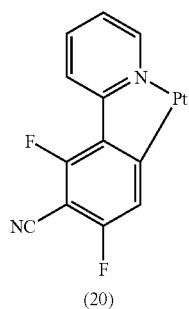
(20)
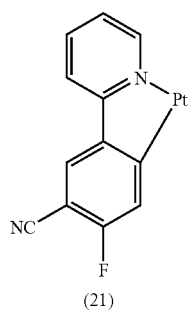
(21)
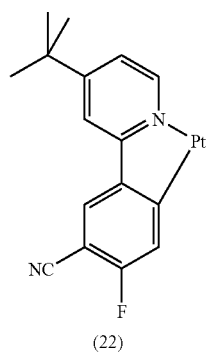
(22)
TABLE 2-continued
Monocationic Pt(II) complex fragments
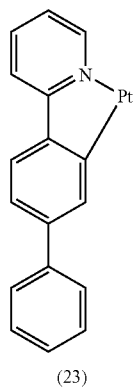
(23)
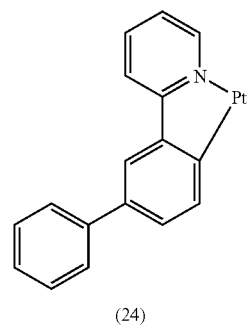
(24)
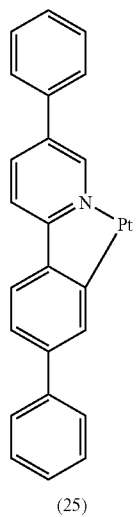
(25)

TABLE 2-continued
Monocationic Pt(II) complex fragments
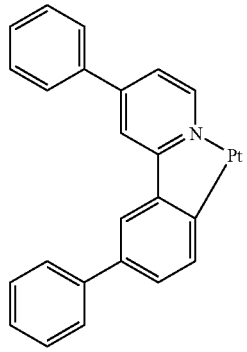
(26)
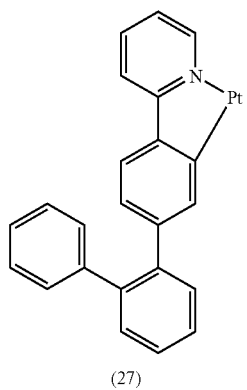
(27)
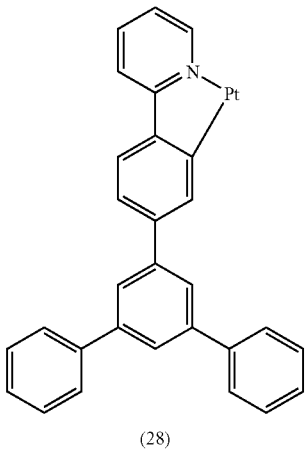
(28)
TABLE 2-continued
Monocationic Pt(II) complex fragments
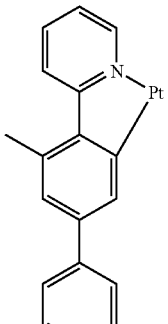
(29)
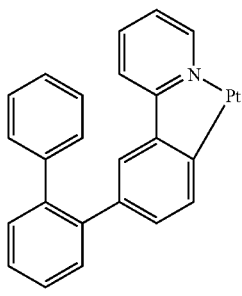
(30)
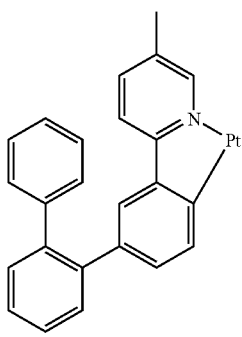
(31)
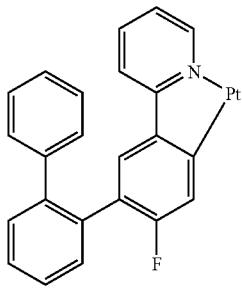
(32)

TABLE 2-continued
Monocationic Pt(II) complex fragments
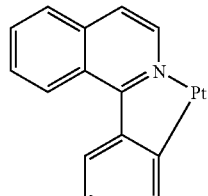
(33)
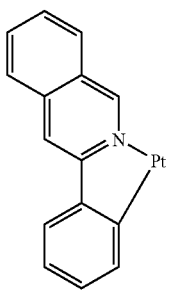
(34)
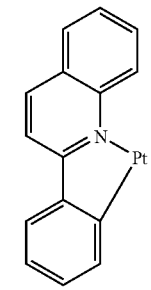
(35)
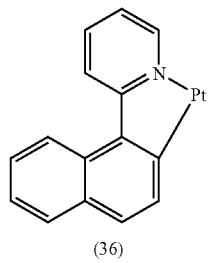
(36)
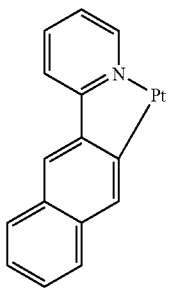
(37)
TABLE 2-continued
Monocationic Pt(II) complex fragments
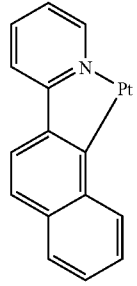
(38)
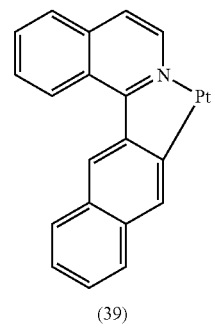
(39)
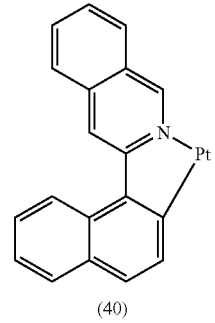
(40)
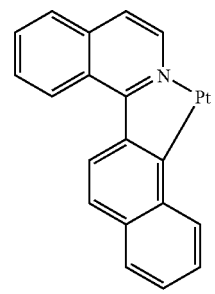
(41)

TABLE 2-continued
Monocationic Pt(II) complex fragments
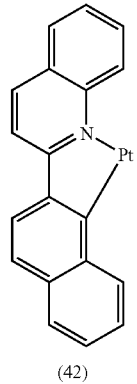
(42)
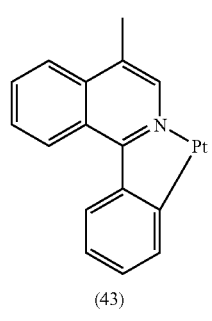
(43)
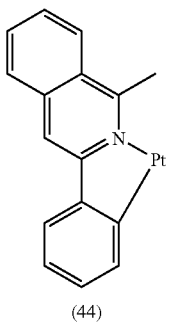
(44)
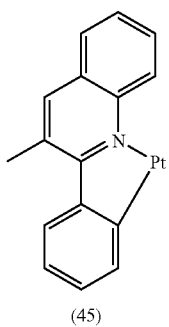
(45)
TABLE 2-continued
Monocationic Pt(II) complex fragments
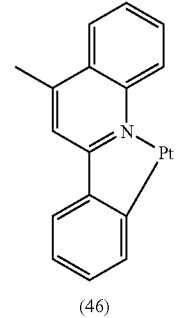
(46)
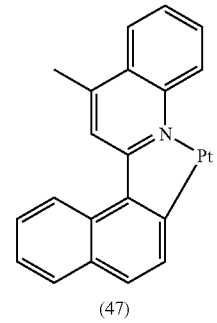
(47)
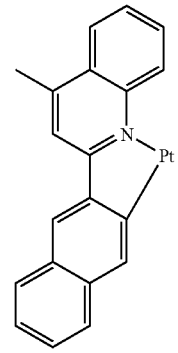
(48)
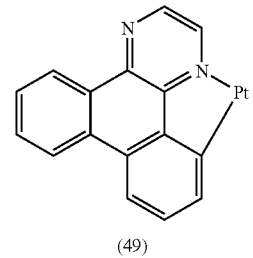
(49)

TABLE 2-continued
Monocationic Pt(II) complex fragments
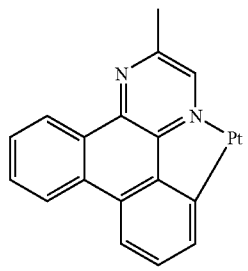
(50)
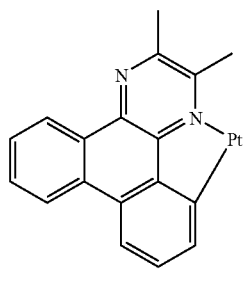
(51)
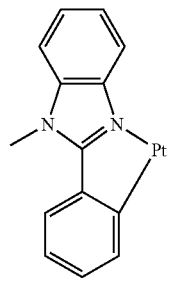
(52)
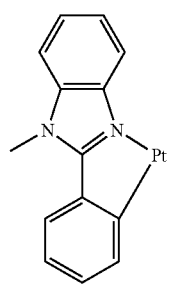
(53)
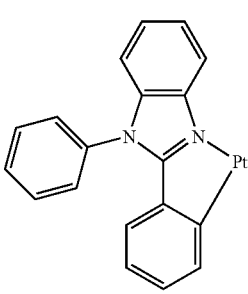
(54)
TABLE 2-continued
Monocationic Pt(II) complex fragments
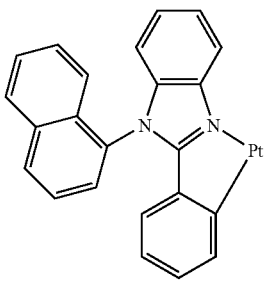
(55)
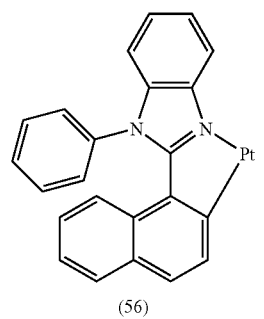
(56)
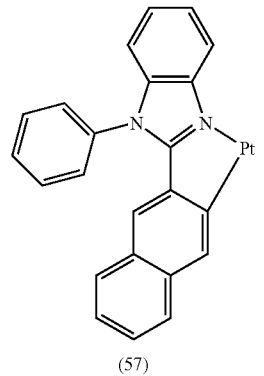
(57)
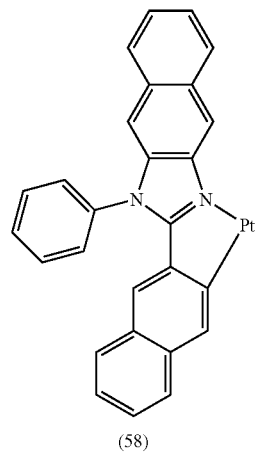
(58)

TABLE 2-continued
Monocationic Pt(II) complex fragments
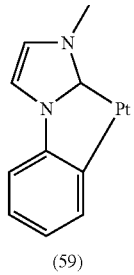
(59)
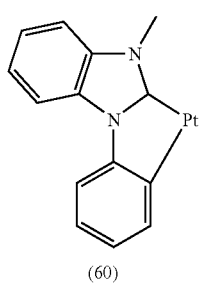
(60)
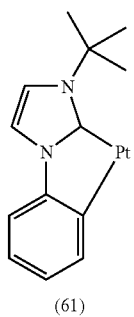
(61)
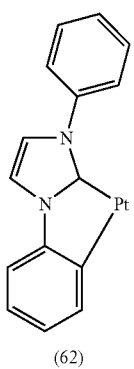
(62)
TABLE 2-continued
Monocationic Pt(II) complex fragments
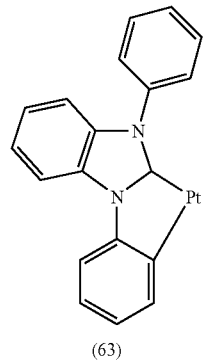
(63)
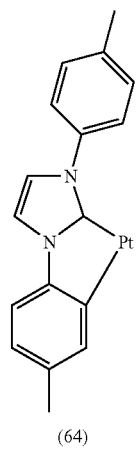
(64)
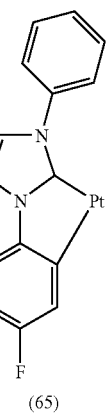
(65)

TABLE 2-continued
Monocationic Pt(II) complex fragments
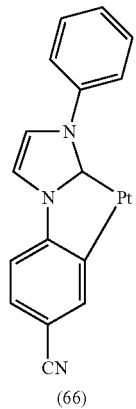
(66)
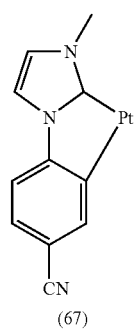
(67)
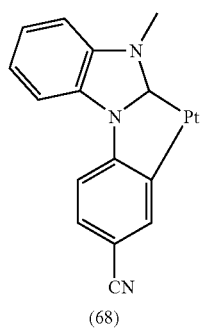
(68)
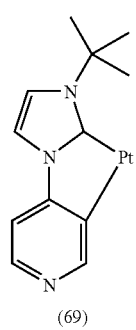
(69)
TABLE 2-continued
Monocationic Pt(II) complex fragments
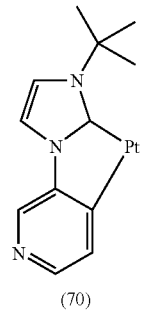
(70)
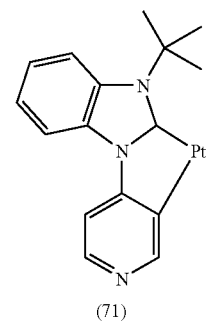
(71)
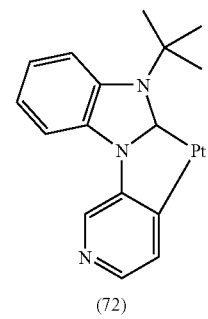
(72)
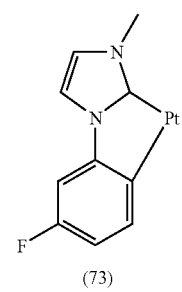
(73)
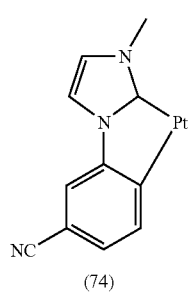
(74)

TABLE 2-continued
Monocationic Pt(II) complex fragments
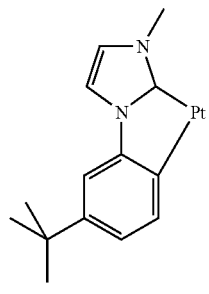
(75)
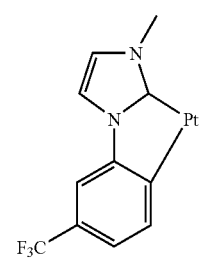
(76)
TABLE 3
Monocationic Ir(III) complex fragments
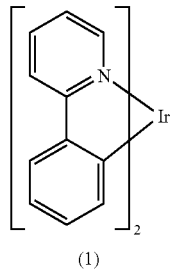
(1)
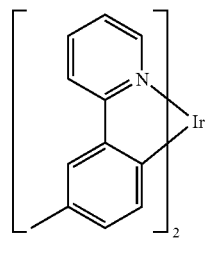
(2)
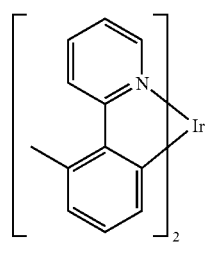
(3)
TABLE 3-continued
Monocationic Ir(III) complex fragments
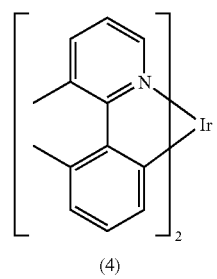
(4)
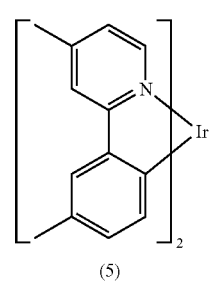
(5)
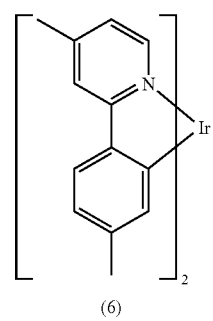
(6)
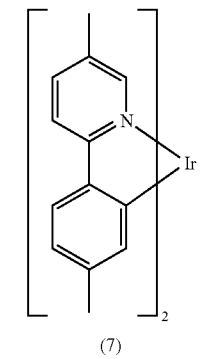
(7)
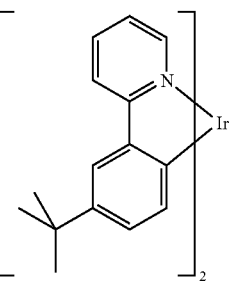
(8)

TABLE 3-continued
Monocationic Ir(III) complex fragments
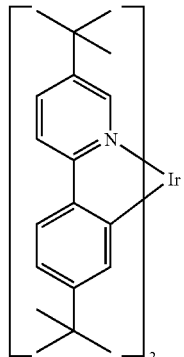
(9)
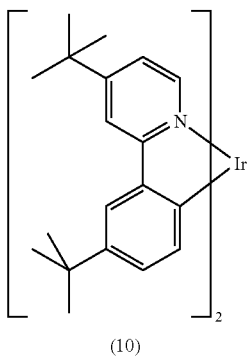
(10)
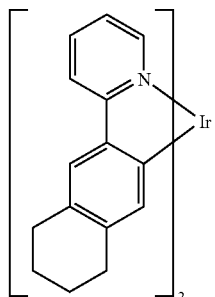
(11)
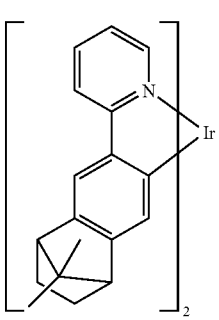
(12)
TABLE 3-continued
Monocationic Ir(III) complex fragments
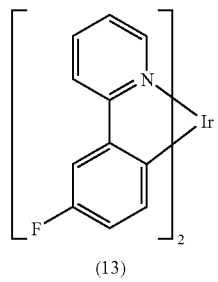
(13)
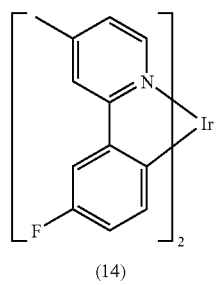
(14)
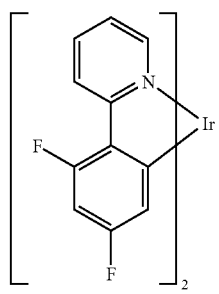
(15)
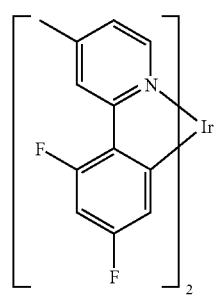
(16)
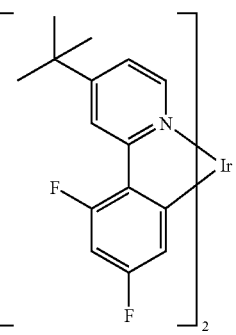
(17)

TABLE 3-continued
Monocationic Ir(III) complex fragments
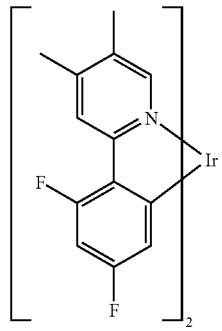
(18)
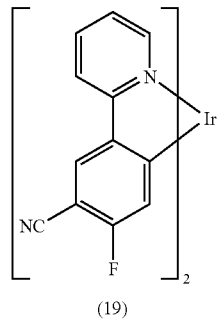
(19)
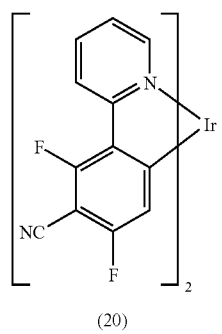
(20)
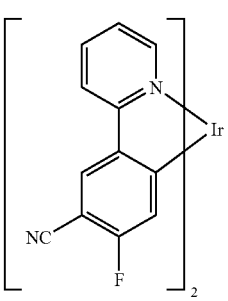
(21)
TABLE 3-continued
Monocationic Ir(III) complex fragments
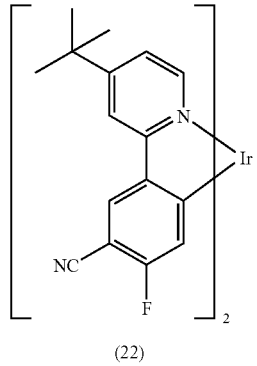
(22)
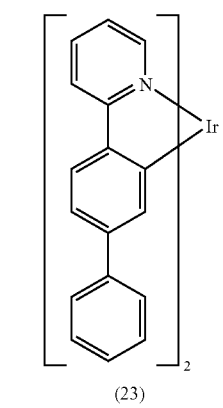
(23)
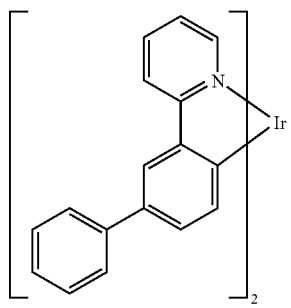
(24)

TABLE 3-continued
Monocationic Ir(III) complex fragments
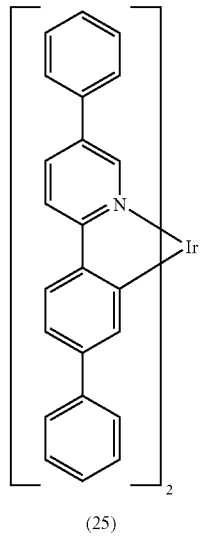
(25)
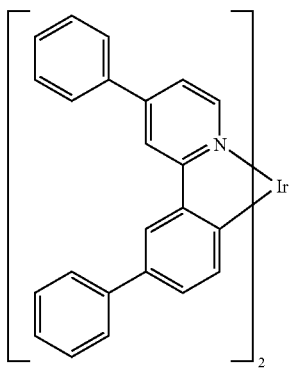
(26)
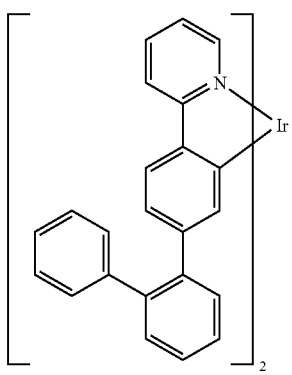
(27)
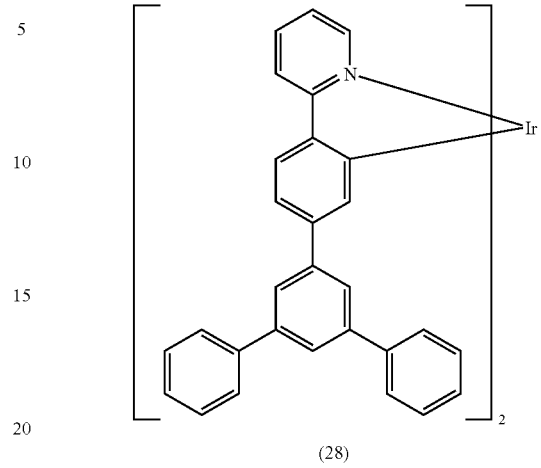
(28)
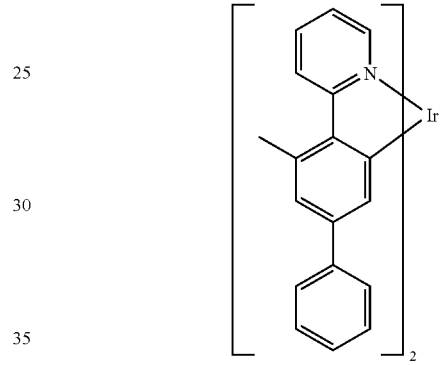
(29)
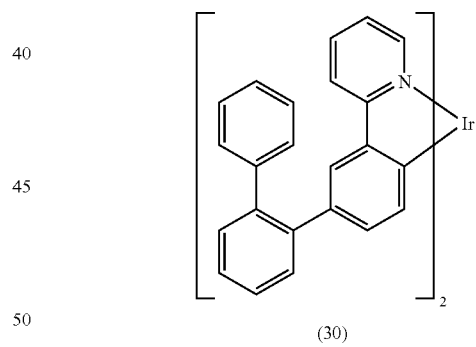
(30)
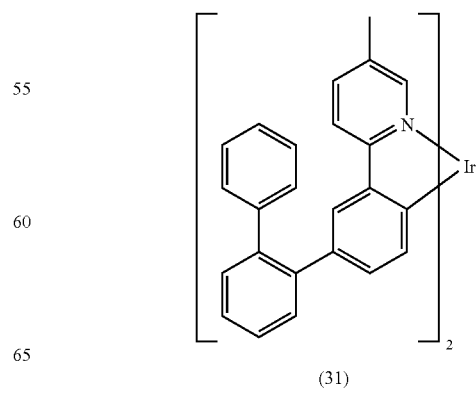
(31)

TABLE 3-continued
Monocationic Ir(III) complex fragments
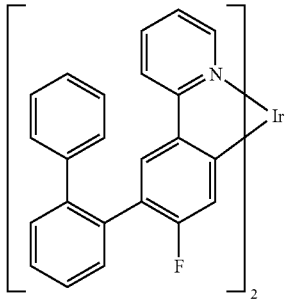
(32)
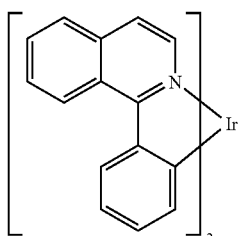
(33)
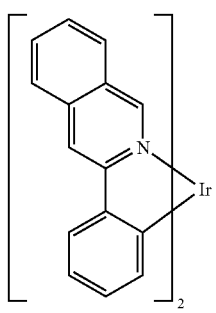
(34)
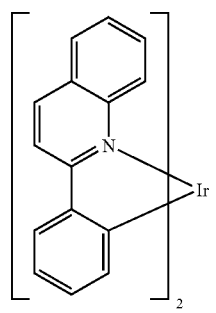
(35)
TABLE 3-continued
Monocationic Ir(III) complex fragments
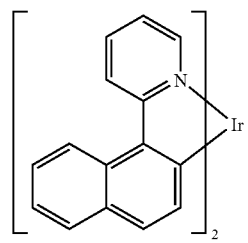
(36)
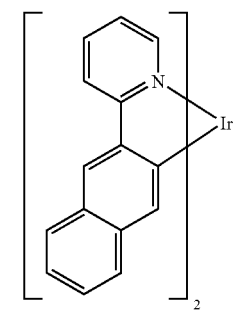
(37)
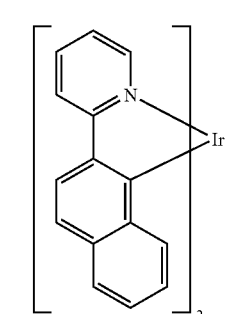
(38)
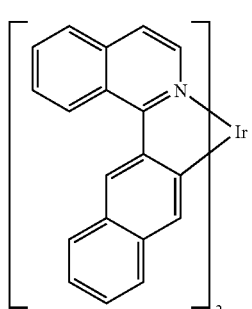
(39)

TABLE 3-continued
Monocationic Ir(III) complex fragments
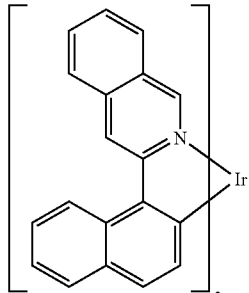
(40)
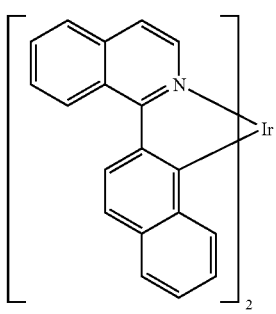
(41)
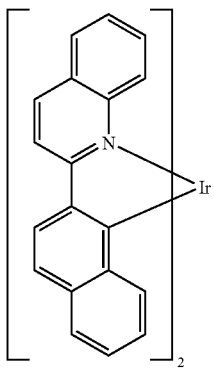
(42)
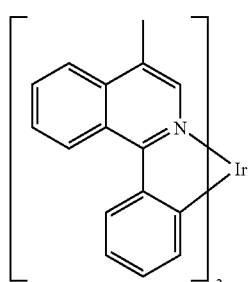
(43)
TABLE 3-continued
Monocationic Ir(III) complex fragments
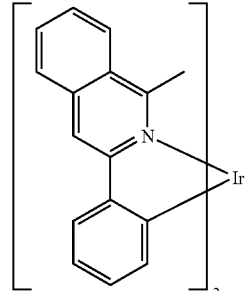
(44)
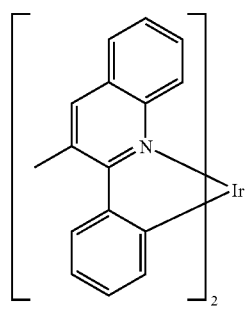
(45)
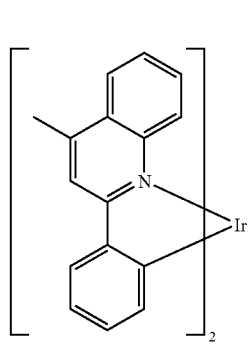
(46)
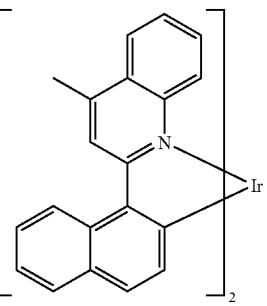
(47)

TABLE 3-continued
Monocationic Ir(III) complex fragments
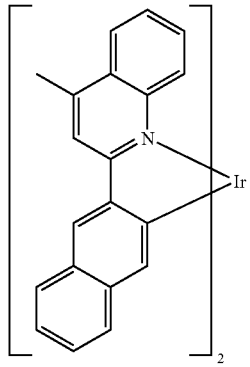
(48)
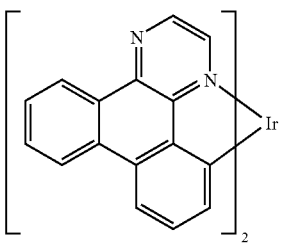
(49)
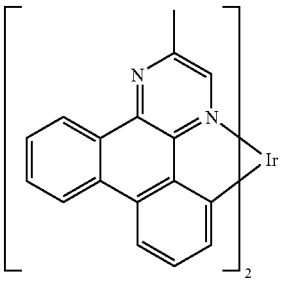
(50)
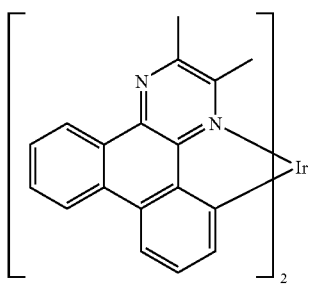
(51)
TABLE 3-continued
Monocationic Ir(III) complex fragments
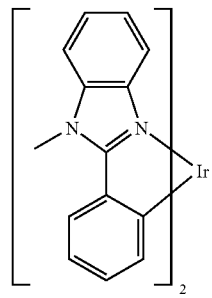
(52)
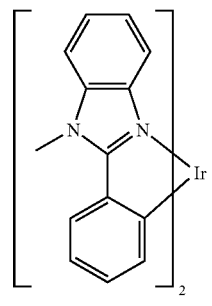
(53)
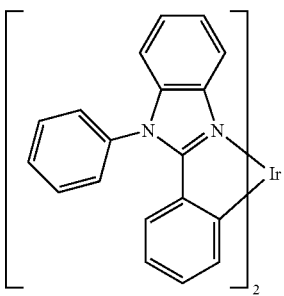
(54)
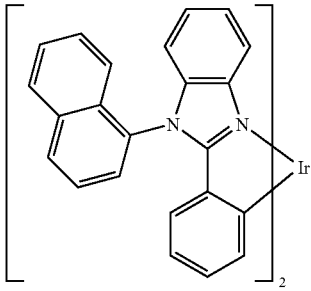
(55)

TABLE 3-continued
Monocationic Ir(III) complex fragments
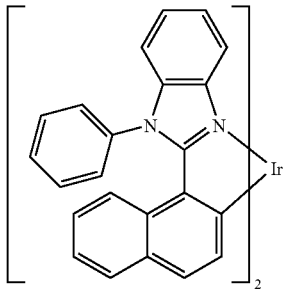
(56)
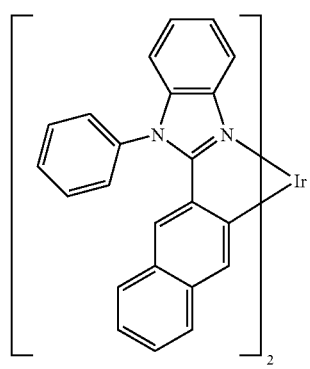
(57)
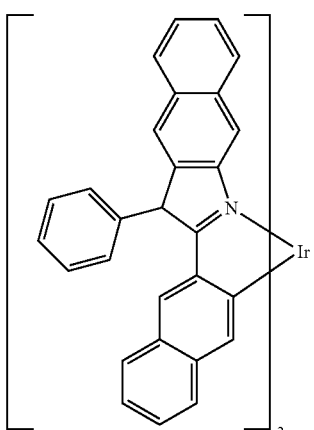
(58)
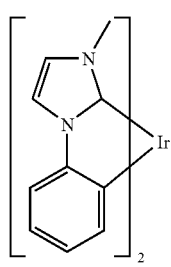
(59)
TABLE 3-continued
Monocationic Ir(III) complex fragments
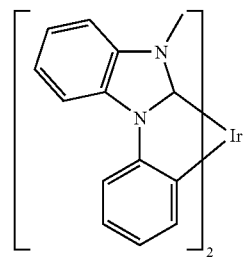
(60)
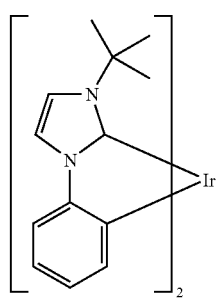
(61)
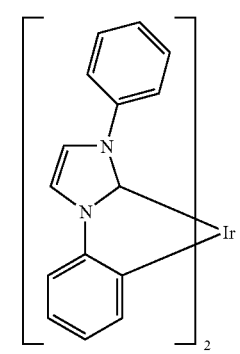
(62)
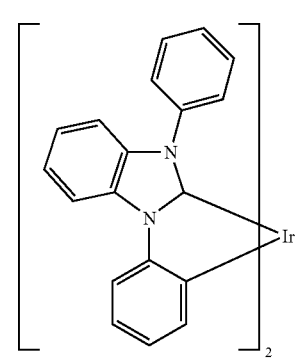
(63)

TABLE 3-continued
Monocationic Ir(III) complex fragments
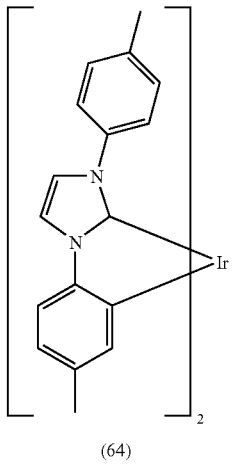
(64)
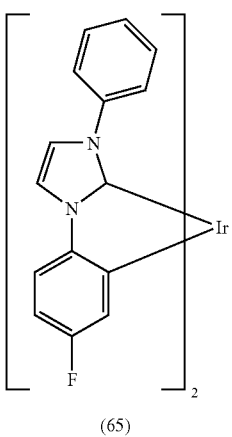
(65)
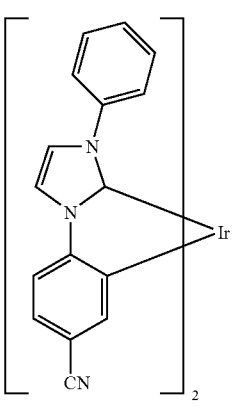
(66)
TABLE 3-continued
Monocationic Ir(III) complex fragments
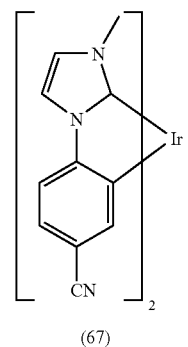
(67)
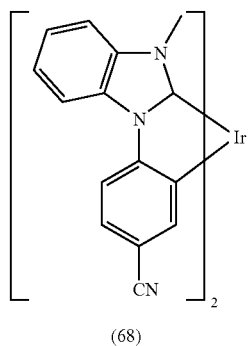
(68)
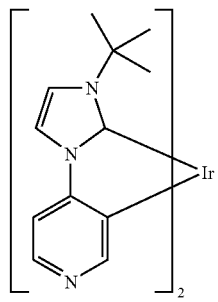
(69)
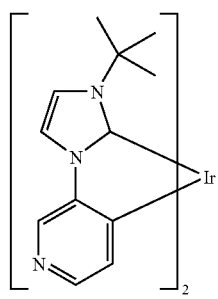
(70)

TABLE 3-continued

Monocationic Ir(III) complex fragments

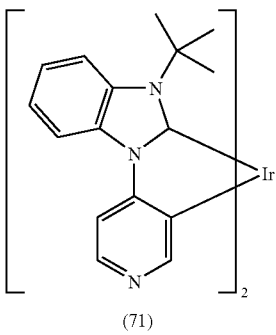

(71)

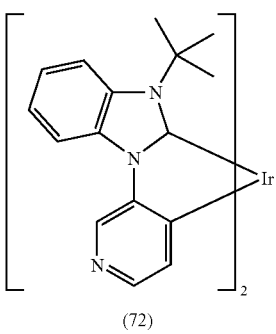

(72)

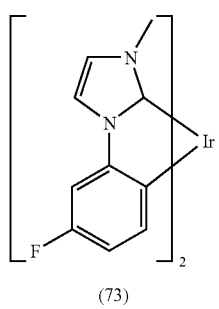

(73)

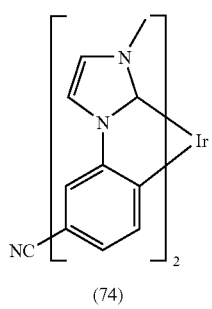

(74)

TABLE 3-continued

Monocationic Ir(III) complex fragments

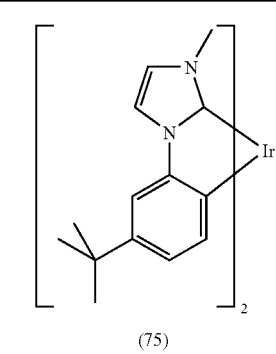

(75)

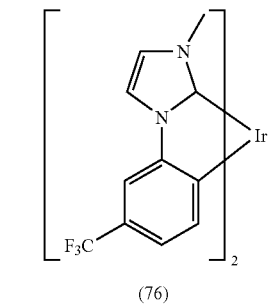

(76)

For the synthesis of metal complexes containing ligands of the formula (I), for example containing the ligand 7 (FIG. 2), these ligands can be used in the form of a soluble salt (for example with $N(C_4H_9)_4^+$ as counterion) (see Example 3). Alternatively, a neutral closo-carborane-diphosphine or diarsine $B_{10}H_{10}C_2(ER_2)_2$ 8 can be used as starting material (see Examples 1 and 2). 8a (E=P, R=Ph) was obtained as long ago as 1963 in accordance with Eq. 1 from the 1,2-carborane by reaction with nBuLi and Ph$_2$PCl (R. P. Alexander, H. Schroeder, *Inorg. Chem.* 1963, 2, 1107).

Eq. 1

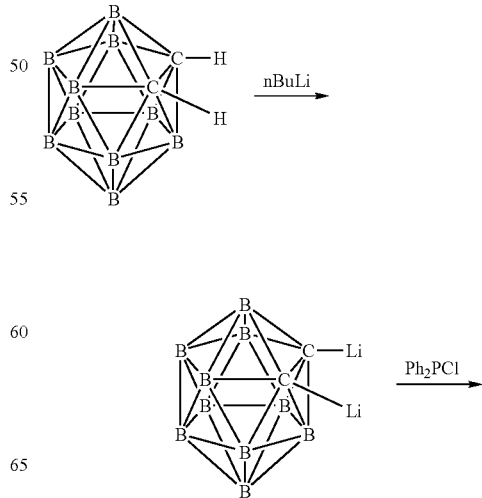

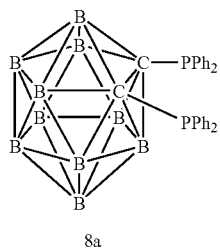

8a

The closo-carborane unit of the complex formed in situ is deboronated in alcoholic solution to give the nido-carborane. This synthetic route is particularly important for complexes containing ligands 7 $B_9H_{10}C_2(ER_2)_2$, which can only be synthesised with difficulty, or not at all, as free ligands (for example ligands where R=$C_nH_{2n+1}$) (F. Teixidor, C. Vinas, M. M. Abad, R. Nunez, R. Kivekas, R. Sillanpäa, *J. Organomet. Chem.*, 1995, 503, 193). Besides the symmetrically substituted biphosphine- and biarsine-carboranes, asymmetrically substituted derivatives, for example $(B_{10}H_{10}C_2)(PR_2)(AsR_2)$, are also accessible. In the synthesis of such compounds, the use of protecting groups is necessary. For protection of the C—H function in carboranes, use can be made of, for example, halo-alkylsilanes (F. A. Gomez, S. E. Johnson, M. F. Hawthorne, J. Am. Chem. Soc., 1991, 113, 5915).

These ligands can be introduced into the metal complexes by standard methods, as are familiar to the person skilled in the art of organometallic chemistry. Thus, these ligands can be introduced, for example, into iridium complexes by reacting the chloro-bridged dimer, for example $[(ppy)_2IrCl]_2$ (where ppy=2-phenylpyridine), with the ligand of the formula (I).

The complexes described above containing a ligand of the formula (I), in particular complexes of the formula (II) or formulae (III) to (VI), or the preferred embodiments mentioned above, are used as active component in the organic electronic device. Active components are generally the organic or inorganic materials which are introduced between the anode and cathode, for example charge-injection, charge-transport or charge-blocking materials, but in particular emission materials. The compounds according to the invention exhibit particularly good properties for these functions, in particular as emission material in organic electroluminescent devices, as described in greater detail below. Organic electroluminescent devices are therefore a preferred embodiment of the invention.

The way in which an embodiment of the metal-complex use according to the invention functions in a light-emitting device is shown diagrammatically in FIG. 1. The device comprises at least one anode, a cathode and an emitter layer. One or both of the electrodes used as cathode or anode advantageously has a transparent design, so that the light can be emitted through this electrode. The transparent electrode material used is preferably indium tin oxide (ITO). A transparent anode is particularly preferably employed. The other electrode may likewise be made from a transparent material, but may also be formed from another material having a suitable electron work function if light is only to be emitted through one of the two electrodes. The second electrode, in particular the cathode, preferably consists of a metal having high electrical conductivity, for example aluminium, or silver, or an Mg/Ag or Ca/Ag alloy. An emitter layer is arranged between the two electrodes. This may be in direct contact with the anode and the cathode or in indirect contact, where indirect contact means that further layers are present between the cathode or anode and the emitter layer so that the emitter layer and the anode and/or cathode do not touch one another, but instead are in electrical contact with one another via further interlayers. On application of a voltage, for example a voltage of 2-20 V, in particular 3-10 V, negatively charged electrons leave the cathode, for example a conductive metal layer, particularly preferably an aluminium cathode, and enter a thin electron-conduction layer and migrate in the direction of the positive anode. Positive charge carriers, so-called holes, in turn migrate from this anode and enter an organic hole-transport layer in the direction of the cathode. These holes move in the opposite direction compared with the electrons, more precisely towards the negative cathode. An emitter layer, which preferably likewise consists of an organic material, arranged between the cathode and anode comprises, in accordance with the invention, organometallic complexes containing auxiliary ligands of the formula (I) as emitter molecules. The migrating charge carriers, i.e. a negatively charged electron and a positively charged hole, recombine at the emitter molecules or in their vicinity and result in neutral, but energetically excited states of the emitter molecules. The excited states of the emitter molecules then release the energy as light emission. The emitter layer may also be identical to the hole- and/or electron-transport layer if the emitter molecules are located in these layers.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. Interlayers, which have, for example, an exciton-blocking function, may likewise be introduced between two emitting layers. However, it should be pointed out that each of these layers does not necessarily have to be present. The organic electroluminescent device here may comprise one emitting layer or a plurality of emitting layers, where at least one emitting layer comprises at least one metal complex containing a ligand of the formula (I). If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

In a preferred embodiment of the invention, the organic electronic device comprises the metal complex containing the ligand of the formula (I) or the preferred embodiments mentioned above as emitting compound in an emitting layer. This is the case, in particular, if the metal M is a transition metal, in particular iridium or platinum, or a lanthanide.

If the metal complex containing a ligand of the formula (I) or the complex of the formula (II) is employed as emitting compound in an emitting layer, it is preferably employed in combination with one or more matrix materials. However, the metal complex can also be employed as a pure layer. The mixture of the metal complex and the matrix material comprises between 0.1 and 99% by weight, preferably between 2 and 90% by weight, particularly preferably between 3 and 40% by weight, in particular between 5 and 15% by weight, of the metal complex, based on the entire mixture of emitter and matrix material. Correspondingly, the mixture comprises between 99 and 1% by weight, preferably between 98 and 10% by weight, particularly preferably between 97 and 60% by weight, in particular between 95 and 85% by weight, of the matrix material, based on the entire mixture of emitter and matrix material.

Preferred matrix materials are CBP (N,N-biscarbazolylbiphenyl), carbazole derivatives (for example in accordance with WO 05/039246, US 2005/0069729, JP 2004/288381, EP 1205527 or the unpublished application DE 102007002714.3), PVK (polyvinylcarbazole), azacarbazoles (for example in accordance with EP 1617710, EP 1617711, EP 1731584, JP 2005/347160), ketones (for example in accordance with WO 04/093207), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137,725), silanes (for example in accordance with WO 05/111172), azaboroles or boronic esters (for example in accordance with WO 06/117052).

It has been found that the use according to the invention of metal complexes containing an auxiliary ligand of the formula (I) in the emitter layer enables light-emitting devices to be obtained which have excellent properties. In particular, the metal complexes employed in accordance with the invention exhibit high emission quantum yields. In addition, the complexes can be varied by substitution and/or replacement of the ligands, giving rise to a variety of possibilities for the modification or control of the emission properties. In addition, compounds having high sublimability can be obtained through a suitable choice of the ligands.

Preference is furthermore given to an organic electroluminescent device, characterised in that one or more layers are applied by means of a sublimation process, in which the materials are applied by vapour deposition in vacuum sublimation units at a pressure of less than $10^{-5}$ mbar, preferably less than $10^{-6}$ mbar, particularly preferably less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are necessary for this purpose.

These processes are generally known to the person skilled in the art and can be applied by him without problems to organic electroluminescent devices comprising metal complexes containing ligands of the formula (I) or the preferred metal complexes mentioned above.

The light-emitting devices according to the invention can be manufactured, for example, by means of the vacuum sublimation technique and comprise a plurality of further layers, in particular an electron-injection layer and an electron-transport layer (for example $Alq_3$=aluminium 8-hydroxyquinoline or BAlq=aluminium bis(2-methyl-8-hydroxyquinolato)-4-phenylphenolate) and/or a hole-injection layer (for example CuPc=copper phthalocyanine) and/or hole-transport layer (for example α-NPD=4,4'-bis[N-(1-naphthyl)N-phenylamino)biphenyl]). However, it is also possible for the emitter layer to take on functions of the hole- or electron-transport layer.

The emitter layer preferably consists of an organic matrix material having a sufficiently large singlet $S_0$-triplet $T_1$ energy gap (matrix material), for example comprising UGH (ultra high energy gap hosts), CBP (4,4'-bis(9-carbazolyl) biphenyl) or other matrix materials. The emitter complex is doped into this matrix material, for example preferably in an amount of 0.1 to 100 percent by weight, in particular 1 to 20 percent by weight. The emitter layer can also be obtained without a matrix by applying the corresponding complex as a 100% material.

In a particularly preferred embodiment, the light-emitting device according to the invention also has an electron-injection layer, for example comprising CsF or LiF, as interlayer between the cathode and the emitter layer or an electron-transport layer. This layer has, in particular, a thickness of 0.5 nm to 2 nm, preferably about 1 nm. This interlayer causes predominantly a reduction in the electron work function.

The light-emitting device is furthermore preferably applied to a substrate, for example to a glass substrate.

For example, good power efficiencies can be achieved in a typical OLED layer structure consisting of an ITO anode, a hole conductor, for example comprising PEDOT/PSS, the emitter layer according to the invention, optionally a hole-blocking layer, an electron-transport layer, a thin LiF or CsF interlayer for improving electron injection, and a metal electrode (cathode). These various layers having a total thickness of a few 100 nm can be applied, for example, to a glass substrate or another support material.

The OLED device can also be partly manufactured by wet-chemical methods, for example with the following structure: glass substrate, trans-parent ITO layer (comprising indium tin oxide), for example PEDOT/PSS (polyethylenedioxythiophene/polystyrenesulfonic acid, for example 40 nm) or other layers which improve hole injection, 100% complex according to the invention (for example 10 to 80 nm) or doped (for example, in particular, 1% to 20%) into a suitable matrix, for example PVK (for example 40 nm), a vapour-deposited electron-transport layer, for example comprising $Alq_3$ (for example 40 nm), vapour-deposited LiF or CsF as protective layer (for example 0.8 nm), vapour-deposited metal cathode, Al or Ag or Mg/Ag (for example 200 nm).

An OLED structure for a soluble emitter according to the invention particularly preferably has the structure described below and depicted in FIG. 3, but comprises at least one, more preferably at least two and most preferably all of the layers mentioned below.

The device is preferably applied to a support material, in particular to glass or another solid or flexible transparent material. An anode, for example an indium tin oxide (ITO) anode, is applied to the support material. The layer thickness of the anode is preferably 10 nm to 100 nm, in particular 30 to 50 nm. An HTL layer comprising a hole-transport material, in particular comprising a hole-transport material which is water-soluble, is applied to the anode and between the anode and the emitter layer. A hole-transport material of this type is, for example, PEDOT/PSS (polyethylenedioxythiophene/polystyrenesulfonic acid) or novel HTL materials (DuPont) for extending the device lifetime. The layer thickness of the HTL layer is preferably 10 to 100 nm, in particular 40 to 60 nm. Next, the emitter layer (EML), which comprises a soluble emitter according to the invention, is applied. The material can be dissolved in a solvent, for example in acetone, dichloromethane, toluene or acetonitrile. This enables dissolution of the underlying PEDOT/PSS layer to be avoided. The emitter material according to the invention can be employed in low concentration, for example 0.1 to 30% by weight, but also in higher concentration or as a 100% layer. Metal complexes are preferably introduced in a concentration which prevents or greatly restricts triplet-triplet annihilation, in particular in a total concentration of greater than 1% by weight and less than 20% by weight. It is also possible to apply the emitter material highly or moderately doped in a suitable polymer layer (for example PVK=poly(N-vinylcarbazole)). For low-solubility emitter materials according to the invention, the application can be carried out by means of a colloidal suspension in a polymer. The emitter layer preferably has a layer thickness of 10 to 150 nm, in particular 30 to 100 nm. A layer of electron-transport material, in particular having a layer thickness of 10 to 80 nm, more preferably 30 to 50 nm, is preferably applied to the emitter layer. A suitable material for the electron-transport material layer (ETL) is, for example, $Alq_3$, LiQ (optionally in combination with a benzimidazole derivative) or a benzimidazole derivative which can be applied by vapour deposition. Next, a thin interlayer which reduces the electron-injection barrier and protects the ETL layer is preferably applied. This layer preferably has a thickness of between 0.1 and 2 nm, in particular between 0.5 and 1.5 nm, and preferably consists of CsF or LiF. This layer is generally applied by vapour deposition. For a further-simplified OLED structure, the ETL and/or the interlayer can optionally be omitted. Finally, a conductive cathode layer is applied, in particular by vapour deposition. The cathode layer preferably consists of a metal, in particular Al or Mg/Ag (in particular in the ratio 10:1).

Voltages of 3 to 10 V are preferably applied to the device.

In a preferred embodiment, an OLED structure for a sublimable emitter according to the invention also comprises at least one, in particular a plurality of and particularly preferably all of the layers mentioned below and depicted in FIG. 4, in addition to an anode, emitter layer and cathode.

The entire structure is preferably located on a support material, where, in particular, glass or any other solid or flexible transparent material can be employed for this purpose. The anode, for example an indium tin oxide (ITO) anode, is arranged on the support material. A hole-transport layer (HTL), for example α-NPD, is arranged on the anode and between the emitter layer and the anode. The thickness of the hole-transport layer is preferably 10 to 100 nm, in particular 30 to 50 nm. Further layers which improve hole injection, for example a copper phthalocyanine (CuPc) layer, can be arranged between the anode and the hole-transport layer. This layer preferably has a thickness of 5 to 50 nm, in particular 8 to 15 nm. An electron-blocking layer, which ensures that the electron transport towards the anode is suppressed, since a current of this type would cause ohmic losses, is preferably applied to the hole-transport layer and between the hole-transport layer and the emitter layer. The thickness of this electron-blocking layer is preferably 10 to 100 nm, in particular 20 to 40 nm. This additional layer can be omitted, in particular, if the HTL layer is already intrinsically a poor electron conductor.

The next layer is the emitter layer, which comprises or consists of the emitter material according to the invention. In the embodiment using sublimable emitters, the emitter materials are preferably applied by sublimation. The layer thickness is preferably between 10 nm and 150 nm, in particular between 30 nm and 100 nm. The emitter material according to the invention can also be co-evaporated together with other materials, in particular with matrix materials. For emitter materials according to the invention which emit in the green or red, common matrix materials, such as CBP (4,4'-bis(N-carbazolyl)biphenyl) or other matrix materials, for example those as listed above, are suitable. However, it is also possible to build up a 100% emitter-material layer. For emitter materials according to the invention which emit in the blue, UHG matrix materials (cf. M. E. Thompson et al., Chem. Mater. 2004, 16, 4743) or other materials having an adequate $S_0$-$T_1$ energy gap and matching hole and electron mobility are preferably employed. For the generation of mixed-colour light (for example white light) on use of compounds according to the invention containing various metal central ions, it is likewise possible to use co-evaporation.

In principle, common matrix materials for OLEDs, but also substantially inert polymers or small matrix molecules without particularly pronounced hole or electron mobilities can be employed in accordance with the invention as matrix materials if suitable doping for the generation of adequate charge-carrier mobilities is ensured.

A hole-blocking layer (HBL), which reduces ohmic losses, which could arise due to hole currents towards the cathode, is preferably applied to the emitter layer. This hole-blocking layer preferably has a thickness of 10 to 50 nm, in particular 15 to 25 nm. A suitable material for this purpose is, for example, BCP (4,7-diphenyl-2,9-dimethylphenanthroline, also known as bathocuproin). An ETL (electron-transport layer) comprising electron-transport material is preferably applied to the hole-blocking layer and between this layer and the cathode. This layer preferably consists of vapour-depositable $Alq_3$ or another common electron-transport material, for example benzimidazole derivatives or LiQ (lithium hydroxyquinolinate) in combination with benzimidazole derivatives, having a thickness of 10 to 100 nm, in particular 30 to 50 nm. An interlayer, for example comprising CsF or LiF, is preferably applied between the ETL and the cathode. This interlayer reduces the electron-injection barrier and protects the ETL. This layer is generally applied by vapour deposition. The interlayer is preferably very thin, in particular with a thickness of 0.2 to 5 nm, more preferably 0.5 to 2 nm. Finally, a conductive cathode layer, in particular having a thickness of 50 to 500 nm, more preferably 100 to 250 nm, is applied by vapour deposition. The cathode layer preferably consists of Al, Mg/Ag (in particular in the ratio 10:1) or other metals. Voltages of between 3 and 10 V are preferably applied to the OLED structure described for a sublimable emitter according to the invention.

The preferred embodiments of light-emitting opto-electronic devices described above are hermetically encapsulated in order to prevent the ingress of oxygen, water vapour or other gases or vapours. In a specific embodiment according to the invention, the sensor OLED, by contrast, the hermetic encapsulation is replaced by conventional packaging which is permeable to defined gases in order to detect the influence of the corresponding gases on light emission (change in colour, change in intensity, change in emission decay time) as evidence of the particular gas.

It is essential to the invention that the organic electronic device, in particular the light-emitting device, comprises, as emitter, at least one complex containing an auxiliary ligand of the formula (I).

It has now been found in accordance with the invention that metal complexes containing auxiliary ligands of the formula (I) are eminently suitable for opto-electronic applications and in particular as emitter molecules for light-emitting devices and in particular for organic light-emitting devices (OLEDs).

The emitter molecules employed in accordance with the invention are preferably complexes containing auxiliary ligands of the formula (I). These complexes are, in particular, luminescent or electroluminescent compounds.

The preferred complexes of the formula (II) given above, in which y is not equal to 0 and which have a direct metal-carbon bond from the metal to the ligand (A∩A″⁻), are novel and are therefore likewise a subject-matter of the present invention. The preferences indicated above for the organic electronic device apply.

The complexes of the formulae (III), (IV), (V) and (VI) given above are also novel and are therefore likewise a subject-matter of the present invention. Here too, the preferences indicated above for the organic electronic device apply.

The invention is explained further by the attached figures and the following examples, without wishing to restrict it thereby.

FIG. 3 shows an example of an OLED device comprising emitters according to the invention which are applied by wet-chemical methods.

FIGS. 4 and 5 show examples of an OLED device manufactured by means of vacuum sublimation.

Figure 1:
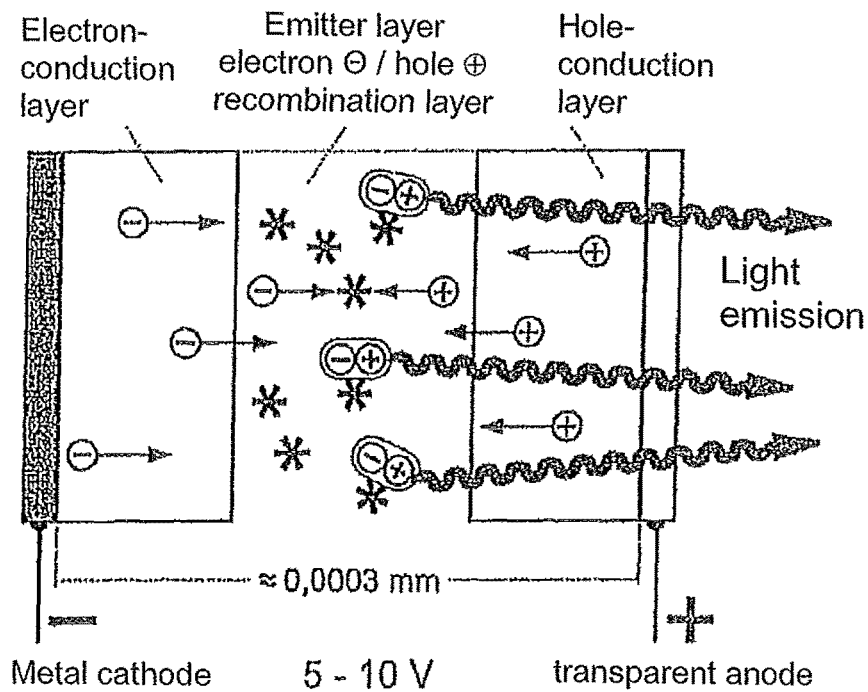
FIG. 1 shows a diagrammatic and simplified representation of the way in which an OLED functions.
Figure 2:
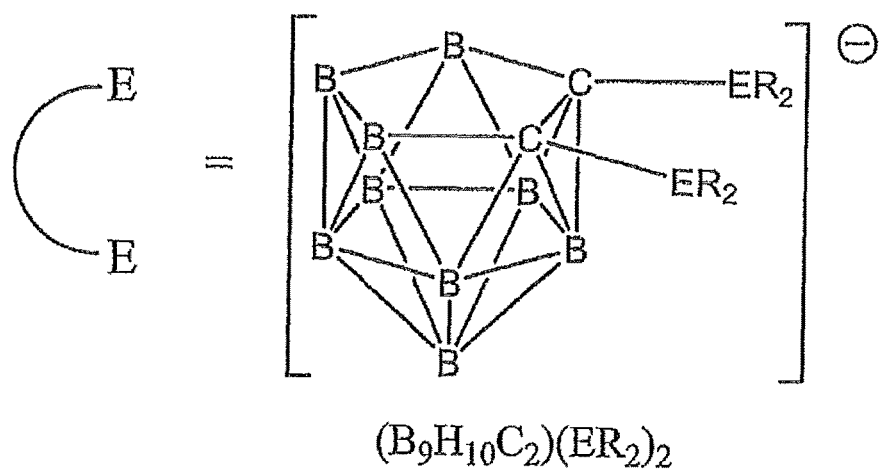
FIG. 2 shows the structural formula of the auxiliary ligand of the formula (I) according to the invention, (E∩E), namely the bidentate ligand which contains a 7,8-dicarba-nido-undecaborane skeleton (nido-carborane skeleton); E stands for P, As, P=O or As=O.
Figures 5, 6:
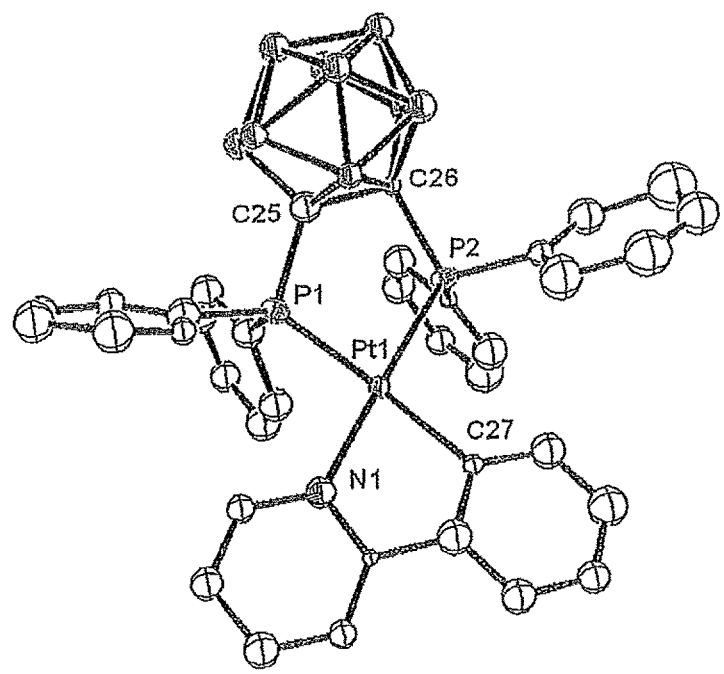

FIG. 6 shows the molecular structure of Pt(ppy)(7a) in the crystal. Hydrogen atoms are not shown. In crystals of Pt(ppy)(7a), the shortest intermolecular Pt—Pt separation is 8.54 Å, i.e. any formation of stack-like agglomerates (arrangements) is prevented by the bulky ligand 7a.

Figure 7:
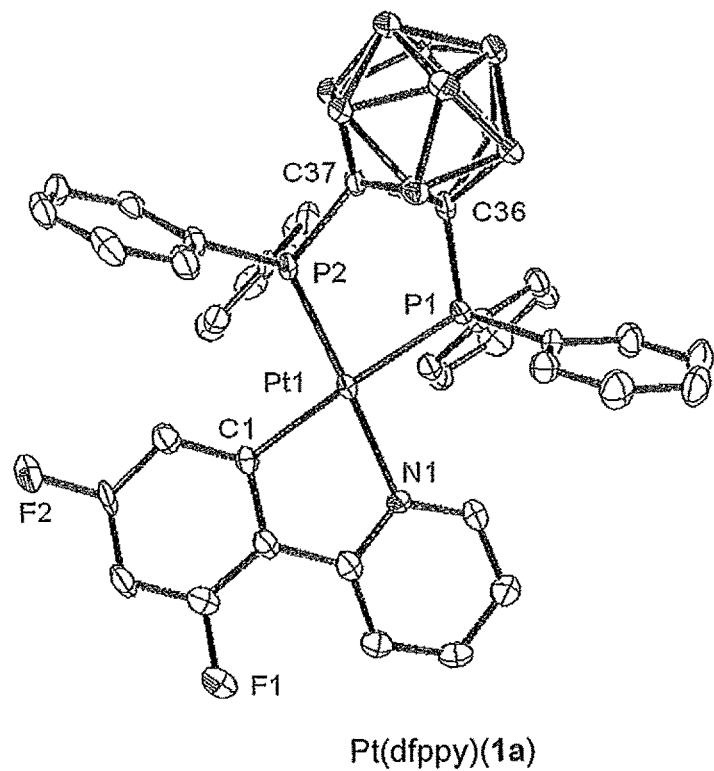

FIG. 7 shows the molecular structure of Pt(dfppy)(7a) in the crystal. Hydrogen atoms are not shown. In crystals of Pt(dfppy)(7a), the shortest intermolecular Pt—Pt separation is 6.96 Å. Similarly to the case of Pt(ppy)(7a) and Pt(ppy)(7b), any formation of stack-like agglomerates (arrangements) is prevented by the bulky ligand 7a.

Figure 8:
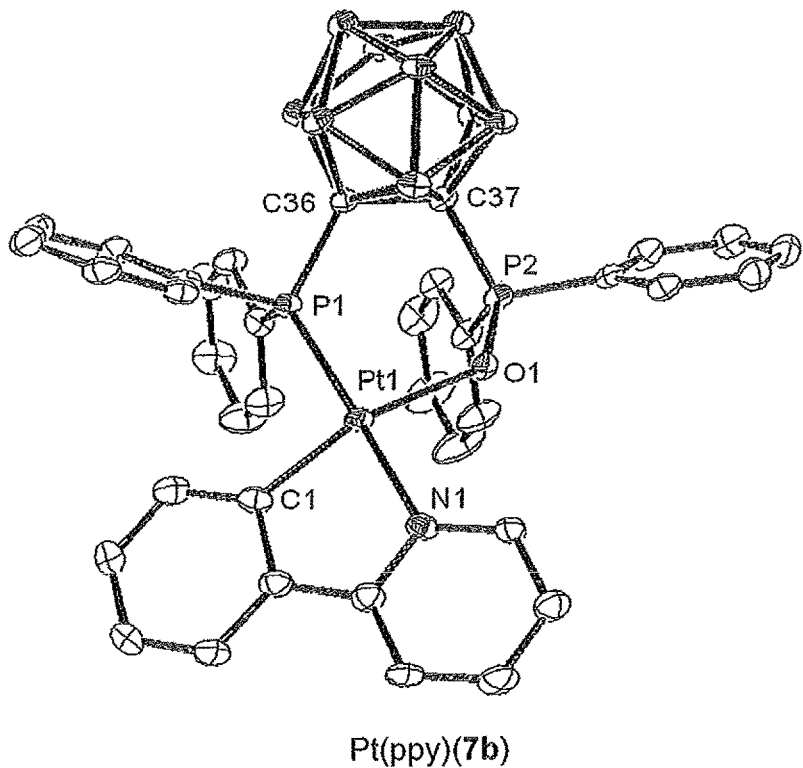

FIG. 8 shows the molecular structure of Pt(ppy)(7b) in the crystal. Hydrogen atoms are not shown. In crystals of Pt(ppy)(7b), the shortest intermolecular Pt—Pt separation is 7.86 Å, i.e. any formation of stack-like agglomerates (arrangements) is prevented by the bulky ligand 7b.

Figure 9:
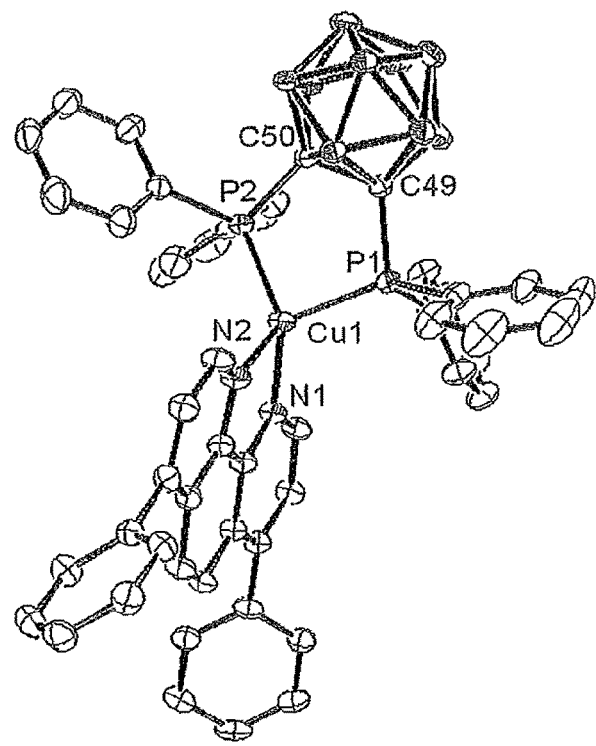

FIG. 9 shows the molecular structure of Cu(dpphen)(7a) in the crystal. Hydrogen atoms are not shown.

Figure 10:
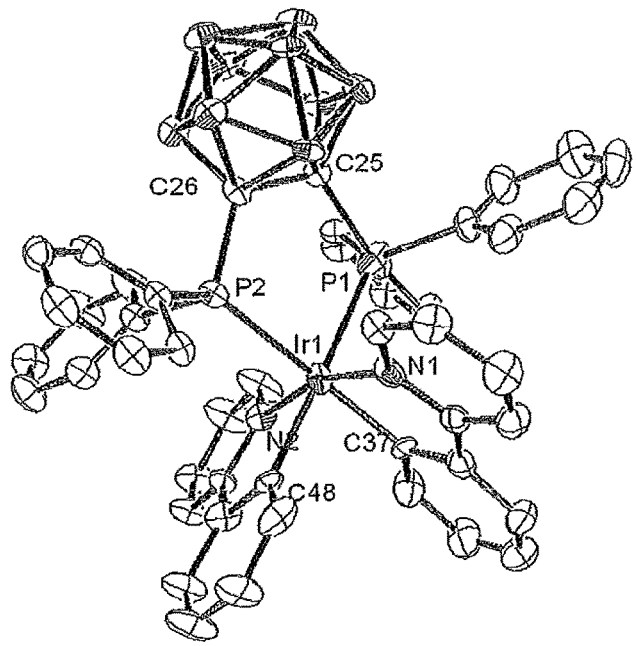

FIG. 10 shows the molecular structure of Ir(ppy)$_2$(7a) in the crystal. Hydrogen atoms are not shown.

Figure 11:
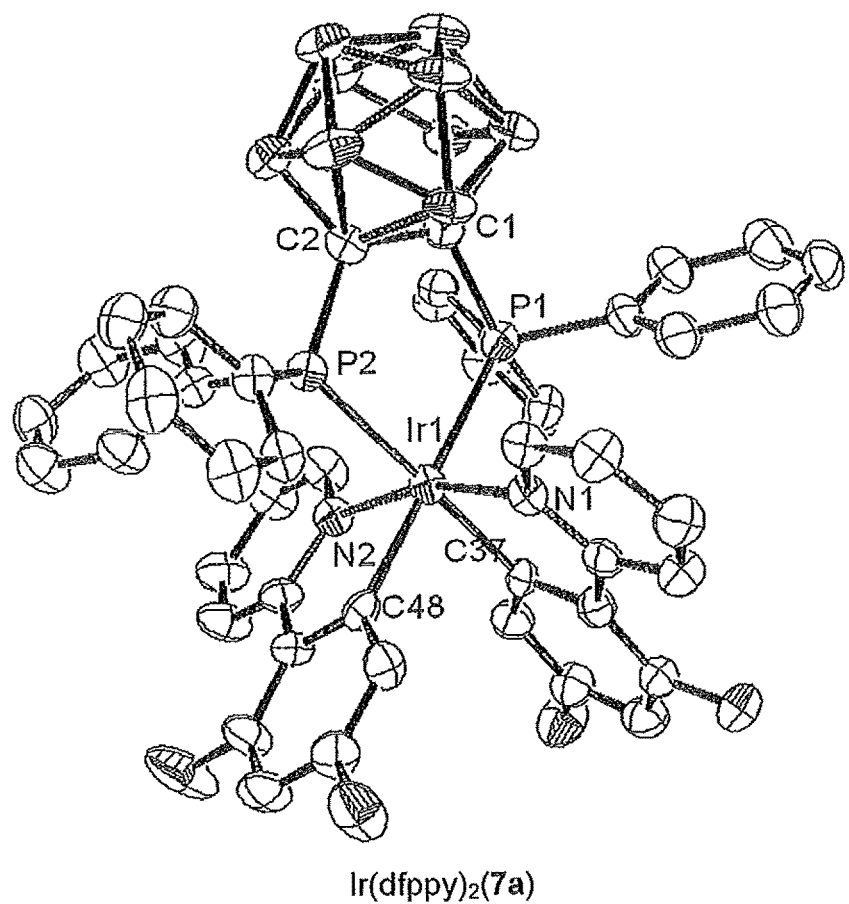

FIG. 11 shows the molecular structure of Ir(dfppy)$_2$ (7a) in the crystal. Hydrogen atoms are not shown.

Figure 12:
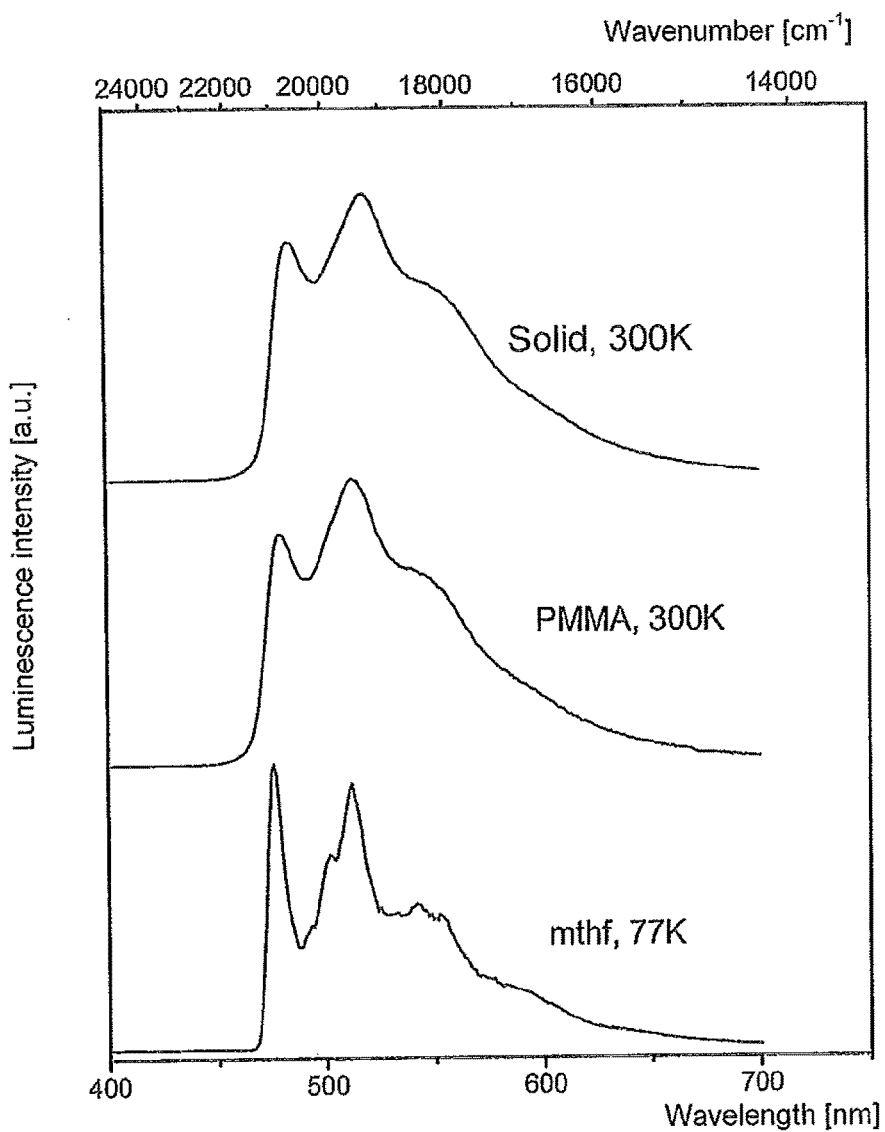

FIG. 12 shows the phosphorescence spectra of Pt(ppy)(7a) measured in 2-methyltetrahydrofuran (mthf) at T=77 K, polymethyl methacrylate (PMMA) at 300 K and of the solid (solid state) at T=300 K.

Figure 13:
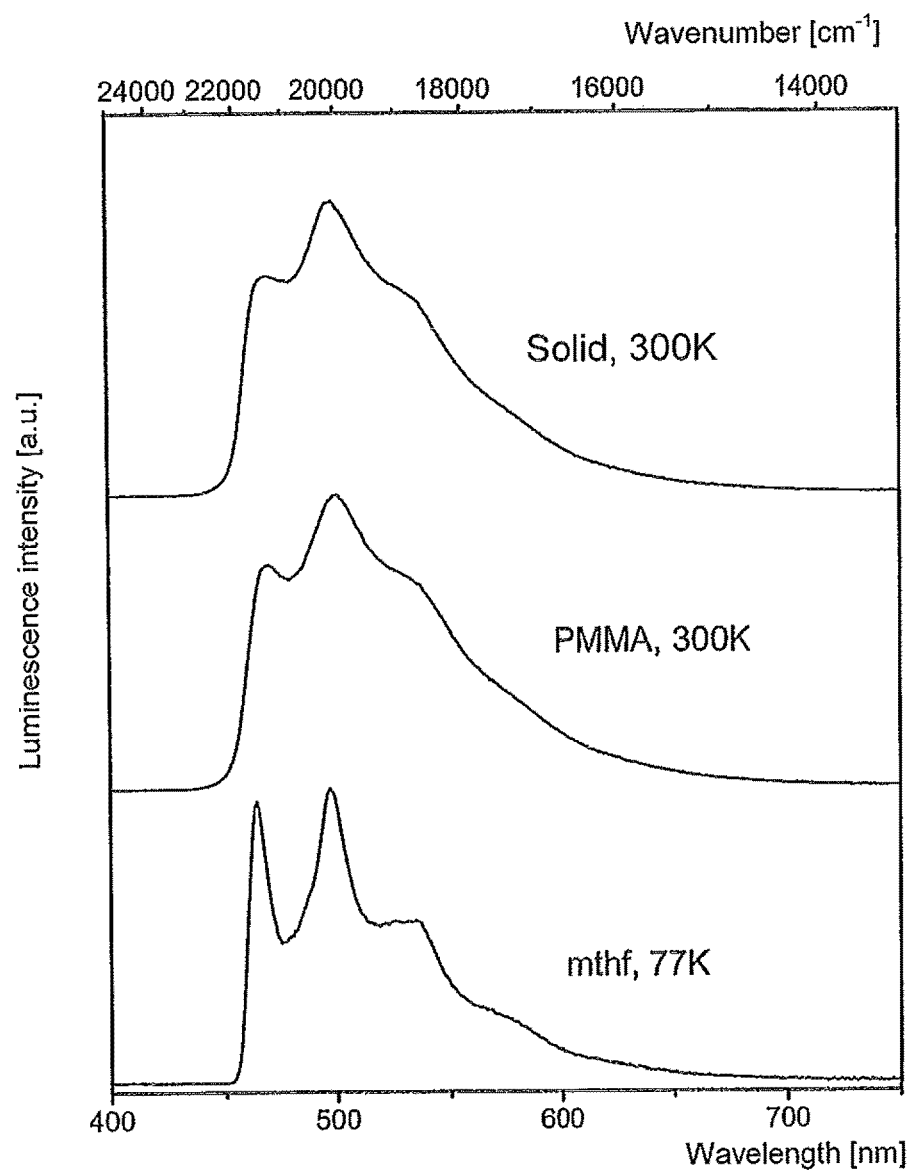

FIG. 13 shows the phosphorescence spectra of Pt(dfppy)(7a) measured in 2-methyltetrahydrofuran (mthf) at T=77 K, polymethyl methacrylate (PMMA) at 300 K and of the solid (solid state) at T=300 K.

Figure 14:
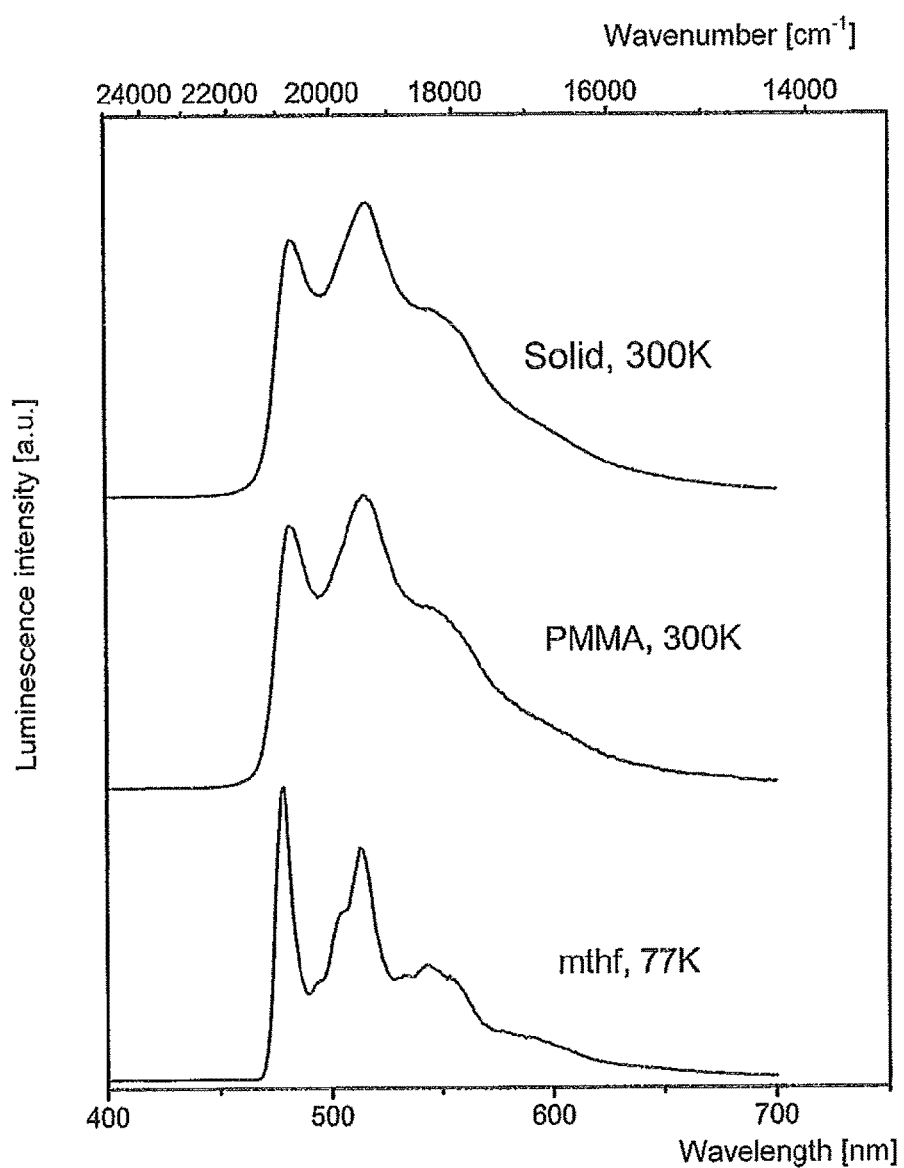

FIG. 14 shows the phosphorescence spectra of Pt(ppy)(7b) measured in 2-methyltetrahydrofuran (mthf) at T=77 K, polymethyl methacrylate (PMMA) at 300 K and of the solid (solid state) at T=300 K.

Figure 15:
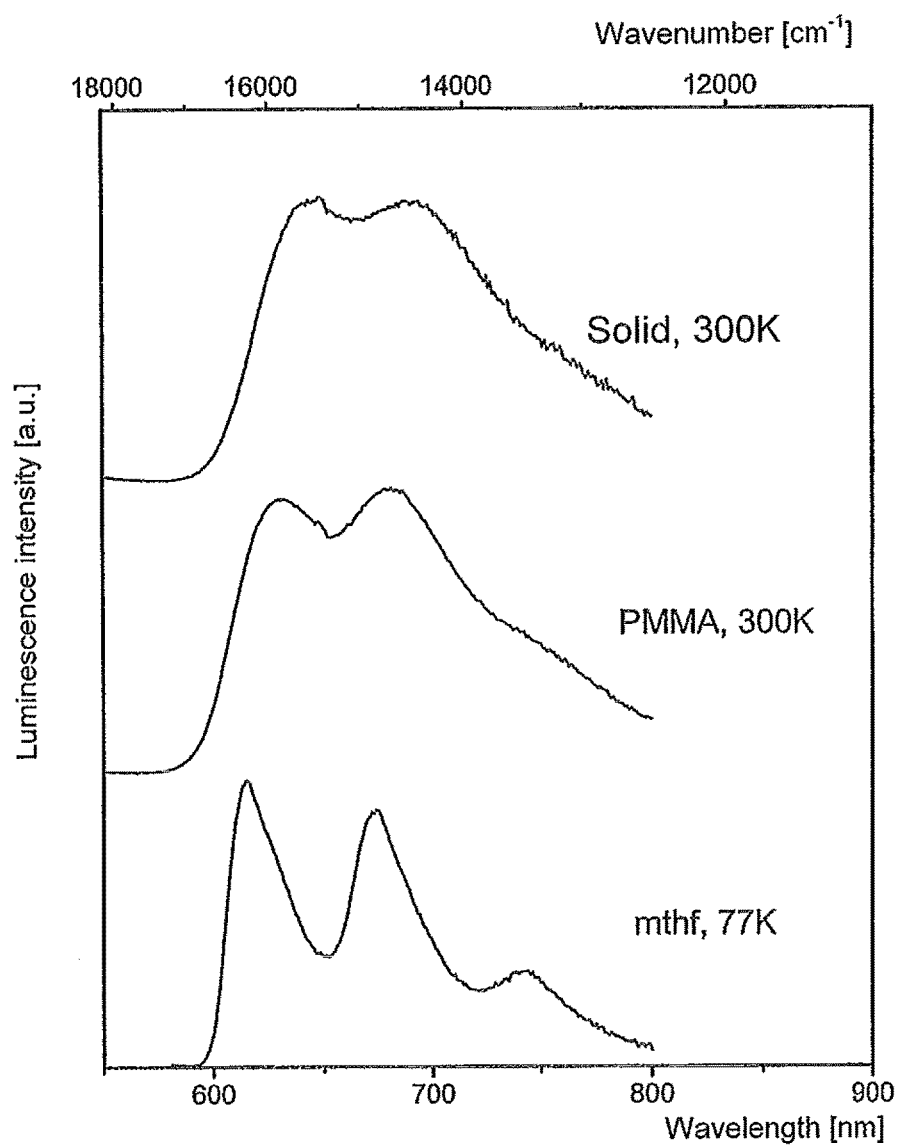

FIG. 15 shows the phosphorescence spectra of Pt(thpy)(7a) measured in 2-methyltetrahydrofuran (mthf) at T=77 K, polymethyl methacrylate (PMMA) at 300 K and of the solid (solid state) at T=300 K.

Figure 16:
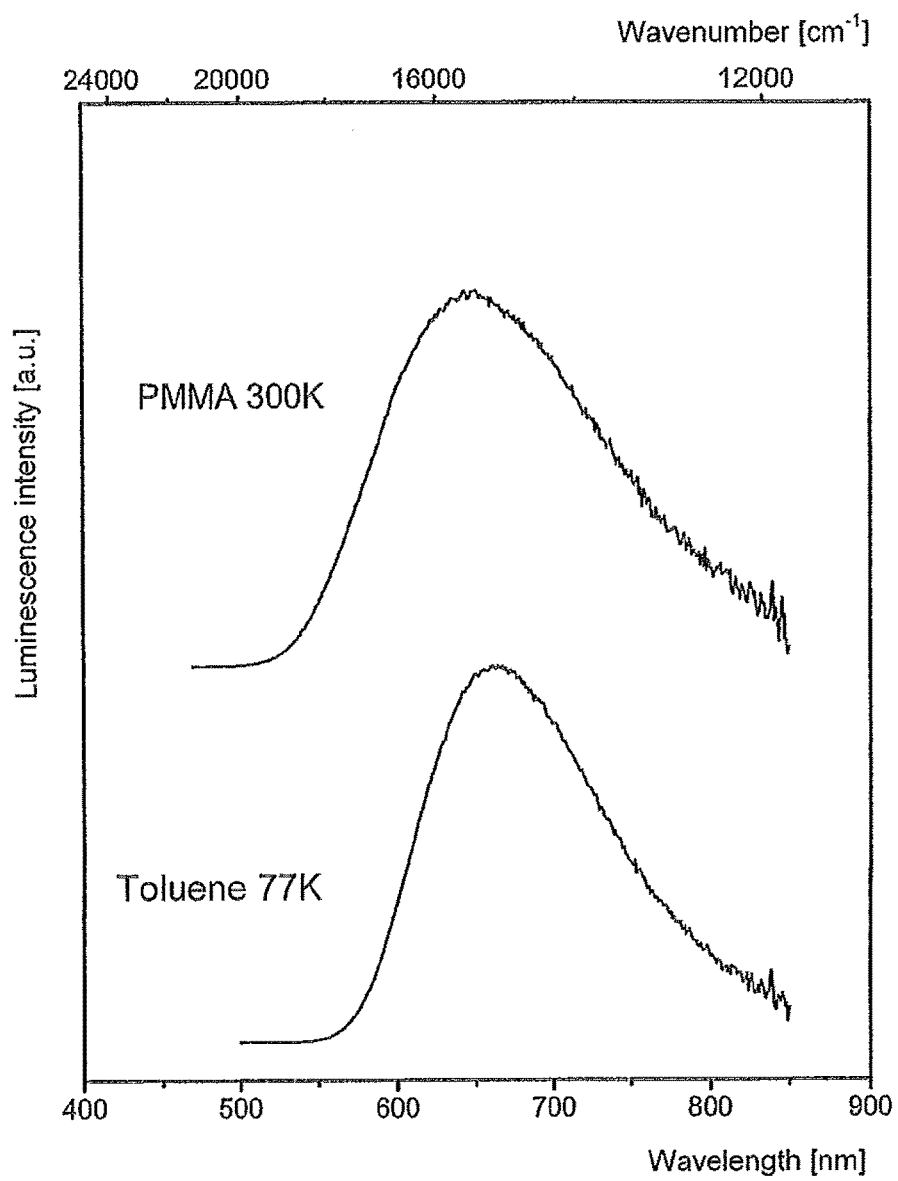

FIG. 16 shows the phosphorescence spectra of [Cu(dpphen)(7a)] measured in toluene at T=77 K and in polymethyl methacrylate (PMMA) at T=300 K.

Figure 17:
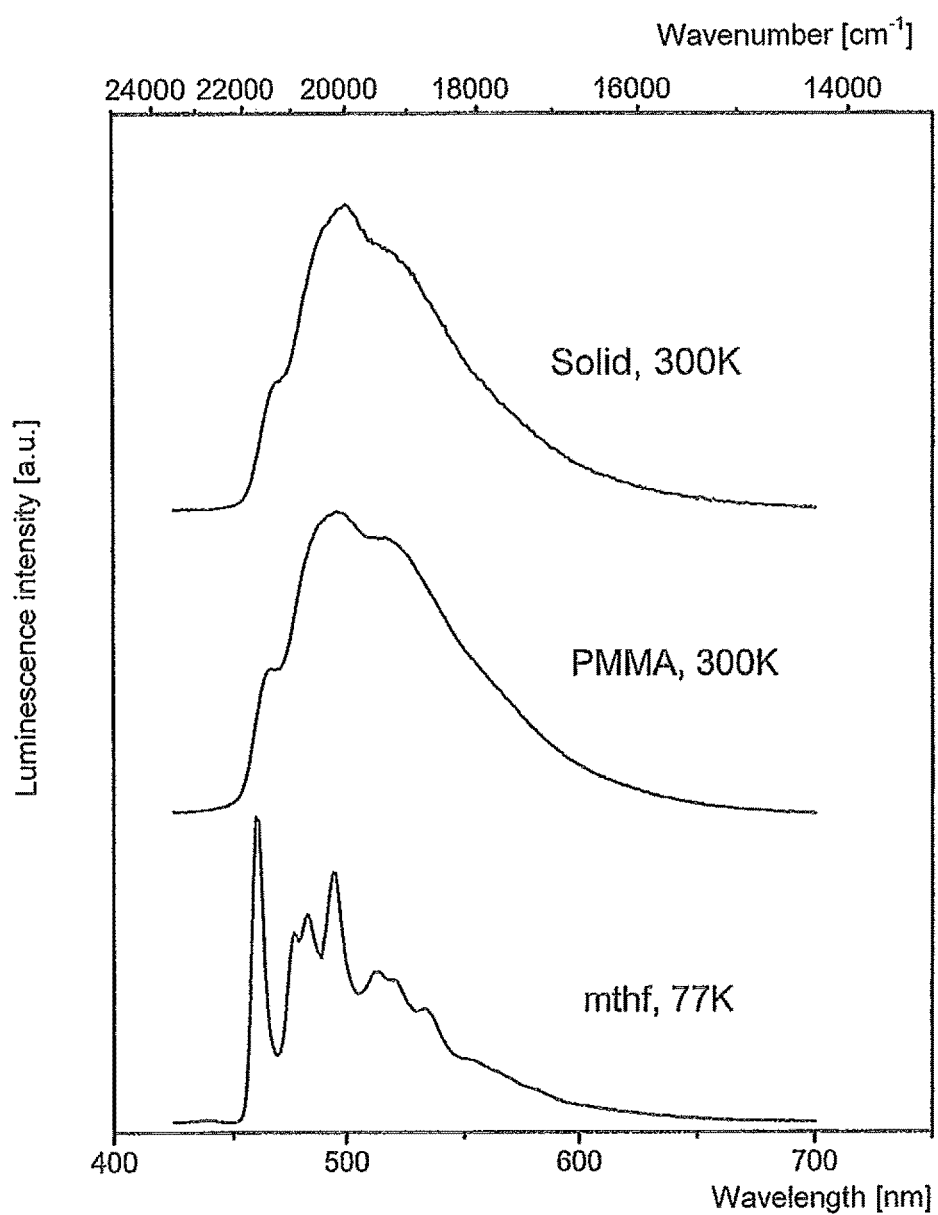

FIG. 17 shows the phosphorescence spectra of Ir(ppy)$_2$(7a) measured in 2-methyltetrahydrofuran (mthf) at T=77 K, polymethyl methacrylate (PMMA) at 300 K and of the solid (solid state) at T=300 K.

Figure 18:
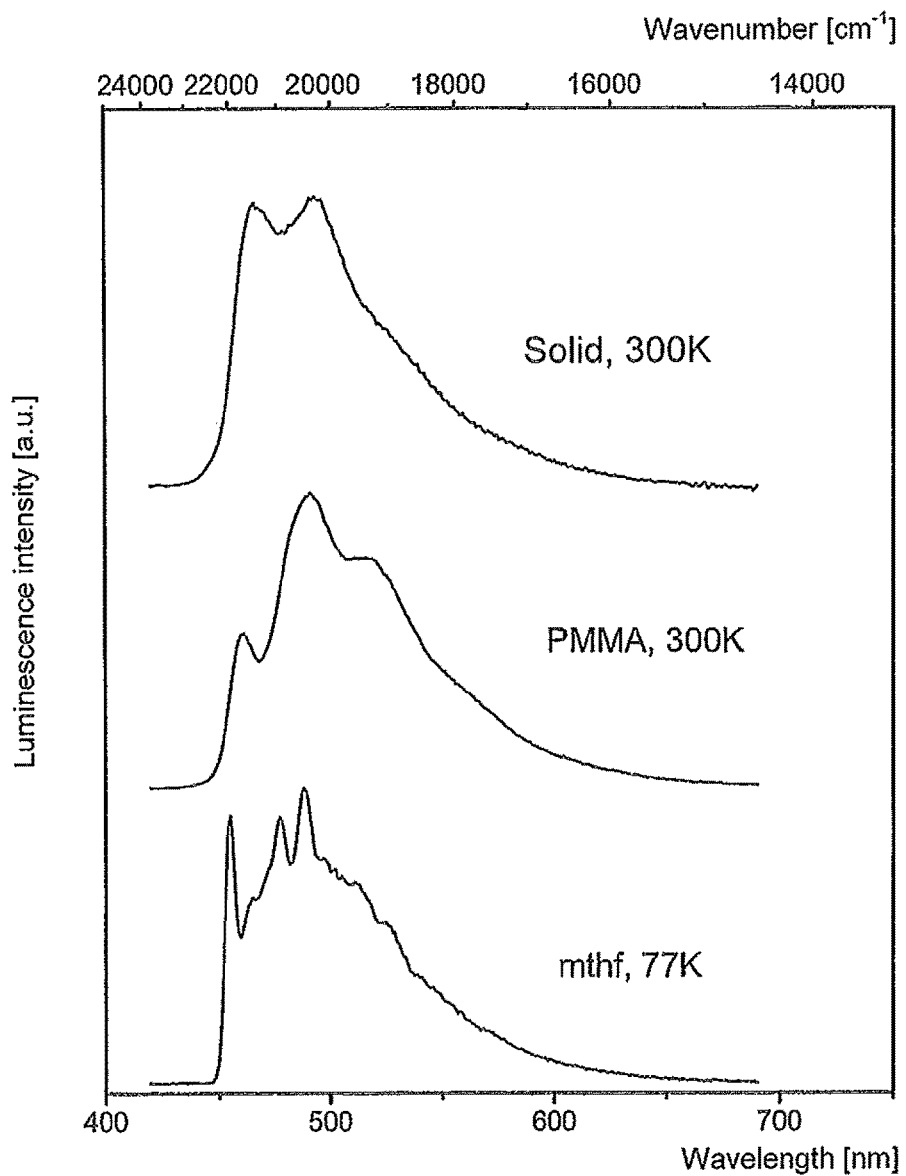

FIG. 18 shows the phosphorescence spectra of Ir(dfppy)$_2$ (7a) measured in 2-methyltetrahydrofuran (mthf) at T=77 K, polymethyl methacrylate (PMMA) at 300 K and of the solid (solid state) at T=300 K.

EXAMPLES

The syntheses of some metal complexes according to the invention are described below. The iridium and platinum complexes here are obtained in a yield of about 30-40% and the copper complexes are obtained in a yield of 90%. The purity of all complexes is >99.5%.

Example 1

Synthesis of Pt(ppy)(7a)

The complex Pt(ppy)(7a) is prepared by reaction of Pt(ppy)(ppyH)Cl and 1,2-bis(diphenylphosphine)-closo-carborane (Eq. 2). Equimolar amounts of Pt(ppy)(ppyH)Cl and 1,2-bis(diphenylphosphine)-closo-carborane are heated in ethanol under reflux under argon for 12 h. After cooling to room temperature, the crude product precipitated from the reaction mixture is purified by chromatography (Al$_2$O$_3$, hexane/dichloromethane). The purification is carried out by crystallisation from hot ethanol.

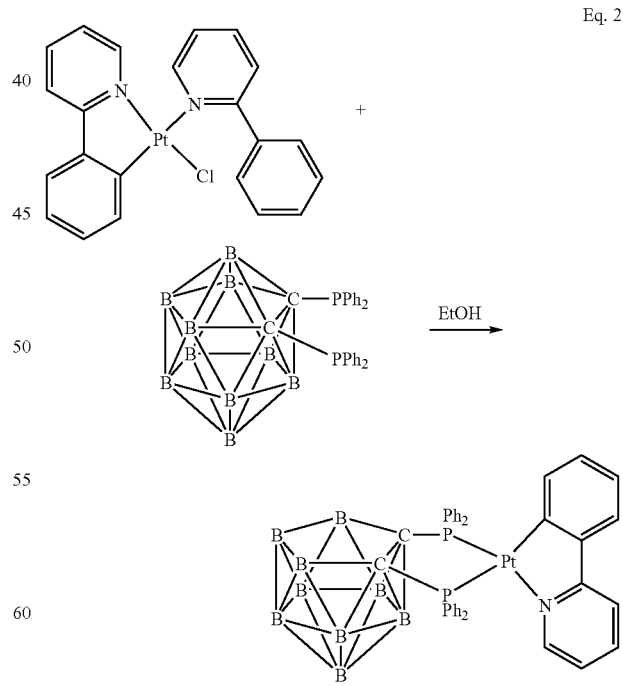

Eq. 2

The molecular structure of Pt(ppy)(7a) in the crystal is shown in FIG. 6. The photoluminescence spectra of Pt(ppy)(7a) are shown in FIG. 12.

Example 2

Synthesis of Pt(dfppy)(7a)

The complex Pt(dfppy) is prepared by reaction of Pt(dfppy)(dfppyH)Cl and 1,2-bis(diphenylphosphine)-closo-carborane (Eq. 3). A solution of equimolar amounts of Pt(dfppy)(dfppyH)Cl and 1,2-bis(diphenylphosphine)closo-carborane is stirred in refluxing ethanol under argon for 12 h. After cooling, the crude product precipitated from the reaction mixture is purified by chromatography ($Al_2O_3$, hexane/dichloromethane). In addition, the product is recrystallised from hot ethanol.

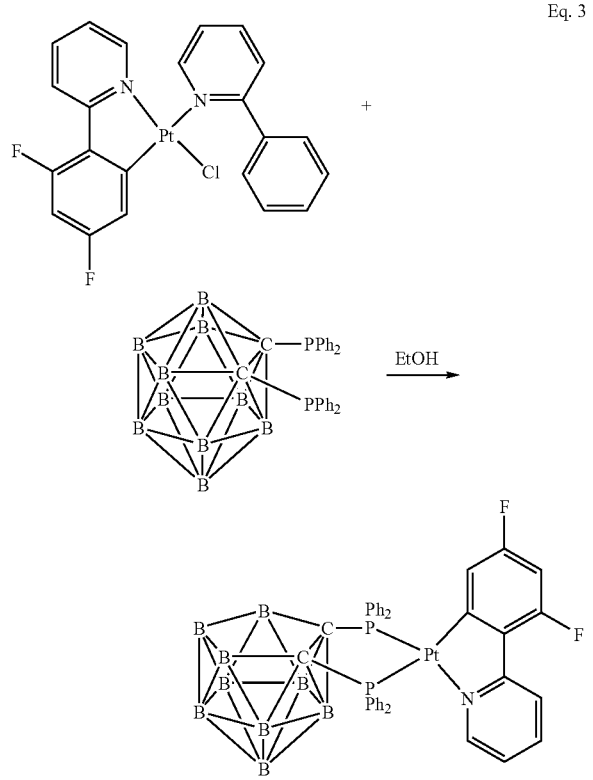

Eq. 3

The molecular structure of Pt(dfppy)(7a) in the crystal is shown in FIG. 7. The phosphorescence spectra of Pt(dfppy)(7a) are shown in FIG. 13.

Example 3

Pt(ppy)(Tb)

Chromatographic separation of the reaction mixture from Example 1 ($Al_2O_3$, hexane/dichloromethane) gives small amounts of Pt(ppy)(7b). This substance is less polar than the main product Pt(ppy)(7a).

The molecular structure of Pt(ppy)(7b) is shown in FIG. 8.
The phosphorescence spectra of Pt(ppy)(7b) are shown in FIG. 14.

Example 4

Synthesis of Pt(thpy)(7a)

The complex Pt(thpy)(7a) is prepared from Pt(thpy)(thpyH)Cl and 1,2-bis(diphenylphosphine)-closo-carborane (Eq. 4). A solution of equimolar amounts of Pt(thpy)(thpyH)Cl and 1,2-bis(diphenylphosphine)-closo-carborane is stirred in refluxing ethanol under argon for 12 h. After cooling, the crude product precipitated from the reaction mixture is purified by chromatography ($Al_2O_3$, hexane/dichloromethane). In addition, the product is recrystallised from hot ethanol.

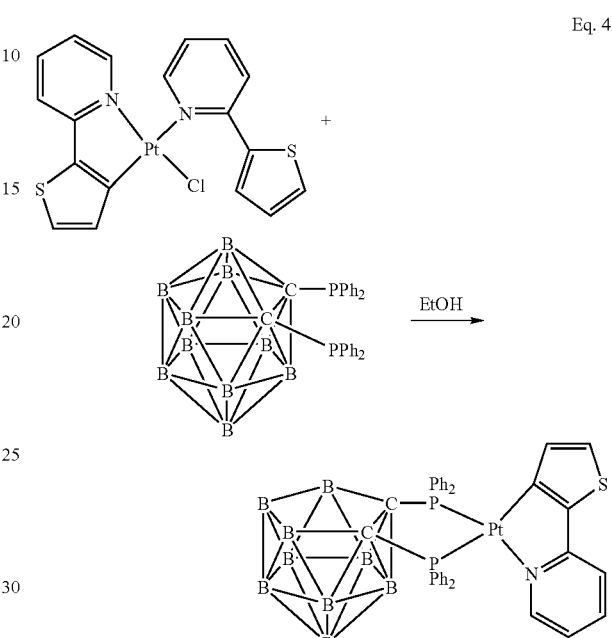

Eq. 4

The molecular structure of Pt(thpy)(7b) in the crystal is shown in FIG. 9.

The phosphorescence spectra of Pt(thpy)(7b) are shown in FIG. 15.

Example 5

Synthesis of Cu(dphen)(7a), (dpphen=4,7-diphenylphenanthroline)

The complex Cu(dpphen)(7a) is prepared from [Cu(CH$_3$CN)$_4$]PF$_6$, 7a and dpphen (Eq. 5). A solution of equimolar amounts of [Cu(CH$_3$CN)$_4$]PF$_6$ and tetrabutylammonium 7,8-bis(diphenylphosphino)-7,8-dicarba-nido-undecaborate ([NBu$_4$](7a)) is stirred in dichloromethane under argon for 2 h. An equimolar amount of dpphen is added to this solution of [Cu(CH$_3$CN)$_2$ (7a)] prepared in situ. When the solution has become an intense red colour, the reaction mixture is chromatographed (SiO$_2$, CH$_2$Cl$_2$). The further purification is carried out by crystallisation from dichloromethane/hexane.

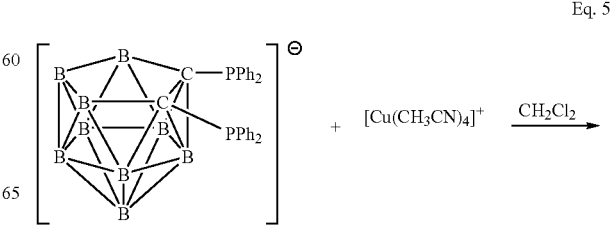

Eq. 5

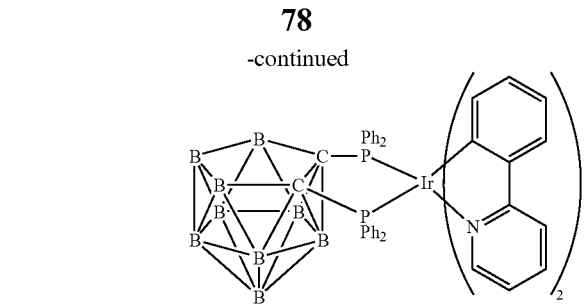

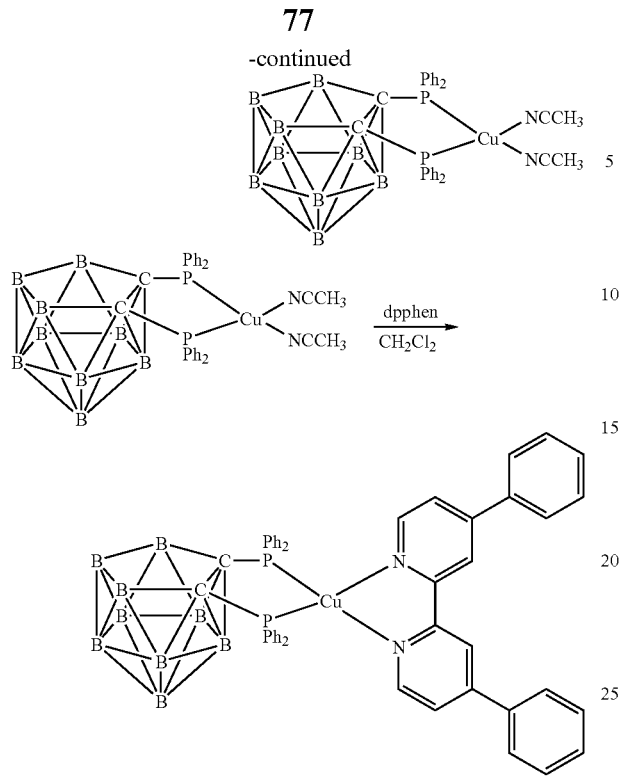

The molecular structure of Cu(dpphen)(7a) in the crystal is shown in FIG. 9. The photoluminescence spectra of Cu(dpphen)(7a) are shown in FIG. 16.

Example 6

Synthesis of Ir(ppy)$_2$ (7a)

The complex Ir(ppy)$_2$(7a) is prepared by reaction of [Ir(ppy)$_2$Cl]$_2$ and 1,2-bis(diphenylphosphine)-closo-carborane (Eq. 6). A solution of [Ir(ppy)$_2$Cl]$_2$ and twice the molar amount of 1,2-bis(diphenylphosphine)-closo-carborane is stirred in ethanol under reflux under argon for 48 h. After cooling, the crude product precipitated from the reaction mixture is purified by chromatography (Al$_2$O$_3$, diethyl ether/dichloromethane). In addition, the product is recrystallised from dichloromethane/diethyl ether.

The molecular structure of Ir(ppy)$_2$(7a) in the crystal is shown in FIG. 10.

The phosphorescence spectra of Ir(ppy)$_2$(7a) are shown in FIG. 17.

Example 7

Synthesis of Ir(dfppy)$_2$(7a)

The complex Ir(dfppy)$_2$(7a) is prepared by reaction of [Ir(dfppy)$_2$Cl]$_2$ and 1,2-bis(diphenylphosphine)-closo-carborane (Eq. 7). A solution of [Ir(dfppy)$_2$Cl]$_2$ and twice the molar amount of 1,2-bis(diphenylphosphine)closo-carborane is stirred in ethanol under reflux under argon for 48 h. After cooling, the crude product precipitated from the reaction mixture is purified by chromatography (Al$_2$O$_3$, diethyl ether/dichloromethane). In addition, the product is recrystallised from dichloromethane/diethyl ether.

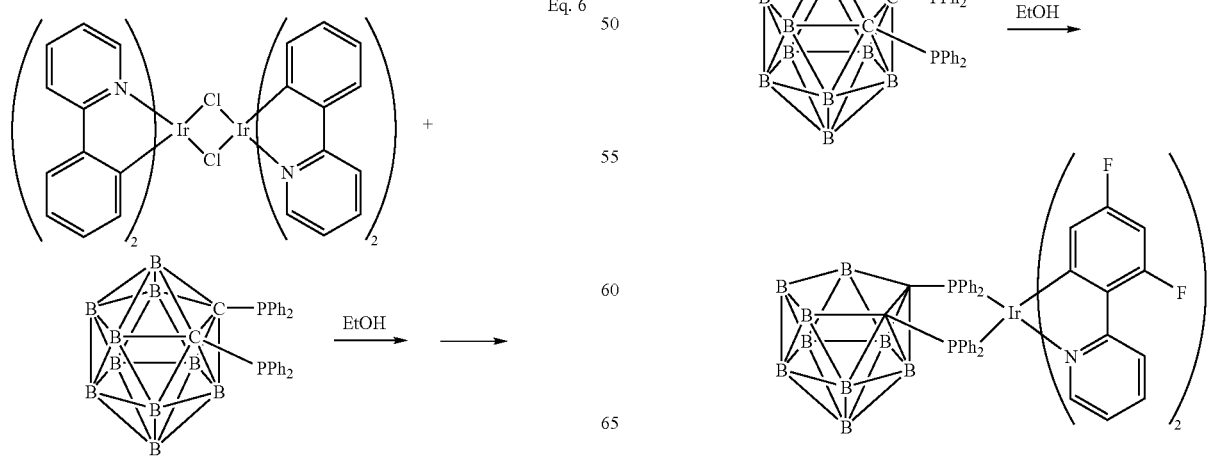

The molecular structure of Ir(dfppy)₂(7a) in the crystal is shown in FIG. 11. The phosphorescence spectra of Ir(dfppy)₂(7a) are shown in FIG. 18.

Example 8

Synthesis of Ir(3-piq)₂(7a)

The complex Ir(3-piq)₂(7a) (3-piq=3-phenylisoquinoline) is prepared by reaction of [Ir(3-piq)₂Cl]₂ and 1,2-bis(diphenylphosphine)-closo-carborane (Eq. 8). A solution of [Ir(3-piq)₂Cl]₂ and twice the molar amount of 1,2-bis(diphenylphosphine)-closo-carborane is stirred in ethanol under reflux under argon for 48 h. After cooling, the crude product precipitated from the reaction mixture is purified by chromatography (Al₂O₃, diethyl ether/dichloromethane). In addition, the product is recrystallised from dichloromethane/diethyl ether.

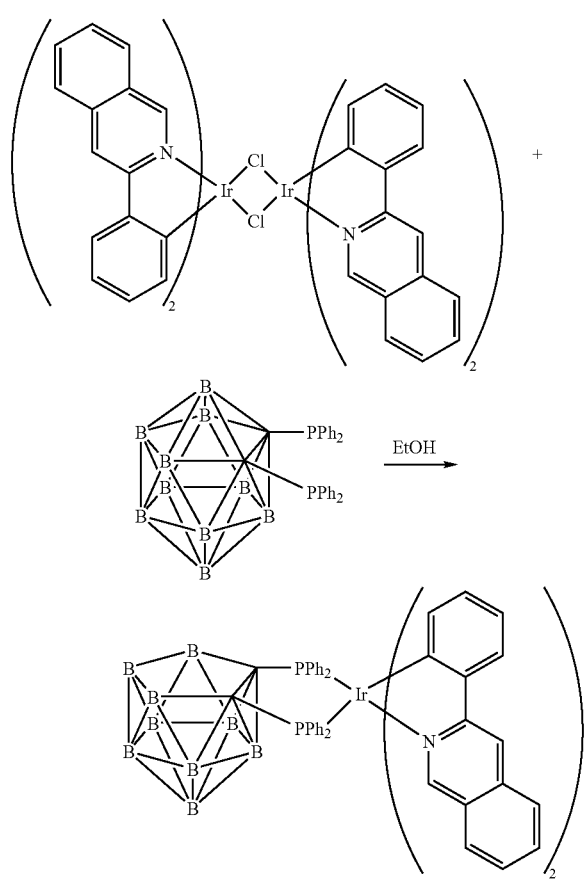

Eq. 8

Example 9

Synthesis of Ir(1-piq)₂(7a)

The complex Ir(1-piq)₂(7a) (1-piq=1-phenylisoquinoline) is prepared by reaction of [Ir(1-piq)₂Cl]₂ and 1,2-bis(diphenylphosphine)-closo-carborane (Eq. 9). A solution of [Ir(1-piq)₂Cl]₂ and twice the molar amount of 1,2-bis(diphenylphosphine)-closo-carborane is stirred in ethanol under reflux under argon for 48 h. After cooling, the crude product precipitated from the reaction mixture is purified by chromatography (Al₂O₃, diethyl ether/dichloromethane). In addition, the product is recrystallised from dichloromethane/diethyl ether.

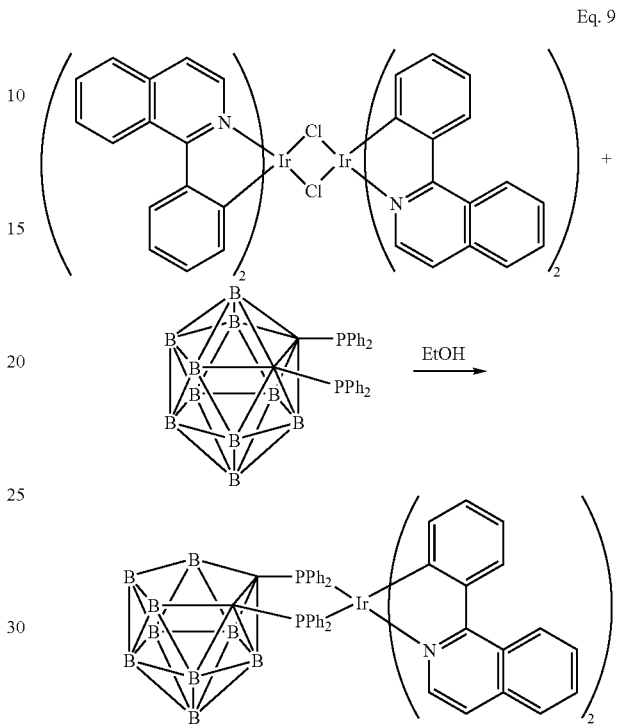

Eq. 9

Production and Characterisation of Organic Electroluminescent Devices:

LEDs are produced by the general process outlined below. This must of course be matched to the particular circumstances in individual cases (for example layer-thickness variation in order to achieve optimum efficiency or colour).

General Process for the Production of OLEDs:

After the ITO-coated substrates (for example glass support, PET film) have been cut to the correct size, they are cleaned in a number of cleaning steps in an ultrasound bath (for example soap solution, Millipore water, isopropanol). For drying, they are blown off using an N₂ gun and stored in a desiccator. Before coating with the organic layers by vapour deposition, they are treated with an ozone plasma device for about 20 minutes. It may be advisable to use a polymeric hole-injection layer as the first organic layer. This is generally a conjugated, conductive polymer, such as, for example, a polyaniline derivative (PANI) or a polythiophene derivative (for example PEDOT, BAYTRON P™ from BAYER). This is then applied by spin coating. The organic layers are applied one after the other by vapour deposition in a high-vacuum unit. The layer thickness of the respective layer and the vapour-deposition rate are monitored or set via a quartz resonator. It is also possible for individual layers to consist of more than one compound, i.e. generally a host material doped with a guest material. This is achieved by co-evaporation from two or more sources. An electrode is then applied to the organic layers. This is generally carried out by thermal evaporation (Balzer BA360 or Pfeiffer PL S 500). The transparent ITO electrode is subsequently connected as the anode and the metal electrode is connected as the cathode, and the device parameters are determined.

OLEDs having the following structure 1 are produced analogously to the above-mentioned general process:

PEDOT 20 nm (spin-coated from water; PEDOT purchased from BAYER AG; poly[3,4-ethylenedioxy-2,5-thiophene])
HIM1 20 nm of 2,2',7,7'-tetrakis(di-p-tolylamino)spiro-9,9'-bifluorene (vapour-deposited)
NPB 20 nm of 4,4'-bis(1-naphthylphenylamino)biphenyl (vapour-deposited)
mCP 40 nm of 1,3-bis(N-carbazolyl)benzene (vapour-deposited) doped with 10% of
emitter examples according to the invention, see Table 4
BCP 5 nm of 2,9-dimethyl-4,7-diphenyl-1,10-phenanthroline (vapour-deposited)
AlQ$_3$ 30 nm of aluminium(III) tris(hydroxyquinolinate) (vapour-deposited)
Li/Al 5 nm of LiF, 150 nm of Al on top as cathode.

This as yet unoptimised OLED is characterised by standard methods. Table 4 shows the efficiency and the voltage at 500 cd/m$^2$ as well as the colour.

TABLE 4

| Ex. | Emitter | Efficiency [cd/A] at 500 cd/m$^2$ | Voltage [V] at 500 cd/m$^2$ | Colour CIE x/y |
|---|---|---|---|---|
| 10 | Example 1 | 16.4 | 5.6 | 0.28/0.61 |
| 11 | Example 2 | 12.3 | 6.8 | 0.19/0.34 |
| 12 | Example 6 | 26.5 | 5.4 | 0.31/0.59 |
| 13 | Example 7 | 14.9 | 6.6 | 0.18/0.33 |

Furthermore, OLEDs having the following structure 2 are produced analogously to the above-mentioned general process:

PEDOT 20 nm (spin-coated from water; PEDOT purchased from BAYER AG; poly[3,4-ethylenedioxy-2,5-thiophene]
PVK 60 nm (spin-coated from chlorobenzene, PVK Mw=1, 100,000, purchased from Aldrich, solution comprising 5% by weight of emitter, see Table 5)
Ba/Ag 10 nm of Ba/150 nm of Ag as cathode.

This as yet unoptimised OLED is characterised by standard methods. Table 5 shows the efficiency and the voltage at 500 cd/m$^2$ as well as the colour.

TABLE 5

| Ex. | Emitter | Efficiency [cd/A] at 500 cd/m$^2$ | Voltage [V] at 500 cd/m$^2$ | Colour CIE x/y |
|---|---|---|---|---|
| 14 | Example 4 | 9.6 | 4.8 | 0.64/0.35 |
| 15 | Example 5 | 4.3 | 5.2 | 0.63/0.36 |
| 16 | Example 8 | 8.1 | 4.6 | 0.67/0.32 |
| 17 | Example 9 | 7.3 | 4.6 | 0.69/0.31 |

The invention claimed is:

1. An organic electronic device comprising an anode, a cathode, at least one layer which comprises at least one organic compound, and at least one metal complex, wherein said at least one metal complex comprises at least one ligand of formula (I)

$[7,8\text{-}(ER_2)_2\text{-}7,8\text{-}C_2B_9(R^1)_{10}]$ (I)

wherein
E is, identically or differently on each occurrence, P, As, Sb, and N;
R is, identically or differently on each occurrence, H, deuterium, F, N(R$^2$)$_2$, a straight-chain alkyl, alkoxy or thioalkoxy group having 1 to 40 C atoms and optionally substituted by one or more radicals R$^2$ or a branched or cyclic alkyl, alkoxy or thioalkoxy group having 3 to 40 C atoms and optionally substituted by one or more radicals R$^2$ wherein one or more H atoms of said straight-chain, branched, or cyclic alkyl, alkoxy, and thioalkoxy groups are optionally replaced by F, CN, an aromatic or heteroaromatic ring system having 5 to 60 aromatic ring atoms and optionally substituted by one or more radicals R$^2$, or an aryloxy or heteroaryloxy group having 5 to 60 aromatic ring atoms and optionally substituted by one or more radicals R$^2$, or a combination of these systems, and wherein two or more substituents R together optionally define a mono- or polycyclic, aliphatic, aromatic, and/or benzo-fused ring system;
R$^1$ is, identically or differently on each occurrence, H, OH, or a C$_1$-C$_{30}$-alkoxy group;
R$^2$ is, identically or differently on each occurrence, H, F, or an aliphatic, aromatic, and/or heteroaromatic hydrocarbon radical having 1 to 20 C atoms, wherein one or more H atoms of said aliphatic, aromatic, and/or heteroaromatic hydrocarbon radicals are optionally replaced by F, and wherein two or more substituents R$^2$ together optionally define a mono- or polycyclic, aliphatic, aromatic, and/or benzo-fused ring system;
wherein said organic electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and OLED sensors.

2. The organic electronic device of claim 1, wherein said ligand of formula (I) is selected from the group consisting of:
ligands wherein both E are P, As, Sb, or N:

$[7,8\text{-}(PR_2)_2\text{-}7,8\text{-}C_2B_9H_{10}]$ (Ia)

$[7,8\text{-}(AsR_2)_2\text{-}7,8\text{-}C_2B_9H_{10}]$ (Ia')

$[7,8\text{-}(SbR_2)_2\text{-}7,8\text{-}C_2B_9H_{10}]$ (Ia'')

$[7,8\text{-}(NR_2)_2\text{-}7,8\text{-}C_2B_9H_{10}]$ (Ia''')

and corresponding ligands wherein each E is different and is selected from the group consisting of P, As, Sb, and N.

3. The organic electronic device of claim 1, wherein said at least one metal complex is a complex of formula (II)

$M(E\cap E)_x(A\cap A^{n-})_y(L)_z$ (II)

wherein
M is a metal;
(E∩E) is a ligand of formula (I);
(A∩A$^{n-}$) is a bi- or polydentate ligand;
L is a mono- or polydentate ligand;
x is 1, 2, or 3;
y is 0, 1, 2, or 3;
z is 0, 1, 2, or 3; and
n is 0, 1, or 2.

4. The metal complex of claim 3, wherein M is a transition metal and y is 1, 2, or 3.

5. The metal complex of claim 4, wherein M is selected from the group consisting of W, Re, Os, Ir, Pt, Ru, Rh, Cu, and lanthanides and y is 1 or 2.

6. The organic electronic device of claim 3, wherein said ligands L are selected from the group consisting of carbon monoxide, nitrogen monoxide, isonitriles, nitriles, amines, imines, phosphines, phosphites, arsines, stibines, thioethers, nitrogen-containing heterocyclic compounds, hydride, deuteride, F, Cl, Br, I, alkylacetylides, arylacetylides, cyanide, cyanate, isocyanate, thiocyanate, isothiocyanate, nitrate, nitrite, aliphatic or aromatic alcoholates, aliphatic or aromatic thioalcoholates, amides, carboxylates, alkyl groups, aryl groups, $O^{2-}$, $S^{2-}$, nitrenes, $N^{3-}$, diamines, diimines, heterocyclic compounds containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates, and borates of nitrogen-containing heterocyclic compounds.

7. The organic electronic device of claim 3, wherein $(A \cap A''^-)$ is bonded to the metal in the complex via least one carbon atom and/or via at least one nitrogen atom, wherein said at least one carbon atom is optionally a carbene.

8. The organic electronic device of claim 3, wherein $(A \cap A''^-)$ comprises aromatic or heteroaromatic groups which coordinate to the metal, wherein said aromatic or heteroaromatic groups are aryl or heteroaryl groups having 5 to 40 aromatic ring atoms, are optionally identical or different on each occurrence, are optionally substituted by one or more radicals R, and optionally comprise an exocyclic donor atom.

9. The organic electronic device of claim 8, wherein said aromatic or heteroaromatic coordinating groups in $(A \cap A''^-)$ are selected from the following formulae, wherein two of these groups are bonded to one another, in each case, at the position denoted by # and * denotes, in each case, the position at which the ligand is bonded to the metal:

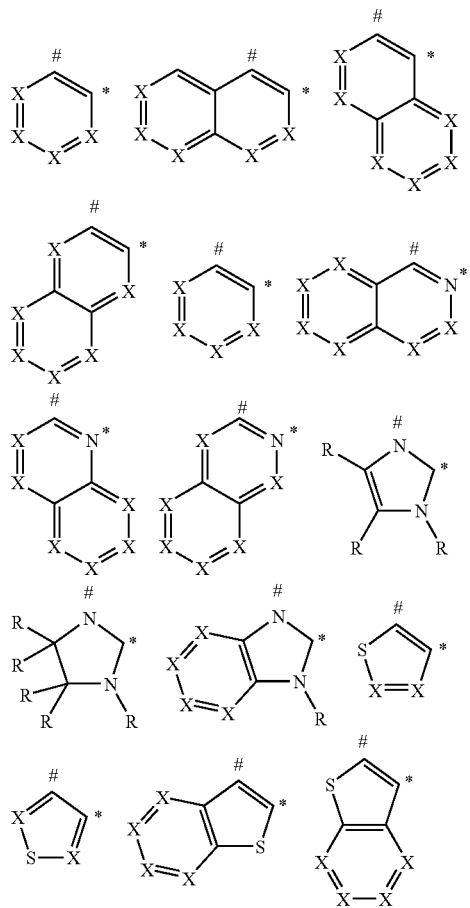

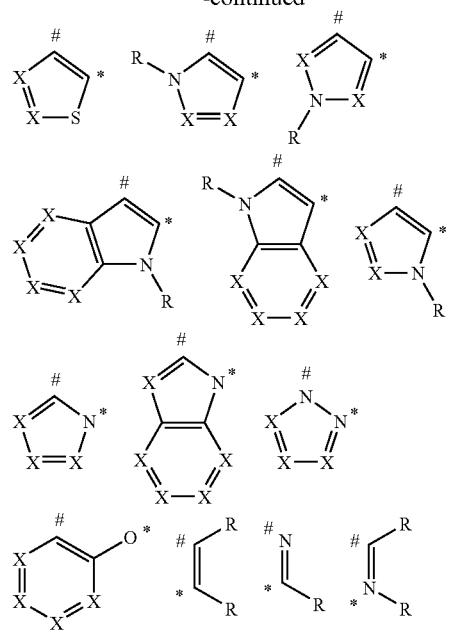

wherein
X is, identically or differently on each occurrence, CR, wherein R is as defined in claim 1, or N, with the proviso that, when a group contains more than three ring members X, no more than three of said ring members X in said group is N.

10. The organic electronic device of claim 3, wherein said at least one metal complex of formula (II) is selected from the group consisting of $M(E \cap E)(A \cap A''^-)_2$, $M(E \cap E)_2(A \cap A''^-)$, and $M(E \cap E)(A \cap A''^-)(L)_2$.

11. The organic electronic device of claim 3, wherein said at least one metal complex of formula (II) is selected from the group consisting of complexes of formulae (III), (IV), (V), and (VI):

$$M(III)(E \cap E)_3 \qquad (III)$$

$$M(III)(E \cap E)_3(L)_z \qquad (IV)$$

$$M(II)(E \cap E)_2(L)_z \qquad (V)$$

$$M(III)(E \cap E)_3(N \cap N)(L)_z \qquad (VI)$$

wherein
$(N \cap N)$ is a bidentate ligand which coordinates to the metal via two nitrogen atoms;
M(III) is a trivalent lanthanoid cation;
M(II) is a divalent lanthanoid cation;
$(E \cap E)$ is a ligand of formula (I); and
L is a mono- or polydentate ligand.

12. The organic electronic device of claim 11, wherein $(N \cap N)$ is a ligand having the following structure:

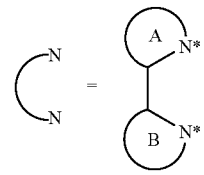

wherein A and B are five- or six-atom rings or are open-chain.

13. The organic electronic device of claim 12, wherein groups A and B here are selected from the following groups:

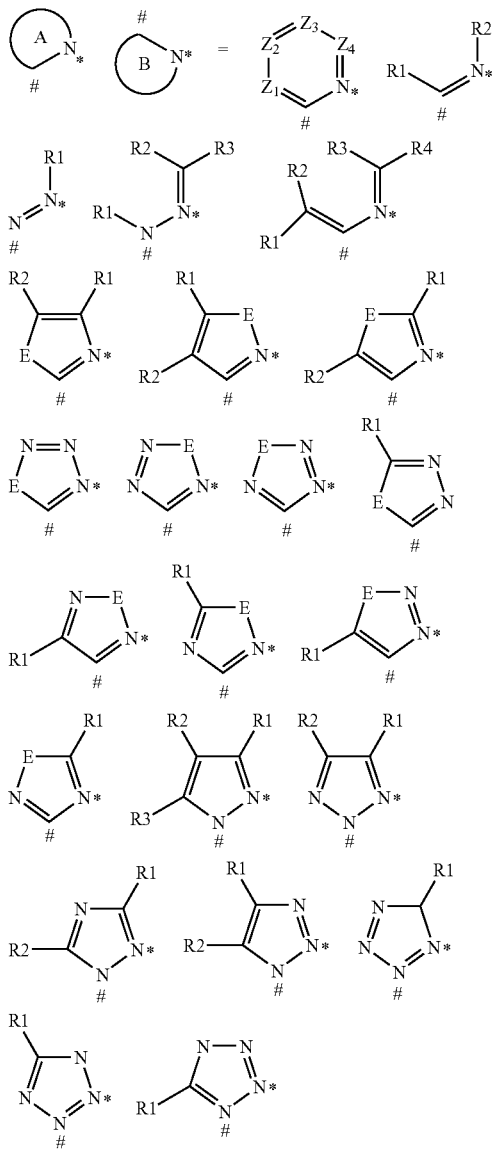

wherein
R is as defined in claims 1;
R1, R2, R3, and R4
   have the same definition as R;
E is O, S, or NR; and
$Z_1$, $Z_2$, $Z_3$, and $Z_4$
   are, identically or differently on each occurrence, CR or N;
and wherein * denotes the atom which bonds to the complex and # denotes the atom which bonds to the second unit.

14. The organic electronic device of claim 1, further comprising a cathode, an anode, and at least one emitting layer, and optionally comprising one or more further layers selected from the group consisting of hole-injection layers, hole-transport layers, hole-blocking layers, electron-transport layers, electron-injection layers, exciton-blocking layers, charge-generation layers, organic p/n junctions, and inorganic p/n junctions.

15. The organic electronic device of claim 1, wherein said at least one metal complex is employed as an emitting compound in an emitting layer, either as a pure substance or in combination with a matrix material.

16. The organic electronic device of claim 15, wherein said matrix material is selected from the group consisting of N,N-biscarbazolylbiphenyl, carbazole derivatives, polyvinylcarbazole, azacarbazoles, ketones, phosphine oxides, sulfoxides, sulfones, oligophenylenes, aromatic amines, bipolar matrix materials, silanes, azaboroles, and boronic esters.

17. A metal complex of formula (II)

$$M(E \cap E)_x (A \cap A^{n-})_y (L)_z \qquad (II)$$

wherein
M is a metal;
(E∩E) is a ligand of formula (I)

$$[7,8\text{-}(ER_2)_2\text{-}7,8\text{-}C_2B_9(R^1)_{10}] \qquad (I)$$

wherein
E is, identically or differently on each occurrence, P, As, Sb, and N;
R is, identically or differently on each occurrence, H, deuterium, F, $N(R^2)_2$, a straight-chain alkyl, alkoxy or thioalkoxy group having 1 to 40 C atoms and optionally substituted by one or more radicals $R^2$ or a branched or cyclic alkyl, alkoxy or thioalkoxy group having 3 to 40 C atoms and optionally substituted by one or more radicals $R^2$, wherein one or more H atoms of said straight-chain, branched, or cyclic alkyl, alkoxy, and thioalkoxy groups are optionally replaced by F, CN, an aromatic or heteroaromatic ring system having 5 to 60 aromatic ring atoms and optionally substituted by one or more radicals $R^2$, or an aryloxy or heteroaryloxy group having 5 to 60 aromatic ring atoms and optionally substituted by one or more radicals $R^2$, or a combination of these systems, and wherein two or more substituents R together optionally define a mono- or polycyclic, aliphatic, aromatic, and/or benzo-fused ring system;
$R^1$ is, identically or differently on each occurrence, H, OH, or a $C_1$-$C_{30}$-alkoxy group; and
$R^2$ is, identically or differently on each occurrence, H, F, or an aliphatic, aromatic, and/or heteroaromatic hydrocarbon radical having 1 to 20 C atoms, wherein one or more H atoms of said aliphatic, aromatic, and/or heteroaromatic hydrocarbon radicals are optionally replaced by F, and wherein two or more substituents $R^2$ together optionally define a mono- or polycyclic, aliphatic, aromatic, and/or benzo-fused ring system;
$(A \cap A^{n-})$ is a bi-or polydentate ligand, wherein $(A \cap A^{n-})$ is not a ligand of formula (I);
L is a mono- or polydentate ligand,
x is 1, 2, or 3;
y is 1, 2, or 3;
z is 0, 1, 2, or 3; and
n is 0, 1, or 2.

18. The metal complex of claim 17, wherein M is a transition metal, $(A \cap A^{n-})$ has at least one metal-carbon bond to the metal, x is 1 or 2, and y is 1 or 2.

19. The metal complex of claim 18, wherein M is selected from the group consisting of W, Re, Os, Ir, Pt, Ru, Rh, Cu, and lanthanides.

20. A metal complex of formula (III), (IV), (V), or (VI), $$M(III)(E \cap E)_3 \quad (III)$$

$$M(III)(E \cap E)_3(L)_z \quad (IV)$$

$$M(II)(E \cap E)_2(L)_z \quad (V)$$

$$M(III)(E \cap E)_3(N \cap N)(L)_z \quad (VI)$$

wherein
(N∩N) is a bidentate ligand coordinated to the metal via two nitrogen atoms;
M(III) is a trivalent lanthanoid cation;
M(II) is a divalent lanthanoid cation;
(E∩E) is a ligand of formula (I)

$$[7,8-(ER_2)_2-7,8-C_2B_9(R^1)_{10}] \quad (I)$$

wherein
E is, identically or differently on each occurrence, P, As, Sb, and N;
R is, identically or differently on each occurrence, H, deuterium, F, $N(R^2)_2$, a straight-chain alkyl, alkoxy or thioalkoxy group having 1 to 40 C atoms and optionally substituted by one or more radicals $R^2$ or a branched or cyclic alkyl, alkoxy or thioalkoxy group having 3 to 40 C atoms and optionally substituted by one or more radicals $R^2$, wherein one or more H atoms of said straight-chain, branched, or cyclic alkyl, alkoxy, and thioalkoxy groups are optionally replaced by F, CN, an aromatic or heteroaromatic ring system having 5 to 60 aromatic ring atoms and optionally substituted by one or more radicals $R^2$, or an aryloxy or heteroaryloxy group having 5 to 60 aromatic ring atoms and optionally substituted by one or more radicals $R^2$, or a combination of these systems, and wherein two or more substituents R together optionally define a mono- or polycyclic, aliphatic, aromatic, and/or benzo-fused ring system;
$R^1$ is, identically or differently on each occurrence, H, OH, or a $C_1$-$C_{30}$-alkoxy group; and
$R^2$ is, identically or differently on each occurrence, H, F, or an aliphatic, aromatic, and/or heteroaromatic hydrocarbon radical having 1 to 20 C atoms, wherein one or more H atoms of said aliphatic, aromatic, and/or heteroaromatic hydrocarbon radicals are optionally replaced by F, and wherein two or more substituents $R^2$ together optionally define a mono- or polycyclic, aliphatic, aromatic, and/or benzo-fused ring system;
L is a mono- or polydentate ligand.

* * * * *